(12) United States Patent
Holtman et al.

(10) Patent No.: US 9,499,518 B2
(45) Date of Patent: Nov. 22, 2016

(54) BIS-QUATERNARY AMMONIUM SALTS AS PAIN MODULATING AGENTS

(75) Inventors: Joseph R. Holtman, Lisle, IL (US); Peter A. Crooks, Little Rock, AR (US); Linda P. Dwoskin, Lexington, KY (US); J. Michael McIntosh, Salt Lake City, UT (US); Elzbieta Pogonowska Wala, Lexington, KY (US)

(73) Assignees: University of Kentucky Research Foundation, Lexington, KY (US); University of Utah, Salt Lake City, UT (US)

( * ) Notice: Subject to any disclaimer, the term of this patent is extended or adjusted under 35 U.S.C. 154(b) by 514 days.

(21) Appl. No.: 12/880,591

(22) Filed: Sep. 13, 2010

(65) Prior Publication Data

US 2011/0166177 A1    Jul. 7, 2011
US 2016/0279119 A9    Sep. 29, 2016

Related U.S. Application Data

(63) Continuation-in-part of application No. 12/304,948, filed as application No. PCT/US2007/011635 on May 14, 2007, now Pat. No. 8,178,678.

(60) Provisional application No. 61/241,481, filed on Sep. 11, 2009, provisional application No. 60/814,640, filed on Jun. 16, 2006.

(51) Int. Cl.

| | | |
|---|---|---|
| A01N 43/42 | (2006.01) |
| A61K 31/47 | (2006.01) |
| A61K 31/44 | (2006.01) |
| A01N 31/00 | (2006.01) |
| A61K 31/045 | (2006.01) |
| C07D 401/14 | (2006.01) |
| A61K 31/03 | (2006.01) |
| A61K 31/047 | (2006.01) |
| A61K 31/444 | (2006.01) |
| A61K 31/4709 | (2006.01) |
| A61K 31/4725 | (2006.01) |
| C07D 401/06 | (2006.01) |
| C07D 401/10 | (2006.01) |
| C07D 401/12 | (2006.01) |

(52) U.S. Cl.
CPC ............ *C07D 401/14* (2013.01); *A61K 31/03* (2013.01); *A61K 31/047* (2013.01); *A61K 31/444* (2013.01); *A61K 31/4709* (2013.01); *A61K 31/4725* (2013.01); *C07D 401/06* (2013.01); *C07D 401/10* (2013.01); *C07D 401/12* (2013.01)

(58) Field of Classification Search
CPC .. A61K 31/03; A61K 31/047; A61K 31/444; A61K 31/4709; A61K 31/4725; C07D 401/14; C07D 401/06; C07D 401/10; C07D 401/12
USPC ......... 514/308, 314, 332, 333; 546/140, 256
See application file for complete search history.

(56) References Cited

U.S. PATENT DOCUMENTS

2010/0069432 A1*   3/2010   Crooks et al. ................ 514/308

FOREIGN PATENT DOCUMENTS

| WO | WO 2007/094912 | * | 8/2007 |
| WO | WO 2007/149163 | | 12/2007 |

OTHER PUBLICATIONS

Zheng et al. (Biorganic & Medicinal Chemistry Letters, 2007, 6734-38).*

* cited by examiner

*Primary Examiner* — Uma Ramachandran
(74) *Attorney, Agent, or Firm* — Crowell & Moring LLP

(57) ABSTRACT

Provided are methods for using bis-quaternary ammonium compounds to treat inflammatory pain, neuropathic pain and nociceptive pain.

6 Claims, 5 Drawing Sheets

Time Course of Effect of ZZ-16-1C
Rodent Model of Tonic Inflammatory Pain
(Formalin Test)

Dose Response Effect of ZZ-16-1C
Rodent Model of Tonic Inflammatory Pain
(Formalin Test)

BIS-QUATERNARY AMMONIUM SALTS AS PAIN MODULATING AGENTS

FIELD OF THE INVENTION

The invention relates to bis-quaternary ammonium salts and their use as agents for pain modulation, treatment, reversal and/or prevention of inflammatory pain, neuropathic pain or nociceptive pain.

BACKGROUND OF THE INVENTION

The treatment of pain is a critical health issue. Acute (e.g., postoperative pain) and chronic (e.g., arthritis, low back, cancer) pain affects tens of millions of people annually in the US. Each year some 30 million people visit a physician with a complaint of a painful condition. Some 10% of these patients are seen with chronic pain as their main complaint. The financial loss due to pain has been estimated to exceed 100 billion dollars a year as a result of medical fees, decreased productivity, litigation and the cost of drugs. New therapeutic agents with broader efficacy, for nociceptive, neuropathic and mixed nociceptive-neuropathic pain syndromes, and with fewer side effects would result in significant societal benefit.

Pain can be broadly divided into two categories: nociceptive and neuropathic pain. Nociceptive pain occurs as a result of activation of peripheral nociceptors, actually free nerve endings by noxious stimuli (heat, pressure, inflammatory mediators). Examples of nociceptive pain include post-surgical pain, inflammatory pain (e.g., arthritis) and low back pain. Such a pain is often described as "a constant, dull, aching pain". Neuropathic pain occurs as a result of damage to the peripheral or central nervous system. Examples of neuropathic pain include radiculopathy (e.g., disc impingement on a nerve), complex regional pain syndrome (CRPS I, II), diabetic peripheral neuropathy or central pain (stroke, spinal cord injury, multiple sclerosis). Patients typically describe neuropathic pain as "burning and tingling" in nature. It is characterized by hyperalgesia (increased painful response to a noxious stimulus) and allodynia (pain to a previously non-noxious stimulus).

In many pain patients, in particular those with chronic pain conditions of both malignant (cancer-related pain) and non-malignant origin, pain is inadequately managed with currently available drugs. Available drugs are simple modifications (e.g., extended release) of drugs from classes which have been available for decades including the opioids, nonsteroidal anti-inflammatory agents (NSAID's) or various adjuvants (antidepressants, anticonvulsants) initially approved for other uses besides pain. Opioids (e.g., morphine, oxycodone) are often successfully used for the treatment of moderate to severe nociceptive pain. Chronic neuropathic pain is much less responsive to opioids. Use of opioid analgesics is associated with a broad range of significant side effects including cognitive impairment, respiratory depression and constipation. In addition, long-term opioid dosing results in the development of tolerance to the analgesic effect, drug abuse and dependence. The NSAID's (e.g., ibuprofen) act by inhibition of the cyclo-oxygenase (Cox-1,2) enzyme. They are especially useful in nociceptive pain of inflammatory origin (e.g., arthritis). However, the NSAID's have limited efficacy when compared to the opioids. In addition, NSAID's have significant side effects (renal, gastrointestinal, cardiovascular). The discovery of the Cox-2 selective agents (e.g., rofecoxib-Vioxx®; celecoxib-Celebrex®; valdecoxib-Bextra®) which have far less gastrointestinal toxicity, was thought to be an advance in NSAID pharmacology. Nonetheless, these agents still have low efficacy and evidence is now available linking them to significant cardiovascular events including stroke and myocardial infarction following chronic use. This has resulted in the removal of both rofecoxib and valdecoxib from the market. No truly efficacious agent exists for the treatment of neuropathic pain. GABA-pentin (Neurontin®), an anticonvulsant, has found use for some neuropathic pain syndromes (e.g., diabetic peripheral neuropathy, postherpetic neuralgia), but it still has limited efficacy. Duloxetine (Cymbalta®), an antidepressant, has recently been approved for the treatment of diabetic peripheral neuropathy. However, it has limited efficacy and usefulness for other neuropathic pain states. The N-methyl-d-aspartate (NMDA) receptor antagonists (e.g., ketamine) have been proposed for the treatment of neuropathic pain. Their general use is impractical given the marked side effects including sedation, psychosis and motor impairment. The limitations of the currently available therapies clearly demonstrate the need for a broad spectrum new class of efficacious and safe analgesic drugs for the treatment of nociceptive and neuropathic pain.

Given the need for more effective, less toxic, analgesic drugs, a great deal of emphasis has been placed on identifying novel molecular targets that could form the basis for new analgesics. One of the promising new targets is the neuronal nicotinic acetylcholine receptor (nAChR). nAChR's play an important role in the control of pain and thus drugs acting at the nicotinic receptor, as agonists, partial agonists or antagonists may be expected to have analgesic properties. The bis-quaternary ammonia salts of the invention are thought to interact with the nAChR. Nicotinic receptor drugs have been shown to have a broad spectrum of analgesic activity in several preclinical models of pain of nociceptive and neuropathic origin. This includes acute thermal pain models (tail flick, hot plate), inflammatory pain models (formalin or carrageenan injection into the paw) and nerve injury (neuropathic pain) models (spinal or sciatic nerve ligation). Both anti-hyperalgesic and anti-allodynic effects were observed in the neuropathic pain models.

Thus, it appears that nicotine drugs have promise as analgesic agents for the treatment of several types of clinical pain, specifically nociceptive, neuropathic and inflammatory pain.

SUMMARY OF INVENTION

In one embodiment, compounds corresponding to the following structure which are useful in treating inflammatory pain, neuropathic pain or nociceptive pain are provided.

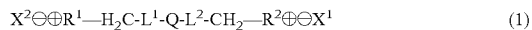
$$X^{2\ominus}\oplus R^1-H_2C-L^1-Q-L^2-CH_2-R^2\oplus\ominus X^1 \quad (1)$$

$X^{1\ominus}$ and $X^{2\ominus}$ are each independently an organic or inorganic anion.

Q is selected from phenylene, biphenylene, —CH=CH—, —CH=CH—CH=CH—, —C≡C—, —C≡C—C≡C—, —O—(CH$_2$)$_2$—O—, and —O—(CH$_2$)$_2$—O—(CH$_2$)$_2$—O—.

$L^1$ and $L^2$ are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; SOY$^1$, SO$_2$Y$^1$, SO$_2$OY$^1$ or SO$_2$NHY$^1$, where Y$^1$ is selected from hydrogen, lower alkyl, alkenyl, alkynyl or aryl, and where Y$^1$ is not hydrogen in SOY$^1$ and if Y$^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$ where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered nitrogen containing rings as shown in formulas (IIA) and (IIB).

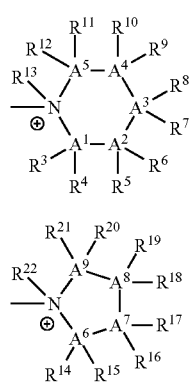

$A^1$ is carbon, nitrogen, sulfur or oxygen, provided that when $A^1$ is a carbon and joins a ring atom with an unsaturated bond or is a nitrogen, $R^3$ is absent, and when $A^1$ is sulfur or oxygen or joins a ring atom with an unsaturated bond and is a nitrogen, both $R^3$ and $R^4$ are absent.

$A^2$ is carbon, nitrogen, sulfur or oxygen, provided that when $A^2$ is a carbon and joins a ring atom with an unsaturated bond or is a nitrogen, $R^5$ is absent, and when $A^2$ is sulfur or oxygen or joins a ring atom with an unsaturated bond and is a nitrogen, both $R^5$ and $R^6$ are absent.

$A^3$ is carbon, nitrogen, sulfur or oxygen, provided that when $A^3$ is a carbon and joins a ring atom with an unsaturated bond or is a nitrogen, $R^7$ is absent, and when $A^3$ is sulfur or oxygen or joins a ring atom with an unsaturated bond and is a nitrogen, both $R^7$ and $R^8$ are absent.

$A^4$ is carbon, nitrogen, sulfur or oxygen, provided that when $A^4$ is a carbon and joins a ring atom with an unsaturated bond or is a nitrogen, $R^9$ is absent, and when $A^4$ is sulfur or oxygen or joins a ring atom with an unsaturated bond and is a nitrogen, both $R^9$ and $R^{10}$ are absent.

$A^5$ is carbon, nitrogen, sulfur or oxygen, provided that when $A^5$ is a carbon and joins a ring atom with an unsaturated bond or is a nitrogen, $R^{11}$ is absent, and when $A^5$ is sulfur or oxygen or joins a ring atom with an unsaturated bond and is a nitrogen, both $R^{11}$ and $R^{12}$ are absent.

$A^6$ is carbon, nitrogen, sulfur or oxygen, provided that when $A^6$ is a carbon and joins a ring atom with an unsaturated bond or is a nitrogen, $R^{14}$ is absent, and when $A^6$ is sulfur or oxygen or joins a ring atom with an unsaturated bond and is a nitrogen, both $R^{14}$ and $R^{15}$ are absent.

$A^7$ is carbon, nitrogen, sulfur or oxygen, provided that when $A^7$ is a carbon and joins a ring atom with an unsaturated bond or is a nitrogen, $R^{16}$ is absent, and when $A^7$ is sulfur or oxygen or joins a ring atom with an unsaturated bond and is a nitrogen, both $R^{16}$ and $R^{17}$ are absent.

$A^8$ is carbon, nitrogen, sulfur or oxygen, provided that when $A^8$ is a carbon and joins a ring atom with an unsaturated bond or is a nitrogen, $R^{18}$ is absent, and when $A^8$ is sulfur or oxygen or joins a ring atom with an unsaturated bond and is a nitrogen, both $R^{18}$ and $R^{19}$ are absent.

$A^9$ is carbon, nitrogen, sulfur or oxygen, provided that when $A^9$ is a carbon and joins a ring atom with an unsaturated bond or is a nitrogen, $R^{20}$ is absent, and when $A^9$ is sulfur or oxygen or joins a ring atom with an unsaturated bond and is a nitrogen, both $R^{20}$ and $R^{21}$ are absent.

$R^{13}$ or $R^{22}$ is absent when any of the bonds to the ammonium nitrogen is unsaturated, and $R^{13}$ or $R^{22}$ is a straight chain or branched alkyl group of four carbons or fewer when all of the bonds to the ammonium nitrogen are saturated.

$R^3$, $R^4$, $R^5$, $R^6$, $R^7$, $R^8$, $R^9$, $R^{10}$, $R^{11}$, and $R^{12}$, or $R^{14}$, $R^{15}$, $R^{16}$, $R^{17}$, $R^{18}$, $R^{19}$, $R^{20}$, and $R^{21}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, or $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ or $R^{22}$ which is attached to the ammonium nitrogen is a straight or branched alkyl group of four carbons or fewer.

In another embodiment, a composition is provided comprising a pharmaceutically acceptable carrier and a compound as described above.

In another embodiment, a method is provided for selectively modulating the function of a nicotinic acetylcholine receptor comprising administering a therapeutically effective amount of a compound as described above to a mammalian subject in need thereof.

In another embodiment, a method is provided for modulating, preventing, treating and/or reversing acute, chronic or cancer pain of central and/or peripheral origin that is referred to as nociceptive, neuropathic, visceral, inflammatory or somatic in nature comprising administering a therapeutically effective amount of a compound as described above to a mammalian subject in need thereof.

DETAILED DESCRIPTION OF INVENTION

Figure 1:
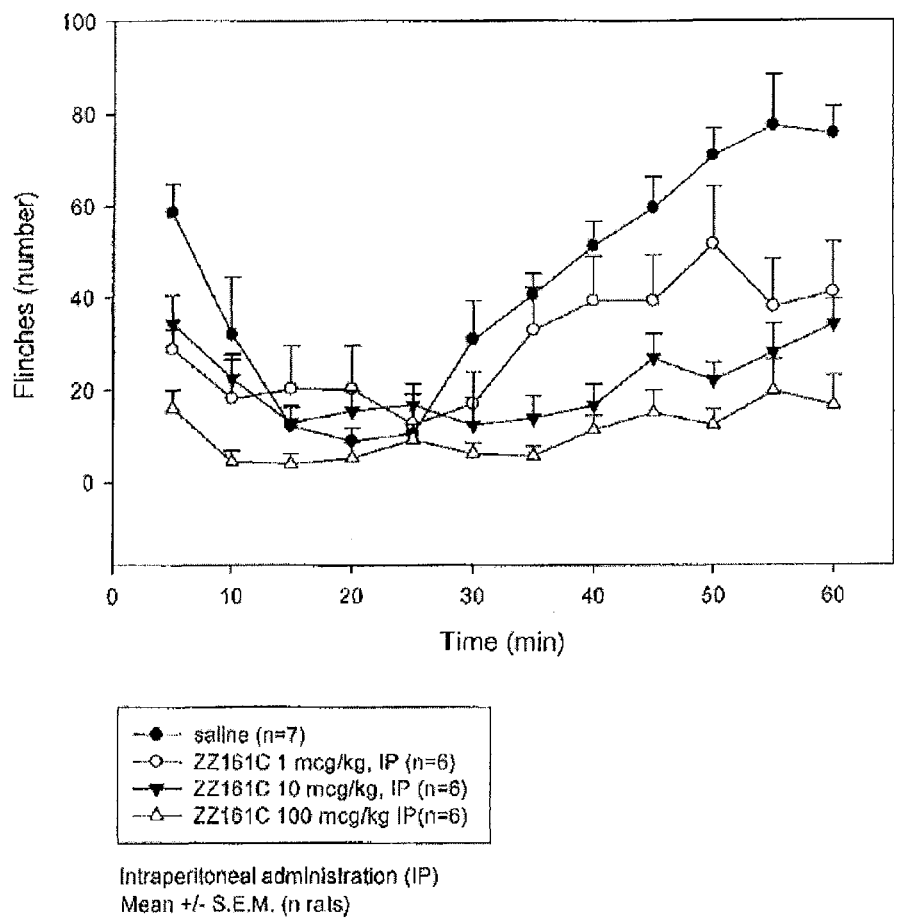
FIG. 1 shows the time course of the analgesic effects of ZZ-1-61C in the rodent formalin persistent inflammatory pain model following intraperitoneal administration. Data are mean±SEM (n=6 rats/dose).

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "alkylaryl" refers to alkyl-substituted aryl groups, and "substituted alkylaryl" refers to alkylaryl groups further bearing one or more substituents as set forth above.

The term "arylalkyl" refers to aryl-substituted alkyl groups, and "substituted arylalkyl" refers to arylalkyl groups further bearing one or more substituents as set forth above.

The term "arylalkenyl" refers to aryl-substituted alkenyl groups, and "substituted arylalkenyl" refers to arylalkenyl groups further bearing one or more substituents as set forth above.

The term "arylalkynyl" refers to aryl-substituted alkynyl groups, and "substituted arylalkynyl" refers to arylalkynyl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "acyl" refers to alkyl-carbonyl groups, and "substituted acyl" refers to acyl groups further bearing one or more substituents as set forth above.

The term "halogen" refers to fluoride, chloride, bromide or iodide groups.

It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are bis-quaternary ammonium salts disclosed in PCT/US2007/011635, filed May 14, 2007 corresponding to Formula (1):

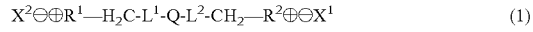

(1)

$X^{1\ominus}$ and $X^{2\ominus}$ are each independently an organic or inorganic anion.

Q is selected from phenylene, biphenylene, —CH═CH—, —CH═CH—CH═CH—, —C≡C—, —C≡C—C≡C—, —O—(CH$_2$)$_2$—O—, and —O—(CH$_2$)$_2$—O—(CH$_2$)$_2$—O—.

$L^1$ and $L^2$ are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; $SOY^1$, $SO_2Y^1$, $SO_2OY^1$ or $SO_2NHY^1$ where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered nitrogen containing rings as shown in formulas (IIA) and (IIB).

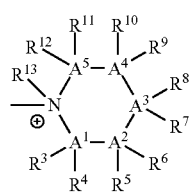

(IIA)

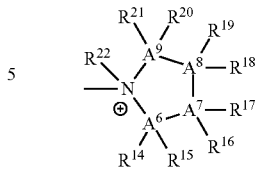

(IIB)

$A^1$ is carbon, nitrogen, sulfur or oxygen, provided that when $A^1$ is a carbon and joins a ring atom with an unsaturated bond or is a nitrogen, $R^3$ is absent, and when $A^1$ is sulfur or oxygen or joins a ring atom with an unsaturated bond and is a nitrogen, both $R^3$ and $R^4$ are absent.

$A^2$ is carbon, nitrogen, sulfur or oxygen, provided that when $A^2$ is a carbon and joins a ring atom with an unsaturated bond or is a nitrogen, $R^5$ is absent, and when $A^2$ is sulfur or oxygen or joins a ring atom with an unsaturated bond and is a nitrogen, both $R^5$ and $R^6$ are absent.

$A^3$ is carbon, nitrogen, sulfur or oxygen, provided that when $A^3$ is a carbon and joins a ring atom with an unsaturated bond or is a nitrogen, $R^7$ is absent, and when $A^3$ is sulfur or oxygen or joins a ring atom with an unsaturated bond and is a nitrogen, both $R^7$ and $R^8$ are absent.

$A^4$ is carbon, nitrogen, sulfur or oxygen, provided that when $A^4$ is a carbon and joins a ring atom with an unsaturated bond or is a nitrogen, $R^9$ is absent, and when $A^4$ is sulfur or oxygen or joins a ring atom with an unsaturated bond and is a nitrogen, both $R^9$ and $R^{10}$ are absent.

$A^5$ is carbon, nitrogen, sulfur or oxygen, provided that when $A^5$ is a carbon and joins a ring atom with an unsaturated bond or is a nitrogen, $R^{11}$ is absent, and when $A^5$ is sulfur or oxygen or joins a ring atom with an unsaturated bond and is a nitrogen, both $R^{11}$ and $R^{12}$ are absent.

$A^6$ is carbon, nitrogen, sulfur or oxygen, provided that when $A^6$ is a carbon and joins a ring atom with an unsaturated bond or is a nitrogen, $R^{14}$ is absent, and when $A^6$ is sulfur or oxygen or joins a ring atom with an unsaturated bond and is a nitrogen, both $R^{14}$ and $R^{15}$ are absent.

$A^7$ is carbon, nitrogen, sulfur or oxygen, provided that when $A^7$ is a carbon and joins a ring atom with an unsaturated bond or is a nitrogen, $R^{16}$ is absent, and when $A^7$ is sulfur or oxygen or joins a ring atom with an unsaturated bond and is a nitrogen, both $R^{16}$ and $R^{17}$ are absent.

$A^8$ is carbon, nitrogen, sulfur or oxygen, provided that when $A^8$ is a carbon and joins a ring atom with an unsaturated bond or is a nitrogen, $R^{18}$ is absent, and when $A^8$ is sulfur or oxygen or joins a ring atom with an unsaturated bond and is a nitrogen, both $R^{18}$ and $R^{19}$ are absent.

$A^9$ is carbon, nitrogen, sulfur or oxygen, provided that when $A^9$ is a carbon and joins a ring atom with an unsaturated bond or is a nitrogen, $R^{20}$ is absent, and when $A^9$ is sulfur or oxygen or joins a ring atom with an unsaturated bond and is a nitrogen, both $R^{20}$ and $R^{21}$ are absent.

$R^{13}$ or $R^{22}$ is absent when any of the bonds to the ammonium nitrogen is unsaturated, and $R^{13}$ or $R^{22}$ is a straight chain or branched alkyl group of four carbons or fewer when all of the bonds to the ammonium nitrogen are saturated.

$R^3$, $R^4$, $R^5$, $R^6$, $R^7$, $R^8$, $R^9$, $R^{10}$, $R^{11}$, and $R^{12}$, or $R^{14}$, $R^{15}$, $R^{16}$, $R^{17}$, $R^{18}$, $R^{19}$, $R^{20}$, and $R^{21}$, when present, are each independently selected from hydrogen, alkyl, substituted alkyl, cycloalkyl, substituted cycloalkyl, alkenyl, substituted alkenyl, alkynyl, substituted alkynyl, aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, or $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ or $R^{22}$ which is attached to the ammonium nitrogen is a straight or branched alkyl group of four carbons or fewer.

For example, $R^1$ and $R^2$ include pyrrole, pyrrolidine, pyrazole, imidazole, oxazole, isoxazole, thiazole, isothiazole, oxadiazole, oxatriazole, dioxazole, 1,2,3-triazole, 1,2,4-triazole, pyridine, pyrimidine, piperidine, quinoline, tetrahydroquinoline, isoquinoline, tetrahydroisoquinoline, pyrazine, piperazine, pyridazine, triazine, oxazine, phenazine, pteridine, benzoxazine, phthalazine, naphthridine, quinoxaline, quinazoline, cinnoline, quinuclidine, benzothiazole, benzisoxazole, benzoxazole, indazole, pyranopyrrole, cyclopentapyridine, benzimidazole, isoindole, 3H-indole, indolene and triazine.

As another example, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, $R^{18}$, $R^{19}$, $R^{20}$, and $R^{21}$, include hydrogen, methyl, ethyl, propyl, butyl, hydroxymethyl, hydroxyethyl, hydroxypropyl, trifluoromethyl, chloro, bromo, phenyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo [3.2.1] octane, 1-aza-bicyclo [2.2.1] heptane, 8-methyl-8-aza-bicyclo [3.2.1] octane, 1-aza-tricyclo [3.3.1.13,7] decane, methyl cycloalkyl, methyl substituted cycloalkyl, methyl pyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-azabicyclo [3.2.1] octane, methyl-1-aza-bicyclo [2.2.1] heptane, 8-methyl-8-aza-bicyclo [3.2.1] octane, and methyl-1-aza-tricyclo [3.3.1.13'7] decane.

As a further example, when $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight-membered ring, that ring may be a heterocycle containing up to three hetero atoms (for example nitrogen, oxygen or sulfur) in the ring, and further may be substituted with one or more substituents. For example, possible rings include benzene, pyridine, pyran, indene, isoindene, benzofuran, isobenzofuran, benzo [b]thiophene, benzo[c]thiophene, indole, indolenine, isoindole, cyclopental[b]pyridine, pyrano[3,4-b]pynrole, indazole, indoxazine, benzoxazole, anthranil, naphthalene, tetralin, decalin, chromene, coumarin, chroman-4-one, isocoumarin, isochromen-3-one, quinoline, isoquinoline, cinnoline, quinazoline, naphthyrdine, pyrido[3,4-b]-pyridine, pyridol[3,2-b]pyridine, pyrido[4,3,-b]-pyridine, benzoxazine, anthracene, phenanthrene, phenalene, fluorene, carazole, xanthene, acnidine, octahydro-[1]pyridine, 1-methyloctahydro-[1]pyridine, octahydroindole, 1-methyloctahydro-indole, octahydro-cyclopenta[b]pyrrole, 1-methyloctahydro-cyclopenta[b]pyrrole, decahydroquinoline, and 1-methyldecahydroquinoline.

$X^{1\ominus}$ and $X^{2\ominus}$, for example $F^-$, $Cl^-$, $Br^-$, $I^-$, $NO_2^-$, $HSO_4^-$, $SO_4^-$, $HPO_4^-$, $PO_4^{2-}$, methanesulfonate, trifluromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms may be in some cases hydrates or solvates with alcohols and other solvents.

In a compound of Formula (I), preferably $R^1$ and $R^2$ are substituted, six-membered, aromatic rings. More preferably, $R^1$ and $R^2$ are substituted pyridinium rings. In other preferred embodiments, $R^1$ and $R^2$ are quinoline, isoquinoline, tetrahydroquinoline or tetrahydroisoquinoline.

In a compound of Formula (I), preferably $R^{13}$ is absent.

In a compound of Formula (I), preferably $R^3$, $R^4$, $R^5$, $R^6$, $R^7$, $R^8$, $R^9$, $R^{10}$, $R^{11}$ or $R^{12}$ is absent or is hydrogen, alkyl, hydroxyalkyl, halo, phenyl or 1-alkyl-2-pyrrolidinyI. More preferably, $R^3$, $R^4$, $R^5$, $R^6$, $R^7$, $R^8$, $R^9$, $R^{10}$, $R^{11}$ or $R^{12}$ is absent or is hydrogen, methyl, ethyl, propyl, butyl, hydroxymethyl, hydroxyethyl, hydroxypropyl, bromo, phenyl or 1-methyl-2-pyrrolidinyl.

In a compound of Formula (I), preferably Q is phenylene, biphenylene, —CH=CH—CH=CH—, —C≡C—C≡C— and —O—(CH$_2$)$_2$—O—(CH$_2$)$_2$—O—.

In a compound of Formula (I), preferably $L^1$ and $L^2$ are the same and are —CH$_2$—, —(CH$_2$)$_2$—, —(CH$_2$)$_3$—, —(CH$_2$)$_4$—, —C≡C—, —CH$_2$—C≡C— or —(CH$_2$)$_2$—C≡C—.

In a compound of Formula (I), preferably $X^1$ SYMBOL and $X^2$ SYMBOL are halogens. More preferably, $X^1$ SYMBOL and $X^2$ SYMBOL are chloride or bromide.

In another embodiment, the compound of Formula (I) is defined wherein -L$_1$-Q-L$_2$- is —(CH$_2$)$_4$-1,2-phenylene-(CH$_2$)$_4$—, —(CH$_2$)$_4$-1,3-phenylene-(CH$_2$)$_4$—, —(CH$_2$)$_3$-1,4-phenylene-(CH$_2$)$_3$—, —(CH$_2$)$_2$-4,4'-biphenylene-(CH$_2$)$_2$—, —(CH$_2$)$_2$—C≡C-1,2-phenylene-C≡C—(CH$_2$)$_2$—, —(CH$_2$)$_2$—C≡C-1,3-phenylene-C≡C—(CH$_2$)$_2$—, —CH$_2$—C≡C-1,4-phenylene-C≡C—CH$_2$—, —C≡C-4,4'-biphenylene-C≡C—, —(CH$_2$)$_3$—CH=CH—CH=CH—(CH$_2$)$_3$—, —(CH$_2$)$_3$—C≡C—C≡C—(CH$_2$)$_3$— or —CH$_2$—O—(CH$_2$)$_2$—O—(CH$_2$)$_2$—O—CH$_2$—, $R^1$ and $R^2$ are pyridinium rings, $R^3$ is hydrogen or methyl, $R^5$ is hydrogen, methyl, ethyl, butyl, phenyl, 1-methyl-2-pyrrolidinyl, bromo, hydroxymethyl or hydroxypropyl, $R^7$ is hydrogen or methyl, $R^9$ is hydrogen or methyl, $R^{11}$ is hydrogen, and $X^1$ and $X^2$ are chloride or bromide.

In another embodiment, the compound of Formula (I) is defined wherein -L$_1$-Q-L$_2$- is —(CH$_2$)$_4$-1,2-phenylene- —(CH$_2$)$_4$—, —(CH$_2$)$_4$-1,3-phenylene-(CH$_2$)$_4$—, —(CH$_2$)$_3$-1,4-phenylene-(CH$_2$)$_3$—, —(CH$_2$)$_2$-4,4'-biphenylene-(CH$_2$)$_2$—, —(CH$_2$)$_2$—C≡C-1,2-phenylene-C≡C—(CH$_2$)$_2$—, —(CH$_2$)$_2$—C≡C-1,3-phenylene-C≡C—(CH$_2$)$_2$—, —CH$_2$—C≡C-1,4-phenylene-C≡C—CH$_2$—, —C≡C-4,4'-biphenylene-C≡C—, —(CH$_2$)$_3$—CH═CH—CH═CH—(CH$_2$)$_3$—, —(CH$_2$)$_3$—C≡C—C≡C—(CH$_2$)$_3$— or —CH$_2$—O—(CH$_2$)$_2$—O—(CH$_2$)$_2$—O—CH$_2$—, R$^1$ and R$^2$ are quinoline, isoquinoline, tetrahydroquinoline or tetrahydroisoquinoline, and X$^1$ and X$^2$ are chloride or bromide.

Exemplary compounds of the present invention include:

cis-cis-N,N'-(dodeca-5,7-diene-1,12-diyl)-bis-[3-(2'-5-1-methyl-pyrrolidin-2-yl)-pyridinium] dibromide;
cis-cis-N,N'-(dodeca-5,7-diene-1,12-diyl)-bis-{2-methyl-1-pyridinium) dibromide;
cis-cis-N,N'-(dodeca-5,7-diene-1,12-diyl)-bis-(3-methyl-pyridinium) dibromide;
cis-cis-N,N'-(dodeca-5,7-diene-1s12-diyl)-bis-(4-methyl-pyridinium) dibromide;
cis-cis-N,N'-(dodeca-5,7-diene-1,12-diyl)-bis-(5,6,7,8-tetrahydro-quinolinium) dibromide;
cis-cis-N,N'-(dodeca-5,7-diene-1,12-diyl)-bis-(5,6,7,8-tetrahydro-isoquinolinium) dibromide;
cis-cis-N,N'-(dodeca-5,7-diene-1,12-diyl)-bis-(2,4-dimethyl-pyridinium) dibromide;
cis-cis-N,N'-(dodeca-5,7-diene-1,12-diyl)-bis-(3,4-dimethyl-pyridinium) dibromide;
cis-cis-N,N'-(dodeca-5,7-diene-1,12-diyl)-bis-(3,5-dimethyl-pyridinium) dibromide;
N,N'-[1,4-phenylenedi-(4-butanyl)]-bis-[3-(2'-S-1-methyl-pyrrolidin-2-yl)-pyridinium]dibromide;
N,N'-[1,4-phenylenedi-(4-butanyl)]-bis-(2-methylpyridinium) dibromide;
N,N'-[1,4-phenylenedi-(4-butanyl)]-bis-(3-methylpyridinium) dibromide;
N,N'-[1,4-phenylenedi-(4-butanyl)]-bis-(4-methylpyridinium) dibromide;
N,N'-[1,4-phenylenedi-(4-butanyl)]-bis-(3-ethylpyridinium) dibromide;
N,N'-[1,4-phenylenedi-(4-butanyl)]-bis-(5,6,7,8-tetrahydroquinolinium) dibromide;
N,N'-[1,4-phenylenedi-(4-butanyl)]-bis-(5,6,7,8-tetrahydroisoquinolinium) dibromide;
N,N'-[1,4-phenylenedi-(4-butanyl)]-bis-[3-(3-hydroxy-propyl)-pyridinium] dibromide;
N,N'-[1,4-phenylenedi-(4-butanyl)]-bis-(2,4-dimethylpyridinium) dibromide;
N,N'-[1,4-phenylenedi-{4-butanyl)]-bis-(3,4-dimethylpyridinium) dibromide;
N,N'-[1,4-phenylenedi-{4-butanyl)]-bis-(3,5-dimethylpyridinium) dibromide;
1,2-bis-[5-(2-methyl-pyridinium)-pent-1-ynyl]-benzene dibromide;
1,2-bis-[5-(3-methyl-pyridinium)-pent-1-ynyl]-benzene dibromide;
1,2-bis-[5-(4-methyl-pyridinium)-pent-1-ynyl]-benzene dibromide;
1,2-bis-[5-(2,4-dimethyl-pyridinium)-pent-1-ynyl]-benzene dibromide;
1,2-bis-[5-(3,4-dimethyl-pyridinium)-pent-1-ynyl]-benzene dibromide;
1,2-bis-[5-(3,5-dimethyl-pyridinium)-pent-1-ynyl]-benzene dibromide;
1,2-bis-(5-quinolinium-pent-1-ynyl)-benzene dibromide;
1,2-bis-(5-isoquinolinium-pent-1-ynyl)-benzene dibromide;
1,2-bis-(5-S-nicotinium-pent-1-ynyl)-benzene dibromide;
1,2-bis-[5-(2-methyl-pyridinium)-pentyl]-benzene dibromide;
1,2-bis-[5-(3-methyl-pyridinium)-pentyl]-benzene dibromide;
1,2-bis-[5-(4-methyl-pyridinium)-pentyl]-benzene dibromide;
1,2-bis-[5-(2,4-dimethyl-pyridinium)-pentyl]-benzene dibromide;
1,2-bis-[5-(3,4-dimethyl-pyridinium)-pentyl]-benzene dibromide;
1,2-bis-[5-(3,5-methyl-pyridinium)-pentyl]-benzene dibromide;
1,2-bis-(5-quinolinium-pentyl)-benzene dibromide;
1,2-bis-(5-isoquinolinium-pentyl)-benzene dibromide;
1,2-bis-(5-S-nicotinium-pentyl)-benzene dibromide;
1,2-bis-[5-(3-n-butyl-pyridinium)-pentyl]-benzene dibromide;
1,2-bis-[5-(3-bromo-pyridinium)-pentyl]-benzene dibromide;
1,2-bis-(5-pyridinium-pentyl)-benzene dibromide;
1,3-bis-[5-(2-methyl-pyridinium)-pent-1-ynyl]-benzene dibromide;
1,3-bis-[5-(3-methyl-pyridinium)-pent-1-ynyl]-benzene dibromide;
1,3-bis-[5-(4-methyl-pyridinium)-pent-1-ynyl]-benzene dibromide;
1,3-bis-[5-(2,4-dimethyl-pyridinium)-pent-1-ynyl]-benzene dibromide;
1,3-bis-[5-(3,4-dimethyl-pyridinium)-pent-1-ynyl]-benzene dibromide;
1,3-bis-[5-(3,5-dimethyl-pyridinium)-pent-1-ynyl]-benzene dibromide;
1,3-bis-(5-quinolinium-pent-1-ynyl)-benzene dibromide;
1,3-bis-(5-isoquinolinium-pent-1-ynyl)-benzene dibromide;
1,3-bis-(5-S-nicotinium-pent-1-ynyl)-benzene dibromide;
1,3-bis-[5-(3-n-butyl-pyridinium)-pent-1-ynyl]-benzene dibromide;
1,3-bis-[5-(3-phenyl-pyridinium)-pent-1-ynyl]-benzene dibromide;
1,3-bis-(5-pyridinium-pent-1-ynyl)-benzene dibromide;
1,3-bis-[5-(2-methyl-pyridinium)-pentyl]-benzene dibromide;
1,3-bis-[5-(3-methyl-pyridinium)-pentyl]-benzene dibromide;
1,3-bis-[5-(4-methyl-pyridinium)-pentyl]-benzene dibromide;
1,3-bis-[5-(2,4-dimethyl-pyridinium)-pentyl]-benzene dibromide;
1,3-bis-[5-(3,4-dimethyl-pyridinium)-pentyl]-benzene dibromide;
1,3-bis-[5-(3,5-dimethyl-pyridinium)-pentyl]-benzene dibromide;
1,3-bis-(5-quinolinium-pentyl)-benzene dibromide;
1,3-bis-(5-isoquinolinium-pentyl)-benzene dibromide;
N,N'-[(1,1'-biphenyl)-4,4'-di-(3-propanyl)]-bis-[3-(2'-S-1-methyl-pyrrolidin-2-yl)-pyridinium] dibromide;
N,N'-[(1,1'-biphenyl)-4,4'-di-(3-propanyl)]-bis-(3,5-dimethylpyridinium) dibromide;
N,N'-[(1,1'-biphenyl)-4,4'-di-(3-propanyl)]-bis-(3,4-dimethylpyridinium) dibromide;
N,N'-[(1,1'-biphenyl)-4,4'-di-(3-propanyl)]-bis-(2,4-dimethylpyridinium) dibromide;
N,N'-[(1,1'-biphenyl)-4,4'-di-(3-propanyl)]-bis-[3-(3-hydroxy-propyl)-pyridinium]dibromide;
N,N'-[(1,1'-biphenyl)-4,4'-di-(3-propanyl)]-bis-[5,6,7,8-tetrahydroquinolinium]dibromide;

N,N'-[(1,1'-biphenyl)-4,4'-di-(3-propanyl)]-bis-[5,6,7,8-tetrahydroisoquinolinium]dibromide;
N,N'-[(1,1'-biphenyl)-4,4'-di-(3-propanyl)]-bis-(4-methylpyridinium) dibromide;
N,N'-[(1,1'-biphenyl)-4,4'-di-(3-propanyl)]-bis-(3-methyipyridinium) dibromide;
N,N'-[(1,1'-biphenyl)-4,4'-di-(3-propanyl)]-bis-(2-methylpyridinium) dibromide;
N,N'-{2,2'-[oxybis(2,1-ethandiyloxy)]bis-ethyl}-bis-[3-(2'-S-1-methyl-pyrrolidin-2-yl)-pyridinium]dichloride;
N,N'-{2,2'-[oxybis(2,1-ethandiyloxy)]bis-ethyl}-bis(2-methylpyridinium) dichloride;
N,N'-{2,2'-[oxybis(2,1-ethandiyloxy)]bis-ethyl}-bis(3-methylpyridinium) dichloride;
N,N'-{2,2'-[oxybis(2,1-ethandiyloxy)]bis-ethyl}-bis(4-methylpyridinium) dichloride;
N,N'-{2,2'-[oxybis(2,1-ethandiyloxy)]bis-ethyl}-bis(5,6,7,8-tetrahydroquinolinium) dichloride;
N,N'-{2,2'-[oxybis(2,1-ethandiyloxy)]bis-ethyl}-bis(5,6,7,8-tetrahydroisoquinolinium) dichloride;
N,N'-{2,2'-[oxybis(2,1-ethandiyloxy)]bis-ethyl}-bis-[3-(3-hydroxypropyl)-pyridinium]dichloride;
N,N'-{2,2'-[oxybis(2,1-ethandiyloxy)]bis-ethyl}-bis(3-hydroxymethylpyridinium) dichloride;
N,N'-{2,2'-[oxybis(2,1-ethandiyloxy)]bis-ethyl}-bis(2,4-dimethylpyridinium) dichloride;
N,N'-{2,2'-[oxybis(2,1-ethandiyloxy)]bis-ethyl}-bis(3,4-dimethylpyridinium) dichloride;
N,N'-{2,2'-[oxybis(2,1-ethandiyloxy)]bis-ethyl}-bis(3,5-dimethylpyridinium) dichloride;
N,N'-(5,7-dodecadiyn-1,12-diyl)-bis-(2-methylpyridinium) dichloride;
N,N'-(5,7-dodecadiyn-1,12-diyl)-bis-(3-methylpyridinium) dichloride;
N,N'-(5,7-dodecadiyn-1,12-diyl)-bis-(4-methylpyridinium) dichloride;
N,N'-(5,7-dodecadiyn-1,12-diyl)-bis-(3,4-dimethylpyridinium) dichloride;
N,N'-(5,7-dodecadiyn-1,12-diyl)-bis-(3,5-dimethylpyridinium) dichloride;
N,N'-(5,7-dodecadiyn-1,12-diyl)-bis-(5,6,7,8-tetrahydroisoquinolinium) dichloride;
N,N'-[(1,4-phenylene)-bis-(4-butynyl)]-bis-(3-methyl-pyridinium) dibromide;
N,N'-[(1,4-phenylene)-bis-(4-butynyl)]-bis-(4-methyl-pyridinium) dibromide;
N,N'-[(1,4-phenylene)-bis-(4-butynyl)]-bis-(5,6,7,8-tetrahydroisoquiolinium) dibromide;
N,N'-[(1,4-phenylene)-bis-(4-butynyl)]-bis-(3,4-dimethylpyridinium) dibromide;
N,N'-[(1,4-phenylene)-bis-(4-butynyl)]-bis-(3,5-dimethylpyridiniuim) dibromide;
N,N'-[(1,1'-biphenyl)-4,4'-di-(1-propyn-3-yl)]-bis-(3-methylpyridinium) dibromide;
N,N'-[(1,1'-biphenyl)-4,4'-di-(1-propyn-3-yl)]-bis-(4-methylpyridinium) dibromide;
N,N'-[(1,1'-biphenyl)-4,4'-di-(1-propyn-3-yl)]-bis-(3,4-dimethylpyridinium) dibromide.

The compounds of the present invention may contain one or more stereocenters. The invention includes all possible diastereomers and all enantiomeric forms as well as all combinations of diastereomers and enantiomers, including racemic mixtures. The compounds can be separated into substantially optically pure compounds.

Pain from nervous system disorders of central and/or peripheral origin, which may be treated according to the method of the present invention and includes any disorders involving pain including those types of pain referred to as nociceptive, neuropathic (chemical, viral or disease-induced), inflammatory (arthritis, irritable bowel disease, Crohn's) as well as acute, chronic, cancer-related, and surgical, as well as pain resulting from any and all injuries, diseases or toxin induced injuries of the central or peripheral nervous systems including pain accompanying stroke, multiple sclerosis, parkinson's disease and pain from peripheral neuropathy as a result of diabetes, AIDs, chemotherapeutic drugs, and/or alcohol.

Pain from cancer which may have its origin at any peripheral or central site and be caused by tumor invasion of bone, tissue or nerve. In another embodiment, the present invention is directed to a method for treating and/or preventing neuropathy resulting from a medication which causes neuropathic pain as a side effect. For example, the compounds of the present invention may be used to treat and/or prevent pain associated with chemotherapy drugs such as vincristine. This is a very serious clinical condition associated with anticancer drugs.

In yet another embodiment, the present invention is directed to a method for preventing and/or treating inflammatory pain disorders comprising administering to a mammalian subject in need thereof a therapeutically effective amount of a compound of Formula (I).

Inflammatory pain disorders which may be treated according to the method of the present invention include ankylosing spondylitis, benign prostatic hyperplasia, cholecystitis, ulcerative colitis, Crohn's disease, diabetes mellitus, gastritis, glomerulonephritis, irritable bowel syndrome, multiple sclerosis, osteoarthritis, pancreatitis, polymyositis, psoriasis and rheumatoid arthritis.

The compounds of the present invention can be delivered to a mammalian organism, including a human, directly or in pharmaceutical compositions along with suitable carriers or excipients, as is well known in the art. For example, a pharmaceutical composition of the invention may include a conventional additive, such as a stabilizer, buffer, salt, preservative, filler, flavor enancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray, including a sublingual tablet or a sublingual spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies. A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Synthesis of Compound cis-cis-N,N'-(dodeca-5,7-diene-1,12-diyl)-bis-[3-(2'-S-1-methyl-pyrrolidin-2-yl)-pyridinium] dibromide

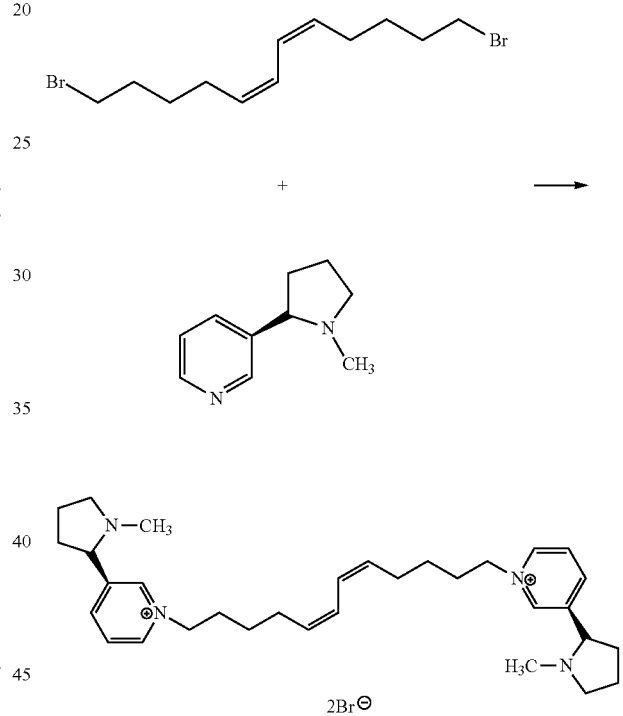

cis-cis-1,12-Dibromo-dodeca-5,7-diene (1 mmol) was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (70%). $^1$HNMR (300 MHZ, $D_2O$, ppm) 8.60 (s, 2H), 8.59 (d, 2H), 8.32 (d, J=8.4, 2H), 7.88 (t, J=5.7, 2H), 6.12-6.20 (m, 2H), 5.30-5.40 (m, 2H), 4.43 (t, J=7.2, 4H), 3.39 (t, J=8.4, 2H), 3.01-3.06 (m, 2H), 2.16-2.34 (m, 4H), 2.01-2.09 (m, 10H), 1.64-1.88 (m, 10H), 1.25 (p, J=7.5, 4H). $^{13}$CNMR, 144.67, 143.35, 132.20, 128.45, 124.12, 67.65, 62.05, 56.65, 39.41, 33.76, 30.32, 26.34, 25.47, 22.36.

Example 2

Synthesis of Compound cis-cis-N,N'-(dodeca-5,7-diene-1,12-diyl)-bis-(2-methyl-pyridinium) dibromide

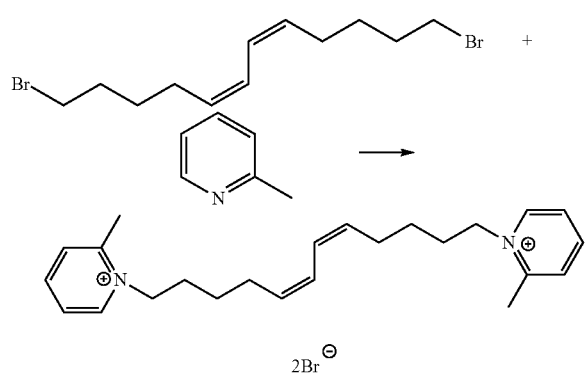

cis-cis-1,12-Dibromo-dodeca-5,7-diene was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer. The resulting aqueous solution of the product was lyophilized to yield the pure product. (76%). $^1$HNMR (300 MHz, $D_2O$, ppm) 8.52 (dd, J=6.3, 2H), 8.17 (dt, J=7.8, J=1.5, 2H), 7.72 (d, J=7.8, 2H), 7.64 (t, J=6.3, 2H), 6.18-6.23 (m, 2H), 5.33-5.41 (m, 2H), 4.37 (t, J=7.1, 4H), 2.66 (s, 6H), 2.09 (q, J=7.5, 4H), 1.72-1.82 (m, 4H), 1.36 (p, J=7.5, 4H). $^{13}$CNMR, 155.26, 145.01, 144.73, 132.25, 130.23, 125.64, 124.15, 58.06, 29.10, 26.38, 25.61, 19.73.

Example 3

Synthesis of Compound cis-cis-N,N'-(dodeca-5,7-diene-1,12-diyl)-bis-(3-methyl-pyridinium) dibromide

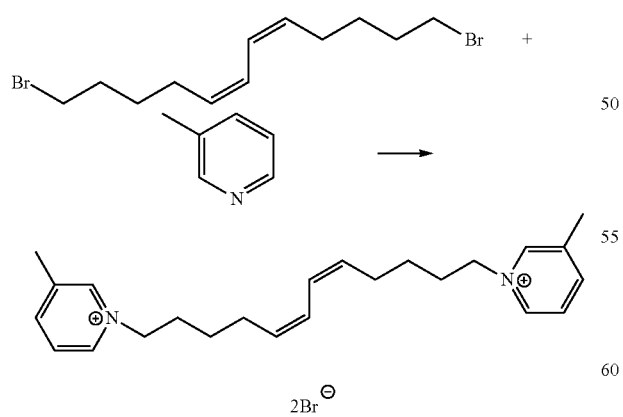

cis-cis-1,12-Dibromo-dodeca-5,7-diene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer. The resulting aqueous solution of the product was lyophilized to yield the pure product. (76%). $^1$HNMR (300 MHz, $D_2O$, ppm) 8.50 (s, 2H), 8.44 (d, J=6.3, 2H), 8.16 (d, J=7.8, 2H), 7.74 (dd, J=7.8, J=6.3, 2H), 6.15-6.18 (m, 2H), 5.38-5.38 (m, 2H), 4.38 (t, J=5.7, 4H), 2.35 (s, 6H), 2.06 (q, J=7.5, 4H), 1.83 (p, J=7.5, 4H), 1.25 (p, J=7.5, 4H). $^{13}$CNMR, 145.99, 143.71, 141.30, 139.95, 132.19, 127.46, 124.06, 61.69, 30.27, 26.35, 25.44, 17.93.

Example 4

Synthesis of Compound cis-cis-N,N'-(dodeca-5,7-diene-1,12-diyl)-bis-(4-methyl-pyridinium) dibromide

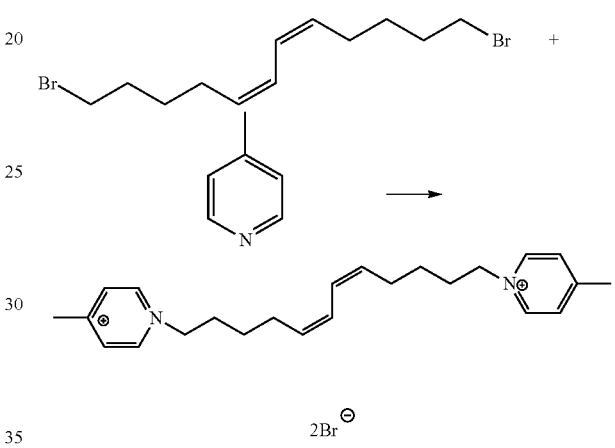

cis-cis-1,12-Dibromo-dodeca-5,7-diene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer. The resulting aqueous solution of the product was lyophilized to yield the pure product. (75%). $^1$HNMR (300 MHz, $D_2O$, ppm), 8.45 (d, J=6.9, 4H), 7.68 (d, J=6.9, 4H), 6.14-6.19 (m, 2H), 5.31-5.39 (m, 2H), 4.35 (t, J=7.2, 4H), 2.47 (s, 6H), 2.07 (q, J=7.2, 4H), 1.83 (p, J=7.5, 4H), 1.25 (p, J=7.5, 4H).

Example 5

Synthesis of Compound cis-cis-N,N'-(dodeca-5,7-diene-1,12-diyl)-bis-(5,6,7,8-tetrahydro-quinolinium) dibromide

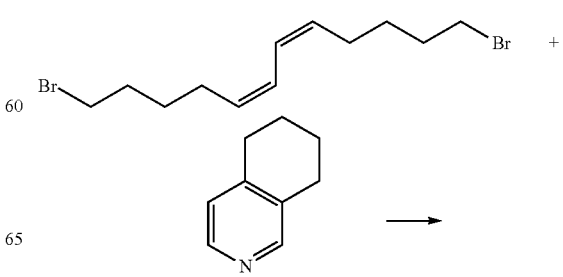

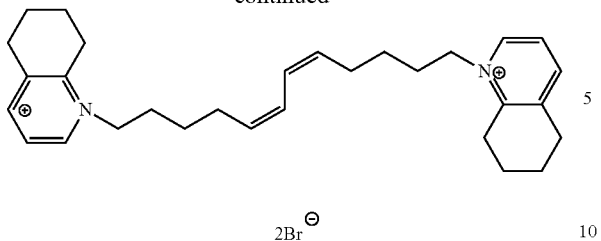

cis-cis-1,12-Dibromo-dodeca-5,7-diene was added to a solution of 5,6,7,8-tetrahydro-quinoline (3 mmol) in acetonitrile and the solution refluxed for 24 hours. The acetonitrile was removed in vacuum and the resulting residue was partitioned between ether and water. The aqueous layer was washed extensively with ether until no quinoline left in the aqueous layer. The resulting aqueous solution of the product was lyophilized to yield the pure product. (75%). $^1$HNMR (300 MHz, D$_2$O, ppm) 8.35 (d, J=6.3, 2H), 7.97 (d, J-8.1, 2H), 7.52 (dd, J=8.1, J=6.3, 2H), 6.16-6.22 (m, 2H), 5.32-5.42 (m, 2H), 4.30 (t, J=7.8, 4H), 2.92 (t, J=6.2, 4H), 2.79 (t, J=6.2, 4H), 2.09 (q, J=7.2, 4H), 1.60-1.83 (m, 12H), 1.36 (p, J=7.5S 4H).

Example 6

Synthesis of Compound cis-cis-N,N'-(dodeca-5,7-diene-1,12-diyl)-bis-(5,6,7,8-tetrahydro-isoquinolinium) dibromide

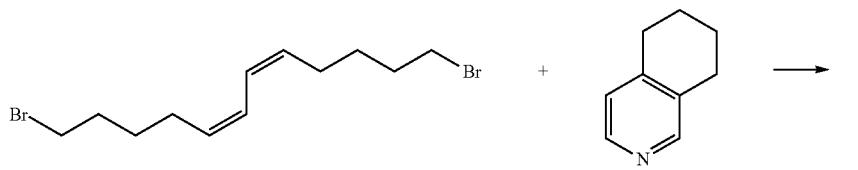

cis-cis-1,12-Dibromo-dodeca-5,7-diene was added to a solution of 5,6,7,8-tetrahydro-isoquinoline (3 mmol) in acetonitrile and the solution refluxed for 24 hours. The acetonitrile was removed in vacuum and the resulting residue was partitioned between ether and water. The aqueous layer was washed extensively with ether until no isoquinoline left in the aqueous layer. The resulting aqueous solution of the product was lyophilized to yield the pure product. (75%). $^1$HNMR (300 MHz, D$_2$O, ppm) 8.30 (s, 2H), 8.19 (d, J=6.6, 2H), 7.50 (d, J=6.3, 2H), 6.09-6.16 (m, 2H), 5.28-5.36 (m, 2H), 4.27 (t, J=7.2, 4H), 2.29-2.82 (br, 4H), 2.67-2.74 (br, 4H), 2.02 (q, J=7.2, 4H), 1.81 (p, J=7.2, 4H), 1.62-1.69 (m, 8H), 1.22 (p, J=7.2, 4H). CNMR158.82, 143.10, 139.60, 138.96, 132.28, 127.92, 124.09, 60.82, 49.13, 30.07, 29.35, 26.32, 26.20, 25.43, 21.01.

Example 7

Synthesis of Compound cis-cis-N,N'-(dodeca-5,7-diene-1,12-diyl)-bis-(2,4-dimethyl-pyridinium) dibromide

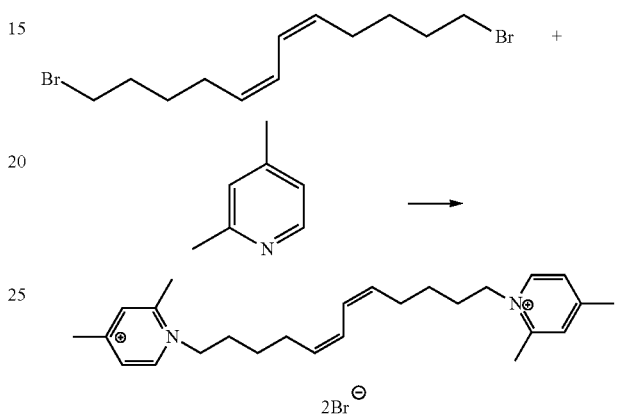

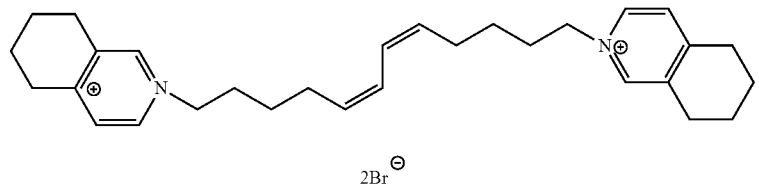

cis-cis-1,12-Dibromo-dodeca-5,7-diene was added to a solution of 2, 4-lutidine {3 mmol) in acetonitrile and the solution refluxed for 24 hours. The acetonitrile was removed in vacuum and the resulting residue was partitioned between ether and water. The aqueous layer was washed extensively with ether until no 2, 4-lutidine left in the aqueous layer. The resulting aqueous solution of the product was lyophilized to yield the pure product. (75%). $^1$HNMR (300 MHZ, D$_2$O, ppm) 8.31 (d, J=6.3, 2H), 7.53 (s, 2H), 7.46 (d, J=6.9, 2H), 6.16-6.22 (m, 2H), 5.32-5.40 (m, 2H), 4.28 (t, J=8.1, 4H), 2.58 (s, 3H), 2.38 (s, 3H), 2.07 (q, J=7.2, 4H), 1.74 (p, J=7.5, 4H), 1.33 (p, J=7.5, 4H). CNMR, 159.20, 153.87, 143.69, 132.32, 130.44, 126.34, 124.18, 57.19, 29.10, 26.41, 25.63, 21.19, 19.46.

Example 8

Synthesis of Compound cis-cis-N,N'-(dodeca-5,7-diene-1,12-diyl)-bis-(3,4-dimethyl-pyridinium) dibromide

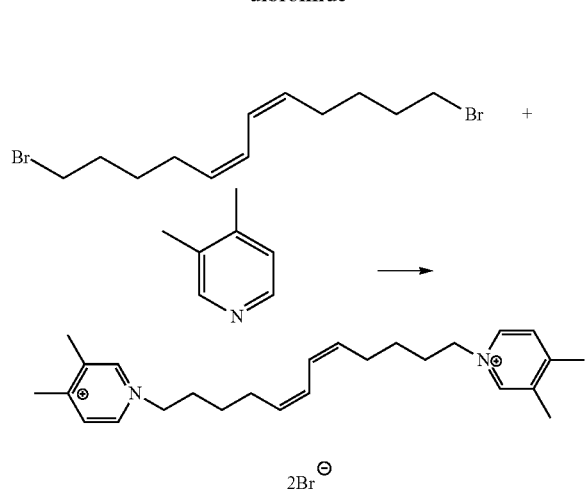

cis-cis-1,12-Dibromo-dodeca-5,7-diene was added to a solution of 3, 4-lutidine (3 mmol) in acetonitrile and the solution refluxed for 24 hours. The acetonitrile was removed in vacuum and the resulting residue was partitioned between ether and water. The aqueous layer was washed extensively with ether until no 3, 4-lutidine left in the aqueous layer. The resulting aqueous solution of the product was lyophilized to yield the pure product. (75%). $^1$HNMR (300 MHZ, D$_2$O, ppm) 8.34 (s, 1H), 8.29 (d, J=6.3, 1H), 7.60 (d, J=6.3, 1H), 6.13-6.18 (m, 2H), 5.30-5.38 (m, 2H), 4.31 (t, J=7.2, 4H), 2.37 (s, 3H), 2.25 (s, 3H), 2.05 (q, J=7.2, 4H), 1.81 (p, J=7.5, 4H), 1.24 (p, J=7.5, 4H). CNMR, 158.66, 142.37, 140.71, 138.65, 132.25, 128.23, 124.07, 60.80, 30.11, 26.31, 25.42, 19.69, 16.34.

Example 9

Synthesis of Compound cis-cis-N,N'-(dodeca-5,7-diene-1,12-diyl)-bis-(3,5-dimethyl-pyridinium) dibromide cis-cis-1,12-Dibromo-dodeca-5,7-diene was added to a solution of 3, 5-lutidine (3 mmol) in acetonitrile and the solution refluxed for 24 hours. The acetonitrile was removed in vacuum and the resulting residue was partitioned between ether and water. The aqueous layer was washed extensively with ether until no 3, 5-lutidine left in the aqueous layer. The resulting aqueous solution of the product was lyophilized to yield the pure product. (75%). $^1$HNMR (300 MHZ, D$_2$O, ppm) 8.29 (s, 4H), 7.99 (s, 2H), 6.12-6.18 (m, 2H), 5.30-5.38 (m, 2H), 4.31 (t, J=7.5, 4H), 2.30 (s, 6H), 2.05 (q, J=7.2, 4H), 1.81 (p, J=7.5, 4H), 1.24 (p, J-7.5, 4H). CNMR, 146.56, 140.96, 139.11, 132.28, 124.09, 61.49, 30.21, 26.34, 25.43, 17.73.

Example 10

Synthesis of Compound N,N'[1,4-phenylenedi-(4-butanyl)]-bis-[3-(2'-S-1-methyl-pyrrolidin-2-yl)-pyridinium] dibromide

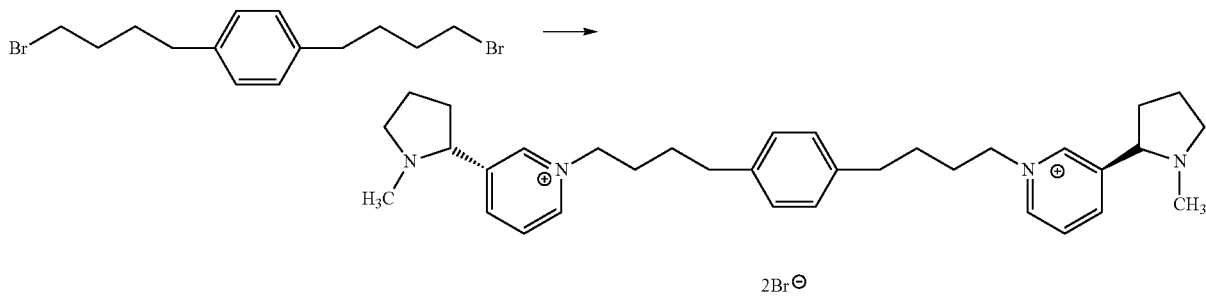

1,4-Bis-(4-bromo-butyl)-benzene was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$HNMR (300 MHZ, D$_2$O, ppm) 8.57-8.59 (m, 4H), 8.35 (d, J=8.1, 2H), 7.88 (dd, J=7.8, J=6.6, 2H), 7.01 (s, 4H), 4.45 (t, J=7.5, 4H), 3.40 (t, 2H), 3.04-3.10 (m, 2H), 2.49 (t, J=7.5, 4H), 2.30-2.40 (m, 2H), 2.18-2.29 (m, 2H), 2.03 (s, 6H), 1.80-1.90 (m, 8H), 1.40-1.55 (m, 4H). CNMR, 144.65, 143.48, 143.30, 139.76, 128.74, 128.42, 67.61, 61.99, 56.62, 39.37, 33.96, 33.73, 30.17, 27.28, 22.33.

Example 11

Synthesis of Compound N,N'[1,4-phenylenedi-(4-butanyl)]-bis-(2-methylpyridinium) dibromide

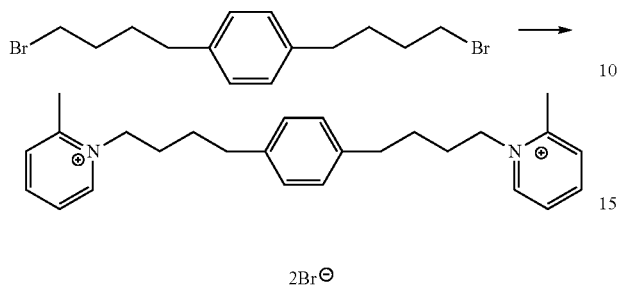

1,4-Bis-(4-bromo-butyl)-benzene was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$HNMR (300 MHZ, D$_2$O, ppm) 8.49 (dd, J=6.0, 1.2, 2H), 8.17 (dt, J=8.1, J=1.5, 2H), 7.70 (d, J=8.1, 2H), 7.65 (dt, J=8.1, J=1.2, 2H), 7.04 (s, 4H), 4.37 (t, J=7.2, 4H), 2.62 (s, 6H), 2.51 (t, J=7.2, 4H), 1.77 (p, J=7.8, 4H), 1.57 (p, J=7.8, 4H). CNMR. 145.05, 144.73, 139.79, 130.24, 128.78, 125.64, 58.02, 34.11, 29.01, 27.49, 19.70.

Example 12

Synthesis of Compound N,N'[1,4-phenylenedi-(4-butanyl)]-bis-(3-methylpyridinium) dibromide

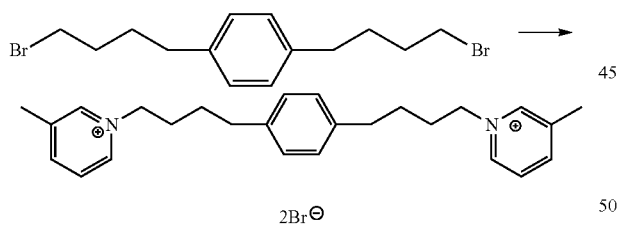

1,4-Bis-(4-bromo-butyl)-benzene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHZ, D$_2$O, ppm) 8.45 (s, 2H), 8.40 (d, J=6.6, 2H), 8.16 (d, J=8.1, 2H), 7.72 (dd, J=8.1, J=6.0, 2H), 7.00 (s, 4H), 4.37 (t, J=7.5, 4H), 2.47 (t, J=7.5, 4H), 2.34 (s, 6H), 1.82 (p, J=7.5, 4H), 1.46 (p, J=7.5, 4H). CNMR. 146.02, 143.68, 141.68, 139.96, 139.79, 128.75, 127.46, 61.69, 34.04, 30.14, 27.28, 17.90.

Example 13

Synthesis of Compound N,N'[1,4-phenylenedi-(4-butanyl)]-bis-(4-methylpyridinium) dibromide

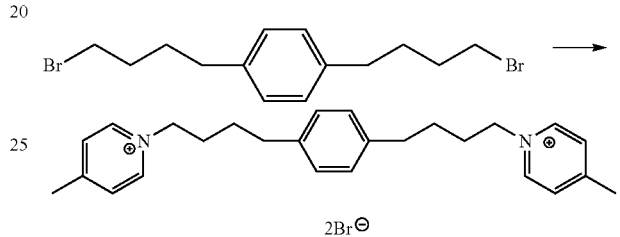

1,4-Bis-(4-bromo-butyl)-benzene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$HNMR (300 MHZ, D$_2$O, ppm) 8.38 (d, J-6.9, 4H), 7.64 (d, J=6.9, 4H), 6.98 (s, 4H), 4.33 (t, J=7.2, 4H), 2.46 (t, J=7.2, 4H), 2.44 (s, 6H), 1.81 (p, J=7.5, 4H), 1.45 (p, J=7.5, 4H). CNMR. 159.99, 143.04, 139.79, 128.74, 128.65, 60.99, 34.02, 30.03, 27.26, 21.50.

Example 14

Synthesis of Compound N,N'[1,4-phenylenedi-(4-butanyl)]-bis-(3-ethylpyridinium) dibromide

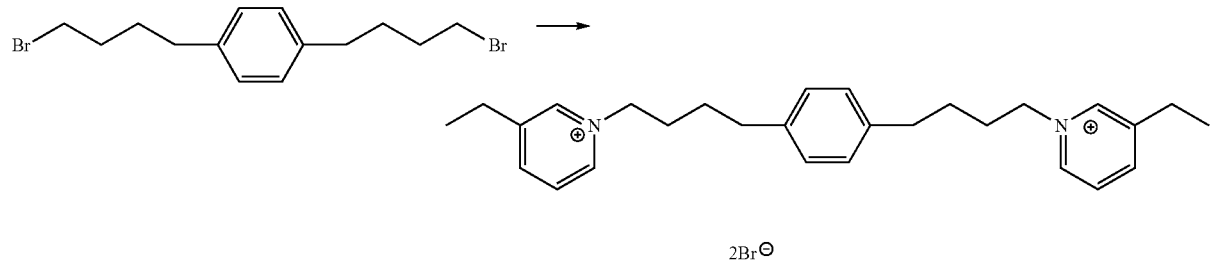

1,4-Bis-(4-bromo-butyl)-benzene was added to a solution of 3-ethylpyridine (3 mmol) in acetonitrile and the solution refluxed for 24 hours. The acetonitrile was removed in vacuum and the resulting residue was partitioned between ether and water. The aqueous layer was washed extensively with ether until no 3-ethylpyridine left in the aqueous layer. The resulting aqueous solution of the product was lyophilized to yield the pure product. (75%). $^1$HNMR (300 MHZ, D$_2$O, ppm) 8.45 (s, 2H), 8.41 (d, J=6.0, 2H), 8.19 (d, J=8.4, 2H), 7.73 (dd, J=8.1, J=6.0, 2H), 6.97 (s, 4H), 4.37 (t, J=7.2, 4H), 2.66 (q, 7.8, 2H), 2.49 (t, J-7.2, 1.83 (p, J=7.5, 4H), 1.45 (p, J-1.5, 4H), 1.09 (t, J=7.8, 6H). CNMR. 145.61, 145.08, 143.09, 141.51, 139.78, 128.75, 127.68, 61.70, 34.01, 30.13, 27.24, 25.70, 13.92.

Example 15

Synthesis of Compound N,N'[1,4-phenylenedi-(4-butanyl)]-bis-(5,6,7,8-tetrahydroquinolinium) dibromide

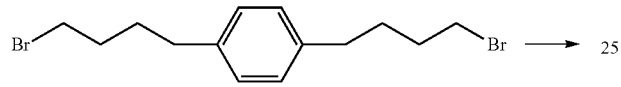

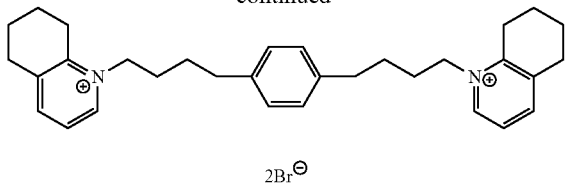

1,4-Bis-(4-bromo-butyl)-benzene was added to a solution of tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroquinoline left in the aqueous layer. The resulting aqueous solution of the product was lyophilized to yield the pure product. (75%). $^1$HNMR (300 MHZ, D$_2$O, ppm) 8.30 (d, J=6.3, 2H), 7.95 (d, J=7.8, 2H), 7.49 (dd, J=8.1, J=6.3, 2H), 7.02 (s, 4H), 4.28 (t, 7.5, 4H), 2.83 (t, J=7.5, 4H), 2.77 (t, J=7.5, 4H), 2.49 (t, J=7.5, 4H), 1.66-1.80 (m, 8H), 1.35-1.63 (m, 8H).

Example 16

Synthesis of Compound N,N'[1,4-phenylenedi-(4-butanyl)]-bis-(5,6,7,8-tetrahydroisoquinolinium) dibromide

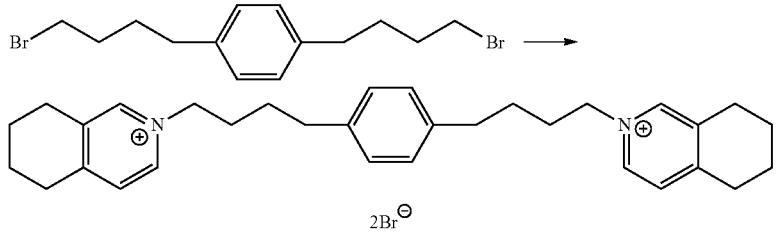

1,4-Bis-(4-bromo-butyl)-benzene was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). $^1$HNMR (300 MHZ, D$_2$O, ppm) 8.21 (s, 2H), 8.13 (d, J=6.3, 2H), 7.46 (d, J=6.3, 2H), 6.96 (s, 4H), 4.25 (t, J=7.2, 4H), 2.2.78-2.84 (br, 4H), 2.63-2.70 (br, 4H), 2.44 (t, J=7.2, 4H), 1.78 (p, J=7.5, 4H), 1.64-1.70 (m, 8H), 1.42 (p, J=7.5, 4H). CNMR, 158.77, 143.03, 139.78, 139.56, 138.88, 128.72, 127.84, 60.79, 49.11, 34.01, 29.91, 29.31, 27.16, 26.16, 20.99.

Example 17

Synthesis of Compound N,N'[1,4-phenylenedi-(4-butanyl)]-bis-[3-(3-hydroxy-propyl)-pyridinium] dibromide

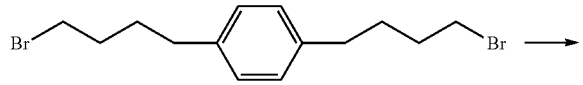

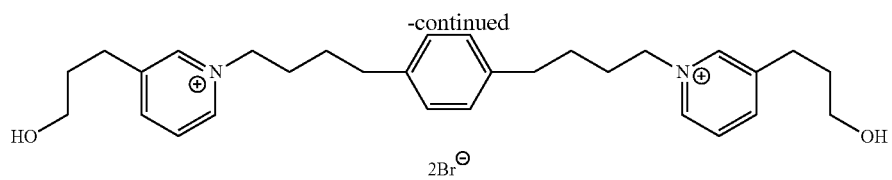

1,4-Bis-(4-bromo-butyl)-benzene was added to a solution of {3-hydroxy-propyl)-pyridine (3 mmol) in acetonitrile and the solution refluxed for 24 hours. The acetonitrile was removed in vacuum and the resulting residue was partitioned between ether and water. The aqueous layer was washed extensively with ether until no (3-hydroxy-propyl)-pyridine left in the aqueous layer. The resulting aqueous solution of the product was lyophilized to yield the pure product. (75%). $^1$HNMR (300 MHZ, D$_2$O, ppm) 8.49 (s, 2H), 8.43 (d, J=6.0, 2H), 8.22 (d, J=8.1, 2H), 7.75 (dd, J=7.8, J=6.0, 2H), 6.98 (s, 4H), 4.38 (t, J=7.2, 4H), 3.45 (t, J=6.6, 4H), 2.72 (t, J=7.8, 4H), 2.46 (t, J=7.5, 4H), 1.83 (p, J-7.5, 4H), 1.70-1.75)m, 4H), 1.44 (p, J-7.5, 4H). CNMR, 145.53, 143.51, 141.78, 139.78, 128.75, 127.78, 61.75, 60.67, 34.01, 32.17, 30.13, 28.81, 27.24.

Example 18

Synthesis of Compound N,N'[1,4-phenylenedi-(4-butanyl)]-bis-(2,4-dimethylpyridinium) dibromide

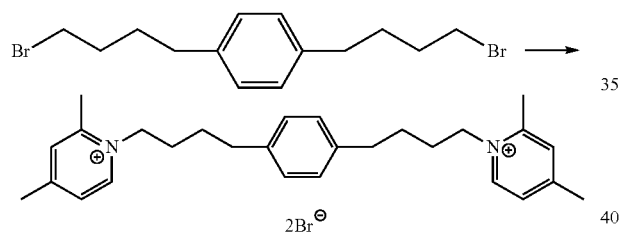

1,4-Bis-(4-bromo-butyl)-benzene was added to a solution of 2,4-lutidine (3 mmol) in acetonitrile and the solution refluxed for 24 hours. The acetonitrile was removed in vacuum and the resulting residue was partitioned between ether and water. The aqueous layer was washed extensively with ether until no 2,4-lutidine left in the aqueous layer. The resulting aqueous solution of the product was lyophilized to yield the pure product. (75%). $^1$HNMR (300 MHZ, D$_2$O, ppm) 8.27 (d, J=6.6, 2H), 7.50 (s, 2H), 7.45 (d, J=6.6, 2H), 7.02 (s, 4H), 4.28 (t, J=7.2, 4H), 2.52 (s, 6H), 2.48 (t, J=7.2, 4H), 2.38 (s, 6H), 2.20 (s, 3H), 1.79 (p, J=7.5, 4H), 1.42 (p, J=7.5, 4H).

Example 19

Synthesis of Compound N,N'[1,4-phenylenedi-(4-butanyl)]-bis-(3,4-dimethylpyridinium) dibromide [ZZ 1 81]

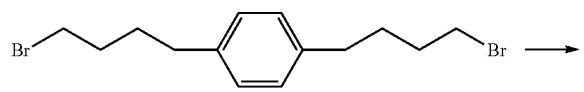

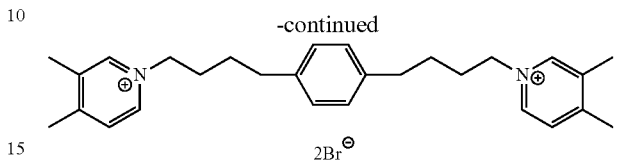

1,4-Bis-(4-bromo-butyl)-benzene was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$HNMR (300 MHZ, D$_2$O, ppm) 8.25 (s, 2H), 8.22 (d, J-6.0, 2H), 7.55 (d, J=6.0, 2H), 6.96 (s, 4H), 4.27 (t, J=7.2, 4H), 2.45 (t, J=7.2, 4H), 2.34 (s, 6H), 2.21 (s, 6H), 1.79 (p, J=7.5, 4H), 1.42 (p, J=7.5, 4H). CNMR, 158.64, 142.28, 140.66, 139.78, 138.61, 128.72, 128.18, 34.02, 29.94, 27.20, 19.67, 16.29.

Example 20

Synthesis of Compound N,N'[1,4-phenylenedi-(4-butanyl)]-bis-(3,5-dimethylpyridinium) dibromide [ZZ 1 82]

1,4-Bis-(4-bromo-butyl)-benzene was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHZ, D$_2$O, ppm) 8.23 (s, 4H), 7.97 (s, 2H), 6.97 (s, 4H), 4.29 (t, J=7.2, 4H), 2.45 (t, J=7.2, 4H), 2.27 (s, 12H), 1.81 (p, J=7.5, 4H), 1.45 (p, J=7.5, CNMR, 146.50, 140.89, 139.79, 139.04, 128.74, 63.46, 34.04, 30.03, 27.22, 17.70.

Example 21

Synthesis of Compound 5-[2-(5-hydroxy-pent-1-ynyl)-phenyl]-pent-4-yn-1-ol

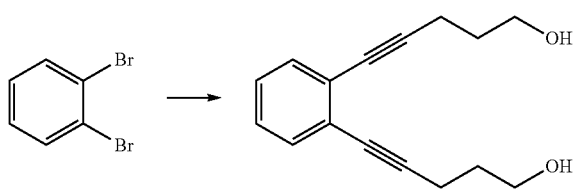 [SMILES: Brc1ccccc1Br ; OCCCC#Cc1ccccc1C#CCCCO]

1,2-Dibromobenzene (10.94 g, 46.37 mmol), 4-pentyn-1-ol (9.36 g, 111.30 mmol), and bis(triphenylphosphine)palladium(II) dichloride (650 mg, 0.93 mmol) was stirred in triethylamine (150 mL) under nitrogen for 5 min. Copper(I) iodide (88 mg, 0.46 mmol) was added and the mixture was stirred for 4 hrs at 85° C. for 6 days. The mixture was cooled to room temperature and filtered through a celite pad, rinsed with ethylacetate. The combined filtrate was evaporated to dryness under reduced pressure. The resulting residue was purified by column chromatography (chloroform:methanol 30:1) to afford 5.33 g of the title compound. Yield: 47%. $^1$H NMR (300 MHZ, D$_2$O, ppm) δ 1.85 (m, 4H), 2.58 (t, J=6.6 Hz, 4H), 3.82 (t, J=6.0 Hz, 4H), 7.18 (m, 2H), 7.36 (m, 2H) ppm; $^{13}$C NMR (75 MHz, CDCl$_3$) δ 16.3, 31.4, 62.4, 80.2, 93.3, 126.0, 127.4, 131.8 ppm.

Example 22

Synthesis of Compound 1,2-bis-(5-bromo-pent-1-ynyl)-benzene

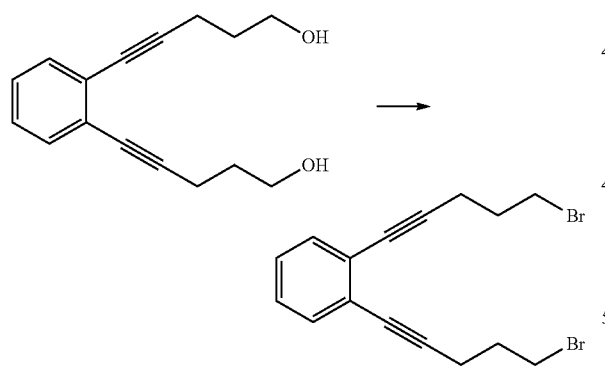

5-[2-(5-Hydroxy-pent-1-ynyl)-phenyl]-pent-4-yn-1-ol (2.40 g, 9.90 mmol) and carbon tetrabromide (8.21 g, 24.75 mmol) were dissolved in dry methylene chloride (30 mL) and cooled to 0° C. Triphenyl phosphine (6.82 g, 25.99 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (1/4). The combined organic solvents were evaporated to dryness under reduced pressure. The resulting residue was purified by column chromatography (hexanes:ethylacetate 30:1) to afford 2.48 g of the title compound. Yield: 68%. $^1$H NMR (300 MHz, CDCl$_3$) δ 2.16 (m, 4H), 2.68 (t, J=6.6 Hz, 4H), 3.65 (dt, J=6.6, 0.6 Hz, 4H), 7.20 (m, 2H), 7.38 (m, 2H) ppm; $^{13}$C NMR (75 MHz, CDCl$_3$) δ 18.6, 31.8, 32.7, 80.7, 91.8, 125.9, 127.6, 131.9 ppm.

Example 23

Synthesis of Compound 1,2-bis-[5-(2-methyl-pyridinium)-pent-1-ynyl]-benzene dibromide

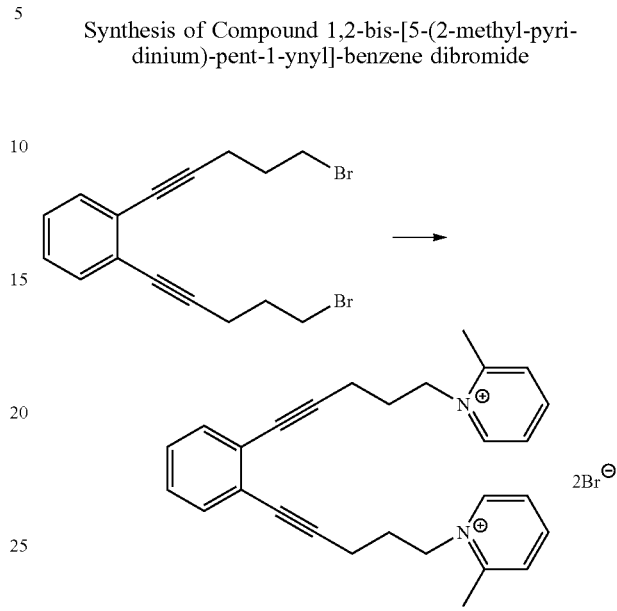

A mixture of 1,2-bis-(5-bromo-pent-1-ynyl)-benzene (264 mg, 0.72 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 327 mg of the title compound. Yield: 82%. $^1$H NMR (300 MHz, CD$_3$OD) δ 2.35 (m, 4H), 2.81 (t, J=6.6 Hz, 4H), 3.02 (s, 6H), 4.91 (t, J=7.5 Hz, 4H)," 7.27-7.50 (m, 4H), 7.92-8.15 (m, 4H), 8.45 (t, J=7.8 Hz, 2H), 9.11 (d, J=6.3 Hz, 2H) ppm; $^{13}$C NMR (75 MHz, CD$_3$OD) δ 17.6, 21.1, 30.1, 58.2, 81.9, 92.9, 126.4, 127.0, 129.2, 129.3, 131.5, 133.1, 146.4, 156.7 ppm.

Example 24

Synthesis of Compound 1,2-bis-[5-(3-methyl-pyridinium)-pent-1-ynyl]-benzene dibromide

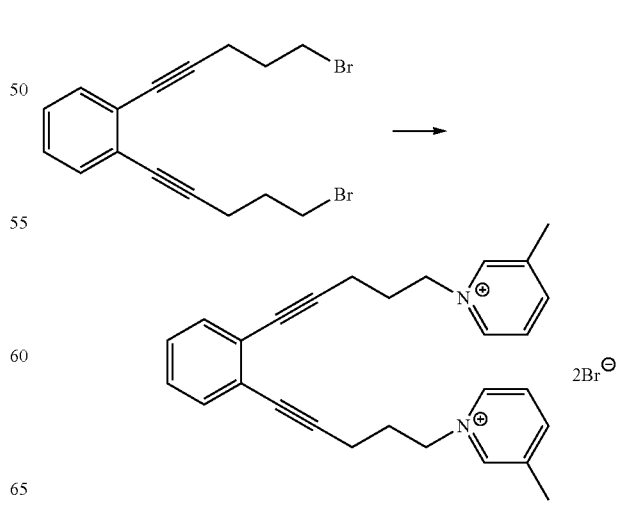

A mixture of 1,2-bis-(5-bromo-pent-1-ynyl)-benzene (270 mg, 0.73 mmol) and 3-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 350 mg of the title compound. Yield: 86%. $^1$H NMR (300 MHz, CD$_3$OD) δ 2.45 (m, 4H), 2.56 (s, 6H) 2.78 (t, J=6.6 Hz, 4H), 4.95 (t, J=7.2 Hz, 4H), 7.22-7.42 (m, 4H), 8.05 (dd, J=8.1, 6.0 Hz, 2H), 8.39 (d, J=7.8 Hz, 2H), 9.10 (d, J=6.0 Hz, 2H), 9.19 (s, 2H) ppm; $^{13}$C NMR (75 MHz, CD$_3$OD) δ 17.6, 18.9, 31.2, 61.9, 81.6, 92.8, 126.4, 128.7, 129.0, 132.9, 140.9, 143.1, 145.6, 147.3 ppm.

Example 25

Synthesis of Compound 1,2-bis-[5-(4-methyl-pyridinium)-pent-1-ynyl]-benzene dibromide

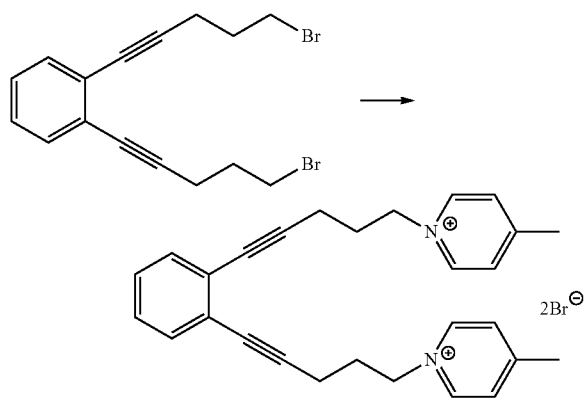

A mixture of 1,2-bis-(5-bromo-pent-1-ynyl)-benzene (268 mg, 0.73 mmol) and 4-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 435 mg of the title compound. Yield: 86%. $^1$H NMR (300 MHz, CD$_3$OD) δ 2.41 (m, 4H), 2.51 (s, 6H), 2.78 (t, J=6.6 Hz, 4H), 4.91 (t, J=6.6 Hz, 4H), 7.30 (s, 4H), 7.92 (d, J=6.3 Hz, 4H), 9.05 (d, J=6.3 Hz, 4H) ppm; $^{13}$C NMR (75 MHz, CD$_3$OD) δ 17.5, 22.3, 31.0, 61.4, 81.5, 92.8, 126.4, 129.0, 129.8, 132.9, 144.9, 161.1 ppm.

Example 26

Synthesis of Compound 1,2-bis-[5-(2,4-dimethyl-pyridinium)-pent-1-ynyl]-benzene dibromide

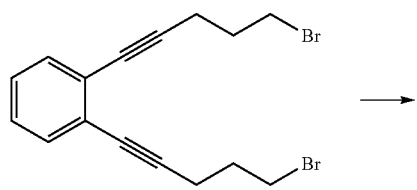

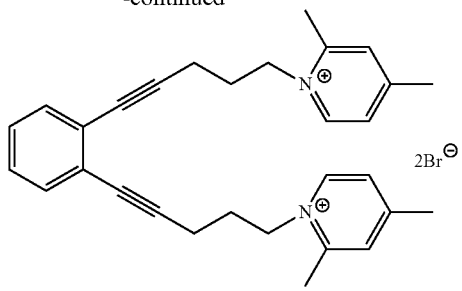

A mixture of 1,2-bis-(5-bromo-pent-1-ynyl)-benzene (268 mg, 0.73 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 343 mg of the title compound. Yield: 81%. $^1$H NMR (300 MHz, CD$_3$OD) δ 2.34 (m, 4H), 2.52 (s, 3H), 2.84 (t, J=6.6 Hz, 4H), 2.97 (s, 3H), 4.87 (t, J=7.5 Hz, 4H), 7.27-7.45 (m, 4H), 7.80 (d, J=6.3 Hz, 2H), 7.87 (s, 2H), 8.99 (d, J=6.3 Hz, 2H) ppm; $^{13}$C NMR (75 MHz, CD$_3$OD) δ 17.6, 20.9, 22.0, 30.1, 57.5, 81.6, 93.0, 126.4, 127.6, 129.1, 131.7, 133.0, 145.5, 155.5, 160.3 ppm.

Example 27

Synthesis of Compound 1,2-bis-[5-(3,4-dimethyl-pyridinium)-pent-1-ynyl]-benzene dibromide [GZ 581 B]

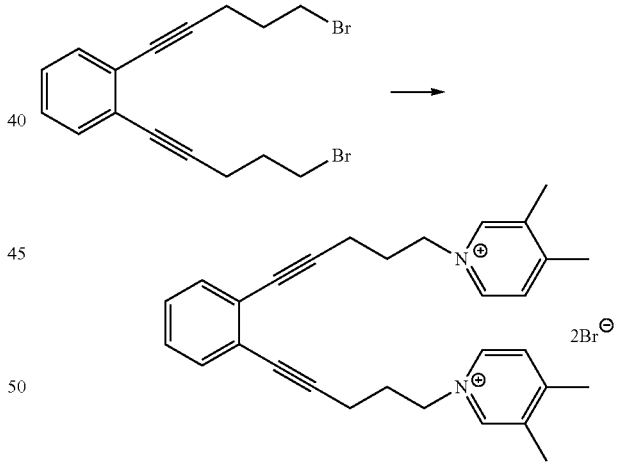

A mixture of 1,2-bis-(5-bromo-pent-1-ynyl)-benzene (276 mg, 0.75 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 355 mg of the title compound. Yield: 81%. $^1$H NMR (300 MHz, CD$_3$OD) δ 2.37 (s, 3H), 2.40 (s, 3H), 2.44 (m, 4H), 2.79 (t, J=6.6 Hz, 4H), 4.88 (t, J=6.6 Hz, 4H), 7.29 (s, 4H), 7.86 (d, J=6.3 Hz, 2H), 8.95 (d, J=6.3 Hz, 2H), 9.06 (s, 2H), ppm; $^{13}$C NMR (75 MHz, CD$_3$OD) δ 17.3, 17.7, 20.4, 31.1, 61.2, 81.3, 93.0, 126.5, 129.0, 129.4, 132.8, 139.5, 142.7, 144.3, 159.8 ppm.

Example 28

Synthesis of Compound 1,2-bis-[5-(3,5-dimethyl-pyridinium)-pent-1-ynyl]-benzene dibromide [GZ 581 A]

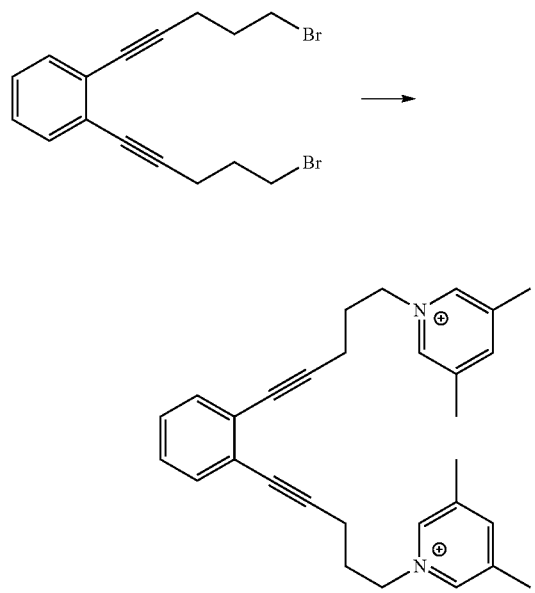

A mixture of 1,2-bis-(5-bromo-pent-1-ynyl)-benzene (280 mg, 0.76 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 363 mg of the title compound. Yield: 82%. $^1$H NMR (300 MHz, CD$_3$OD) δ 2.42 (m, 4H), 2.51 (s, 6H), 2.76 (t, J=6.9 Hz, 4H), 4.86 (t, J=6.9 Hz, 4H), 7.30 (m, 4H), 8.13 (s, 2H), 8.95 (s, 4H) ppm; $^{13}$C NMR (75 MHz, CD$_3$OD) δ 17.7, 18.7, 31.2, 61.9, 81.6, 92.9, 126.6, 129.0, 132.8, 140.2, 142.9, 147.9 ppm.

Example 29

Synthesis of Compound 1,2-bis-[5-quinolinium-pent-1-ynyl)-benzene dibromide

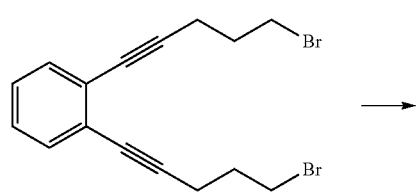

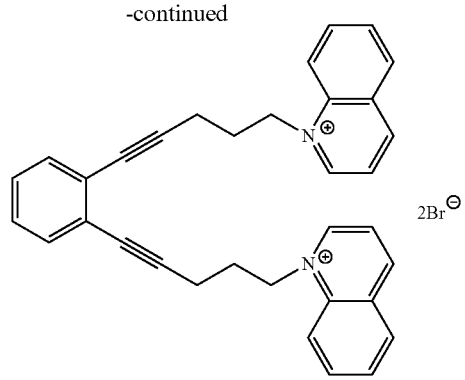

A mixture of 1,2-bis-(5-bromo-pent-1-ynyl)-benzene (249 mg, 0.68 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 317 mg of the title compound. Yield: 75%. $^1$H NMR (300 MHz, CD$_3$OD) δ 2.42 (m, 4H), 2.78 (t, J=6.6 Hz, 4H), 5.36 (t, J=6.9 Hz, 4H), 7.02-7.28 (m, 4H), 7.97 (t, J=7.5 Hz, 2H), 8.07-8.40 (m, 4H), 8.67 (d, J=9.0 Hz, 2H), 9.15 (d, J=8.4 Hz, 2H), 9.15 (d, J=8.4 Hz, 2H), 9.70 (d, J=5.7 Hz, 2H) ppm; $^{13}$C NMR (75 MHz, CD$_3$OD) δ 17.8, 29.8, 58.5, 81.6, 92.9, 119.7, 123.2, 126.2, 129.0, 130.5, 131.3, 132.0, 132.7, 137.2, 139.0, 149.0, 150.6 ppm.

Example 30

Synthesis of Compound 1,2-bis-[5-isoquinolinium-pent-1-ynyl)-benzene dibromide [GZ 582 B]

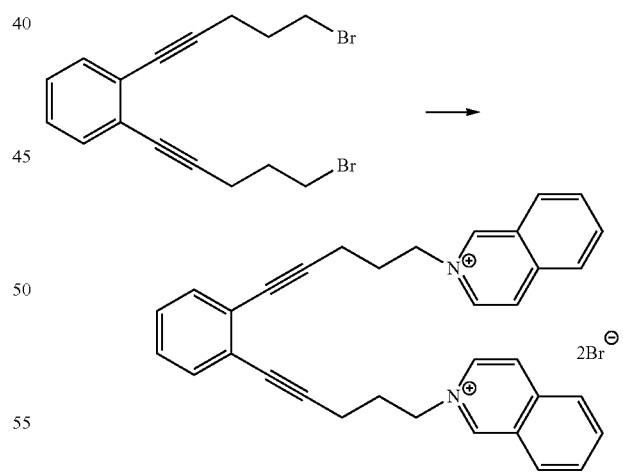

A mixture of 1,2-bis-(5-bromo-pent-1-ynyl)-benzene (252 mg, 0.68 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 319 mg of the title compound. Yield: 74%. $^1$H NMR (300 MHz, CD$_3$OD) δ 2.46 (m, 4H), 2.77 (t, J=6.3 Hz, 4H), 5.01 (t, J=6.6 Hz, 4H), 6.91 (m, 2H), 7.04 (m, 2H), 7.90-8.50 (m, 10H), 8.78

(d, J=6.9 Hz, 2H), 10.10 (s, 2H) ppm; $^{13}$C NMR (75 MHz, CD$_3$OD) δ 17.8, 30.8, 62.1, 81.3, 92.7, 125.7, 127.3, 128.1, 128.5, 131.2, 131.4, 132.1, 132.2, 135.6, 137.9, 138.4, 150.8 ppm.

Example 31

Synthesis of Compound 1,2-bis-[5-(2'-S-nicotinium-pent-1-ynyl)]benzene dibromide

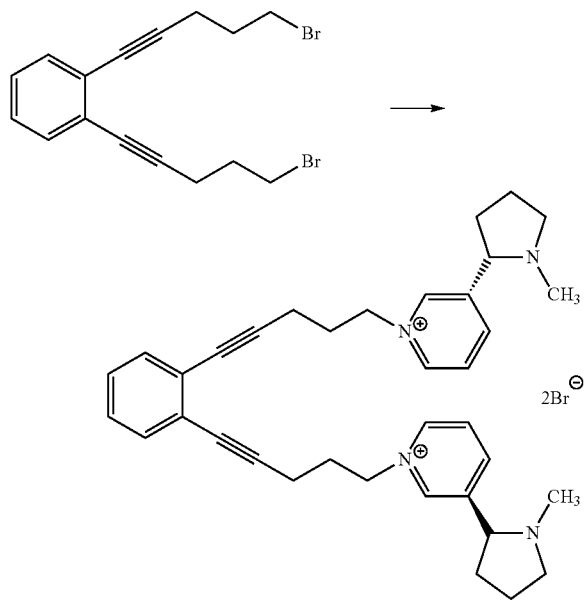

A mixture of 1,2-bis-(5-bromo-pent-1-ynyl)-benzene (330 mg, 0.90 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 340 mg of the title compound. Yield: 55%. $^1$H NMR (300 MHz, CD$_3$OD) δ 2.00-2.82 (m, 16H), 2.55 (s, 6H), 2.90 (m, 2H), 3.55 (m, 2H), 4.17 (m, 2H), 4.95 (t, J=6.9 Hz, 4H), 7.27 (m, 2H), 7.37 (m, 2H), 8.17 (dd, J=7.8, 6.3 Hz, 2H), 8.69 (d, J=8.4 Hz, 2H), 9.15 (d, J=6.0 Hz, 2H), 9.40 (s, 2H) ppm; $^{13}$C NMR (75 MHz, CD$_3$OD) δ 17.5, 23.5, 30.9, 34.1, 40.3, 57.6, 62.4, 68.7, 81.9, 92.7, 126.4, 129.1, 129.6, 133.0, 141.1, 145.8, 146.0, 146.5 ppm.

Example 32

Synthesis of Compound 5-[2-(5-hydroxy-pentyl)-phenyl]-pentan-1-ol

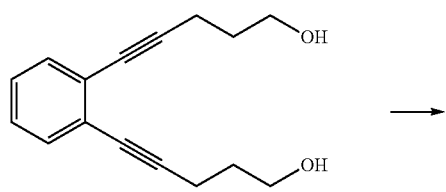

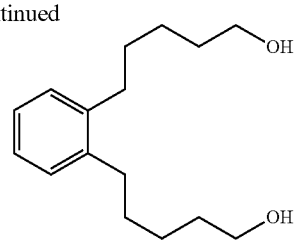

5-[2-(5-Hydroxy-pent-1-ynyl)-phenyl]-pent-4-yn-1-ol (2.70 g, 11.14 mmol) was dissolved in ethanol (30 mL) and 10% Pd/C (2.5% w/w) was added. The resulting mixture was hydrogenated on a Parr hydrogenation apparatus (45 psi) for 4 hrs. The catalyst was removed by filtration through a Celite pad. The filter cake was rinsed with methanol, and the combined organic liquors were concentrated under reduced pressure. The crude product was purified by column chromatography (chloroform:methanol 20:1) to afford 2.55 g of the title compound. Yield: 91%. $^1$H NMR (300 MHz, CDCl$_3$) δ 1.38-1.67 (m, 12H), 2.60 (t, J=7.8 Hz, 4H), 3.59 (t, J=6.6 Hz, 4H), 7.11 (m, 4H) ppm; $^{13}$C NMR (75 MHz, CDCl$_3$) δ 26.0, 31.3, 32.6, 32.8, 62.6, 125.8, 129.1, 140.2 ppm.

Example 33

Synthesis of Compound 1,2-bis-[5-bromo-pentyl)-benzene

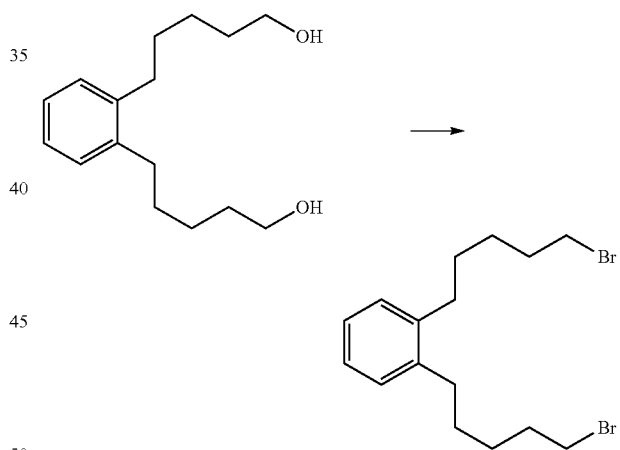

5-[2-(5-Hydroxy-penty])-phenyl]-pentan-1-ol (2.50 g, 10.00 mmol) and carbon tetrabromide (8.29 g, 25.00 mmol) were dissolved in dry methylene chloride (30 mL) and cooled to 0° C. Triphenyl phosphine (6.88 g, 26.25 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (3/4). The combined organic solvents were evaporated to dryness under reduced pressure. The resulting residue was purified by column chromatography (hexanes:ethylacetate30:1) to afford 3.76 g of the title compound. Yield: 99%. $^1$H NMR (300 MHz, CDCl$_3$) δ 1.47-1.73 (m, 8H), 1.91 (m, 4H), 2.63 (t, J=7.8 Hz, 4H), 3.42 (t, J=6.9 Hz, 4H), 7.15 (s, 4H) ppm; $^{13}$C NMR (75 MHz, CDCl$_3$) δ 28.5, 30.6, 32.7, 32.9, 34.0, 126.0, 129.2, 139.9 ppm.

Example 34

Synthesis of Compound 1,2-bis-[5-(2-methyl-pyridinium)-pentyl]-benzene dibromide

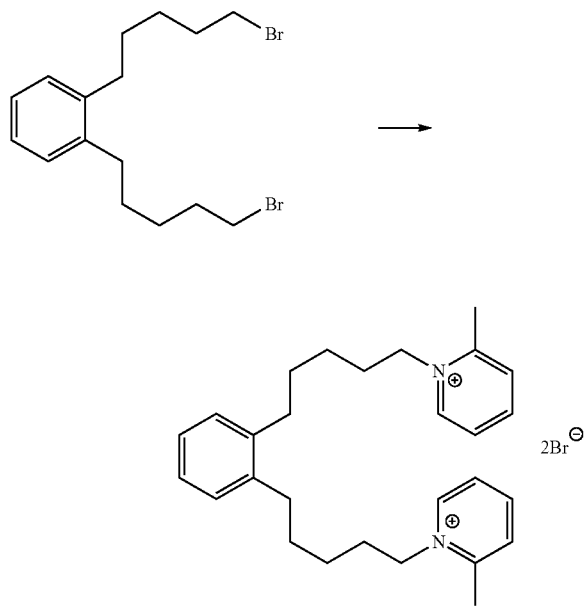

A mixture of 1,2-bis-(5-bromo-pentyl)-benzene (280 mg, 0.74 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 400 mg of the title compound. Yield: 95%. $^1$H NMR (300 MHz, CD$_3$OD) δ 1.54 (m, 4H), 1.68 (m, 4H), 2.01 (m, 4H), 2.69 (t, J=7.5 Hz, 4H), 2.90 (s, 6H), 4.61 (t, J=7.8 Hz, 4H), 7.02-7.19 (m, 4H), 7.92 (t, J=6.6 Hz, 2H), 8.00 (d, J=7.8 Hz, 2H), 8.44 (dt, J=7.8, 1.2 Hz, 2H), 8.93 (dd, J=6.3, 1.2 Hz, 2H) ppm; $^{13}$C NMR (75 MHz, CD$_3$OD) δ 20.8, 27.4, 31.2, 32.0, 33.4, 59.3, 126.9, 127.0, 130.3, 131.5, 141.0, 146.3, 146.4, 156.6 ppm.

Example 35

Synthesis of Compound 1,2-bis-[5-(3-methyl-pyridinium)-pentyl]-benzene dibromide

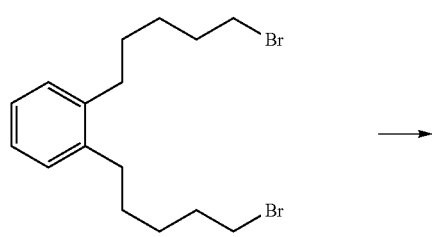

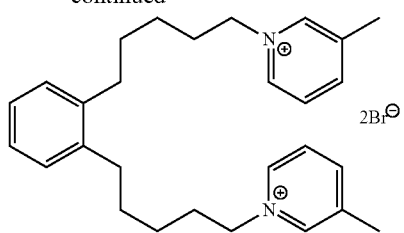

A mixture of 1,2-bis-(5-bromo-pentyl)-benzene (296 mg, 0.79 mmol) and 3-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 382 mg of the title compound. Yield: 86%. $^1$H NMR (300 MHz, CD$_3$OD) δ 1.47 (m, 4H), 1.66 (m, 4H), 2.08 (m, 4H), 2.59 (s, 6H), 2.65 (t, J=7.5 Hz, 4H), 4.64 (t, J=7.5 Hz, 4H), 7.01-7.19 (m, 4H), 7.99 (d, J=7.5, 6.0 Hz, 2H), 8.43 (dd, J=8.1, 0.6 Hz, 2H), 8.86 (d, J=6.0 Hz, 2H), 8.96 (s, 2H) ppm; $^{13}$C NMR (75 MHz, CD$_3$OD) δ 18.7, 27.2, 32.0, 32.6, 33.5, 62.9, 127.1, 128.7, 130.3, 141.0, 141.2, 143.1, 145.5, 147.2 ppm.

Example 36

Synthesis of Compound 1,2-bis-[5-(4-methyl-pyridinium)-pentyl]-benzene dibromide

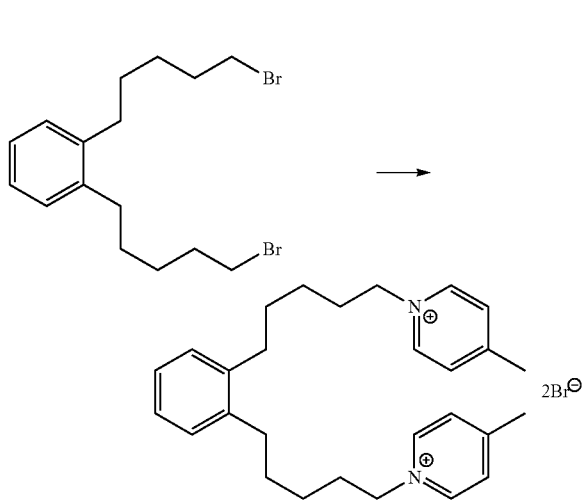

A mixture of 1,2-bis-(5-bromo-pentyl)-benzene (290 mg, 0.77 mmol) and 4-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 387 mg of the title compound. Yield: 89%. $^1$H NMR (300 MHz, CD$_3$OD) δ 1.44 (m, 4H), 1.65 (m, 4H), 2.04 (m, 4H), 2.64 (t, J=7.5 Hz, 4H), 2.68 (s, 6H), 4.58 (t, J=7.5 Hz, 4H), 7.02-7.15 (m, 4H), 7.92 (d, J=6.3 Hz, 4H), 8.83 (dd, J=5.1, 1.8 Hz, 4H) ppm; $^{13}$C NMR (75 MHz, CD$_3$OD) δ 22.3, 27.0, 31.9, 32.3, 33.3, 62.0, 127.0, 129.8, 130.2, 140.9, 144.7, 160.8 ppm.

Example 37

Synthesis of Compound 1,2-bis-[5-(2,4-dimethyl-pyridinium)-pentyl]-benzene dibromide

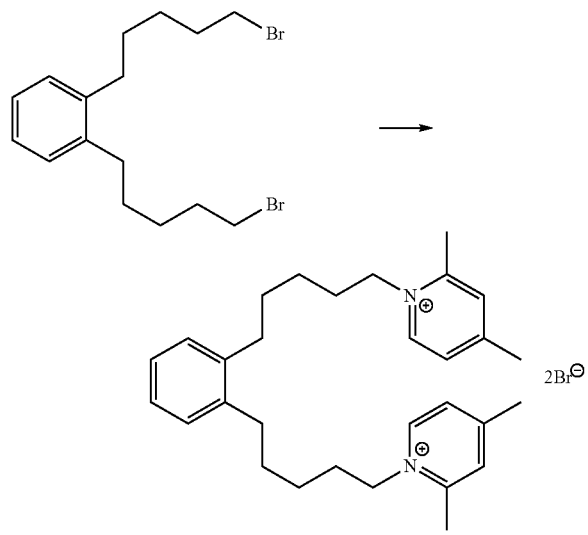

A mixture of 1,2-bis-(5-bromo-pentyl)-benzene (270 mg, 0.72 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 355 mg of the title compound. Yield: 84%. $^1$H NMR (300 MHz, CD$_3$OD) δ 1.52 (m, 4H), 1.68 (m, 4H), 2.01 (m, 4H), 2.61 (s, 6H), 2.68 (t, J=7.5 Hz, 4H), 2.82 (s, 6H), 4.53 (t, J=7.8 Hz, 4H), 7.02-7.19 (m, 4H), 7.73 (dd, J=6.3, 1.2 Hz, 2H), 7.82 (d, J-1.5 Hz, 2H), 8.72 (d, J=6.3 Hz, 2H) ppm; $^{13}$C NMR (75 MHz, CD$_3$OD) δ 20.5, 22.0, 27.4, 31.2, 32.0, 33.4, 58.4, 127.0, 127.6, 130.3, 131.6, 141.0, 145.4, 155.2, 160.2 ppm.

Example 38

Synthesis of Compound 1,2-bis-[5-(3,4-dimethyl-pyridinium)-pentyl]-benzene dibromide [GZ 584 B]

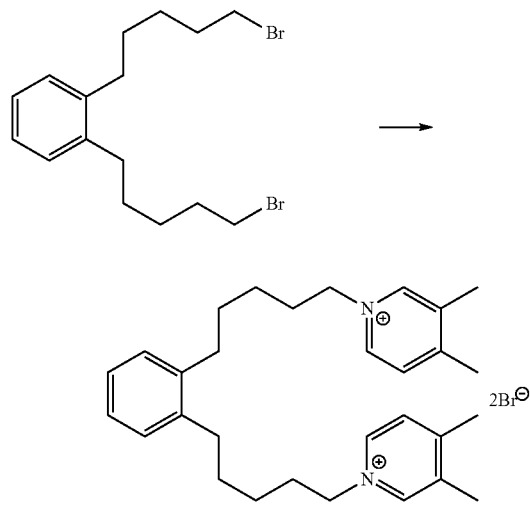 [SMILES: BrCCCCCc1ccccc1CCCCCBr ; Cc1cc[n+](CCCCCc2ccccc2CCCCC[n+]2ccc(C)c(C)c2)cc1C]

A mixture of 1,2-bis-(5-bromo-pentyl)-benzene (270 mg, 0.72 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 329 mg of the title compound. Yield: 78 $^1$H NMR (300 MHz, CD$_3$OD) δ 1.43 (m, 4H), 1.65 (m, 4H), 2.03 (m, 4H), 2.48 (s, 6H), 2.59 (s, 6H), 2.64 (t, J=7.5 Hz, 4H), 4.54 (t, J=7.5 Hz, 4H), 7.02-7.17 (m, 4H), 7.85 (d, J=6.3 Hz, 2H), 8.67 (d, J=4.8 Hz, 2H), 8.77 (s, 2H) ppm; $^{13}$C NMR (75 MHz, CD$_3$OD) δ 17.3, 20.6, 27.1, 31.9, 32.4, 33.3, 61.8, 126.9, 129.4, 130.2, 139.7, 140.9, 142.4, 144.0, 159.5 ppm.

Example 39

Synthesis of Compound 1,2-bis-[5-(3,5-dimethyl-pyridinium)-pentyl]-benzene dibromide [GZ 584 A]

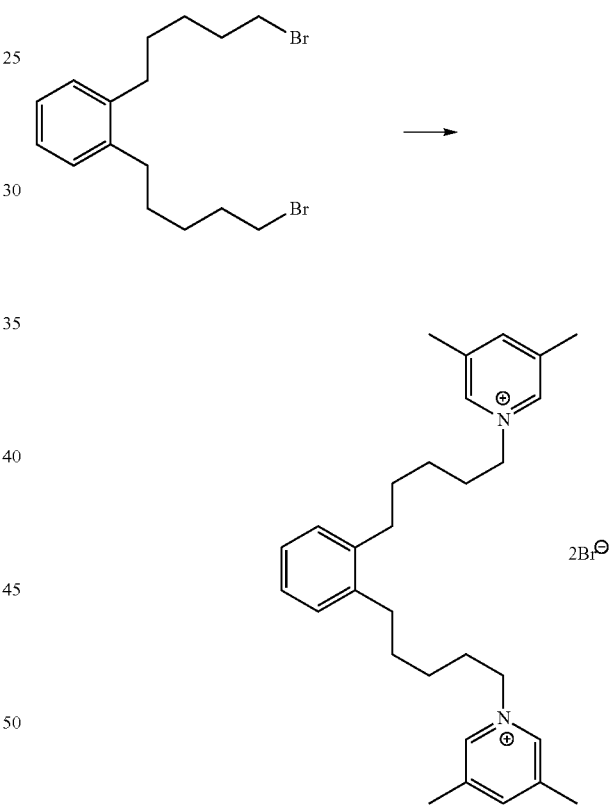

A mixture of 1,2-bis-(5-bromo-pentyl)-benzene (290 mg, 0.77 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 321 mg of the title compound. Yield: 71%. $^1$H NMR (300 MHz, CD$_3$OD) δ 1.50 (m, 4H), 1.65 (m, 4H), 2.12 (m, 4H), 2.58 (s, 12H), 2.64 (t, J=6.3 Hz, 4H), 4.68 (t, J=7.5 Hz, 4H), 7.02-7.19 (m, 4H), 8.33 (s, 2H), 8.91 (s, 4H) ppm; $^{13}$C NMR (75 MHz, CD$_3$OD) δ 18.7, 27.2, 31.9, 32.5, 33.4, 62.5, 126.9, 130.2, 140.0, 140.9, 142.6, 147.7 ppm.

Example 40

Synthesis of Compound 1,2-bis-[5-quinolinium-pentyl)-benzene dibromide

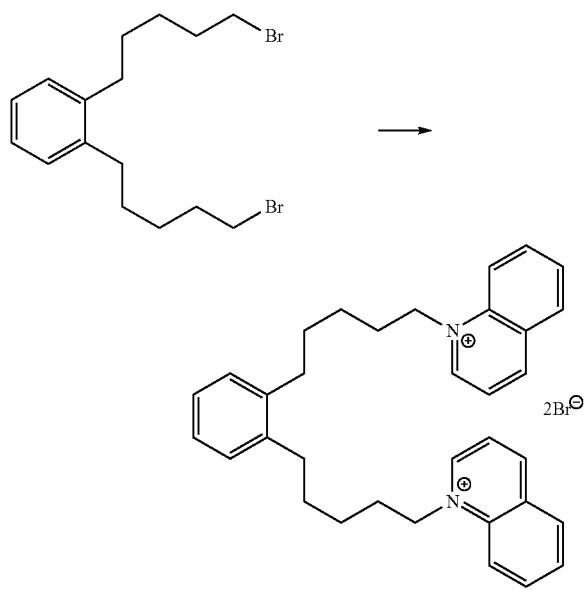

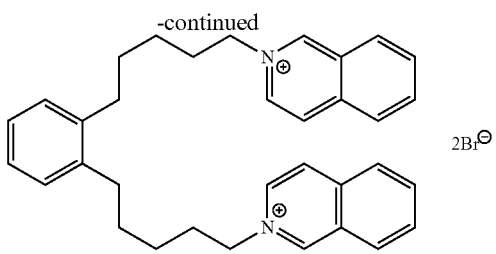

A mixture of 1,2-bis-(5-bromo-pentyl)-benzene (271 mg, 0.72 mmol) and isoquinoline (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 392 mg of the title compound. Yield: 86%. $^1$H NMR (300 MHz, CD$_3$OD) δ 1.38-1.70 (m, 8H), 2.20 (m, 4H), 2.52 (t, J=7.2 Hz, 4H), 4.92 (t, J=7.5 Hz, 4H), 6.83-7.05 (m, 4H), 7.99 (dd, J=6.9, 1.2 Hz, 2H), 8.18 (dt, J=8.1, 0.9, 2H), 8.28 (d, J=8.4 Hz, 2H), 8.45-8.60 (m, 4H), 8.84 (dd, J=6.9, 1.2 Hz, 2H), 10.21 (s, 2H) ppm; $^{13}$C NMR (75 MHz, CD$_3$OD) δ 27.0, 31.6, 32.2, 33.1, 62.5, 126.7, 127.2, 128.2, 128.5, 129.9, 131.2, 132.2, 135.6, 137.9, 138.3, 140.6, 150.3 ppm.

A mixture of 1,2-bis-(5-bromo-pentyl)-benzene (282 mg, 0.75 mmol) and quinoline (1 mL) was heated at 60-70° C. for 12 hrs. The resulted mixture was washed with diethyl ether and then dissolved in water (20 mL), the aqueous solution was extracted with chloroform (20 mL*3). Water was removed by lyophilization to afford 411 mg of the title compound. Yield: 86%. $^1$H NMR (300 MHz, CD$_3$OD) δ 1.41-1.73 (m, 8H), 2.13 (m, 4H), 2.47 (t, J=6.6 Hz, 4H), 5.22 (t, J=7.5 Hz, 4H), 6.91 (m, 4H), 8.00 (t, J=7.8 Hz, 2H), 8.16 (m, 2H), 8.31 (t, J=7.2 Hz, 2H), 8.44 (d, J=7.8 Hz, 2H), 8.65 (d, J=8.7 Hz, 2H), 9.30 (d, J=8.1 Hz, 2H), 9.70 (d, J=5.4 Hz, 2H) ppm; $^{13}$C NMR (75 MHz, CD$_3$OD) δ 27.3, 30.9, 31.6, 33.1, 59.2, 119.8, 123.0, 126.7, 129.8, 131.0, 131.1, 131.8, 137.1, 138.6, 140.6, 148.6, 150.2 ppm.

Example 41

Synthesis of Compound 1,2-bis-[5-isoquinolinium-pentyl)-benzene dibromide [GZ 585 B]

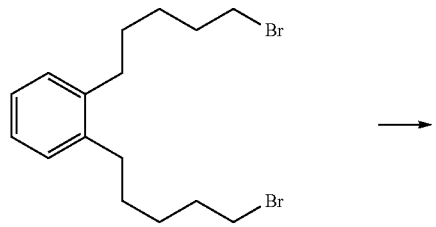

Example 42

Synthesis of Compound 1,2-bis-[5-(2'-S-nicotinium-pentyl)]benzene dibromide

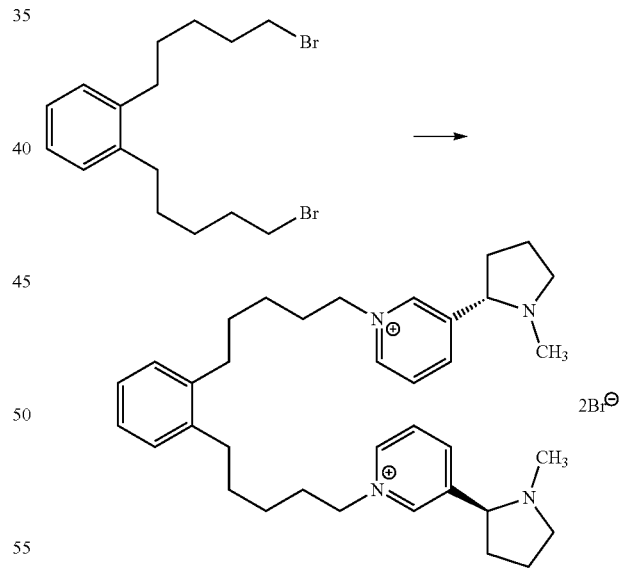

A mixture of 1,2-bis-(5-bromo-pentyl)-benzene (278 mg, 0.74 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3), Water was removed by lyophilization to afford 390 mg of the title compound. Yield: 75%. $^1$H NMR (300 MHz, CD$_3$OD) δ 1.40-1.75 (m, 8H), 2.08-2.45 (m, 10H), 2.67 (s, 6H), 2.55-2.75 (m, 8H), 3.07 (m, 2H), 3.67 (m, 2H), 4.43 (t, J=6.9 Hz, 4H), 7.02-7.22 (m, 4H), 8.24 (dd, J=7.8, 6.3 Hz, 2H), 8.85

(d, J=8.1 Hz, 2H), 9.17 (d, J=6.0 Hz, 2H), 9.39 (s, 2H) ppm; $^{13}$C NMR (75 MHz, CD$_3$OD) δ 23.4, 27.1, 31.8, 32.2, 33.2, 33.7, 40.2, 57.6, 63.2, 68.9, 126.9, 129.6, 130.2, 139.8, 140.9, 145.8, 146.4 ppm.

Example 43

Synthesis of Compound 1,2-bis-[5-(3-n-butyl-pyridinium)-pentyl]-benzene dibromide

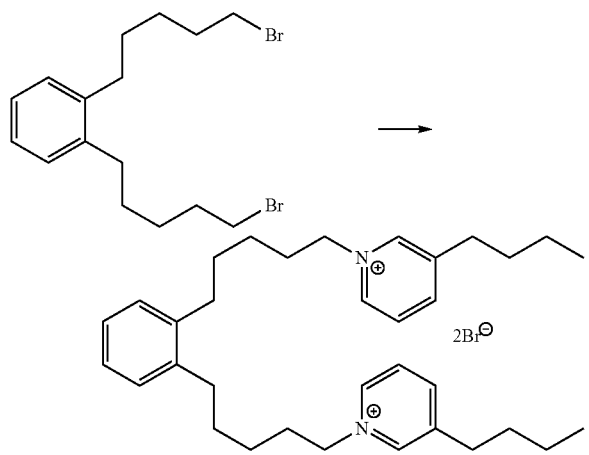

A mixture of 1,2-bis-(5-bromo-pentyl)-benzene (232 mg, 0.62 mmol) and 4-n-butylpyridine (0.5 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 154 mg of the title compound. Yield: 39%. $^1$H NMR (300 MHz, CD$_3$OD) δ 0.98 (t, J=7.2 Hz, 6H), 1.30-1.87 (m, 16H), 2.09 (m, 4H), 2.64 (t, J=7.5 Hz, 4H), 2.92 (t, J-7.2 Hz, 4H), 4.70 (t, J=6.6 Hz, 4H), 6.98-7.18 (m, 4H), 8.05 (dd, J=8.1, 5.4 Hz, 2H), 8.49 (d, J=8.1 Hz, 2H), 9.95 (d, J=5.7 Hz, 2H), 10.08 (s, 2H) ppm; $^{13}$C NMR (75 MHz, CD$_3$OD) δ 14.4, 23.3, 27.2, 31.9, 32.6, 33.3, 33.4, 33.8, 62.8, 127.0, 128.9, 130.3, 140.9, 143.3, 145.2, 145.5, 146.5 ppm.

Example 44

Synthesis of Compound 1,2-bis-[5-(3-bromo-pyridinium)-pentyl]-benzene dibromide

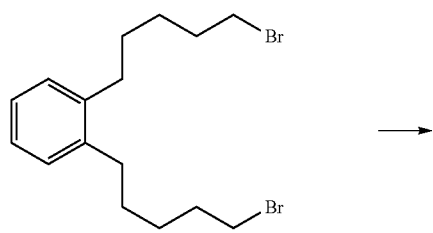

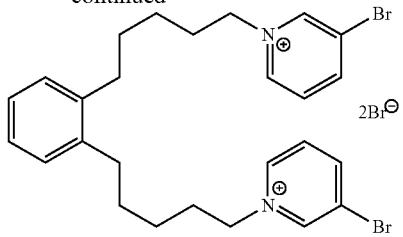

A mixture of 1,2-bis-(5-bromo-pentyl)-benzene (235 mg, 0.72 mmol) and 3-bromopyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 410 mg of the title compound. Yield: 95%. $^1$H NMR (300 MHz, CD$_3$OD) δ 1.30-1.75 (m, 8H), 2.13 (m, 4H), 2.63 (t, J=7.5 Hz, 4H), 4.79 (t, J=7.5 Hz, 4H), 7.00-7.21 (m, 4H), 8.12 (dd, J-8.1, 6.0 Hz, 2H), 8.84 (d, J=7.8 Hz, 2H), 9.24 (d, J=5.7 Hz, 2H), 9.58 (s, 2H) ppm; $^{13}$C NMR (75 MHz, CD$_3$OD) δ 27.2, 31.9, 32.5, 33.4, 63.2, 124.0, 127.0, 130.2, 140.9, 144.9, 147.1, 149.4 ppm.

Example 45

Synthesis of Compound 1,2-bis-[5-pyridinium-pentyl]-benzene dibromide

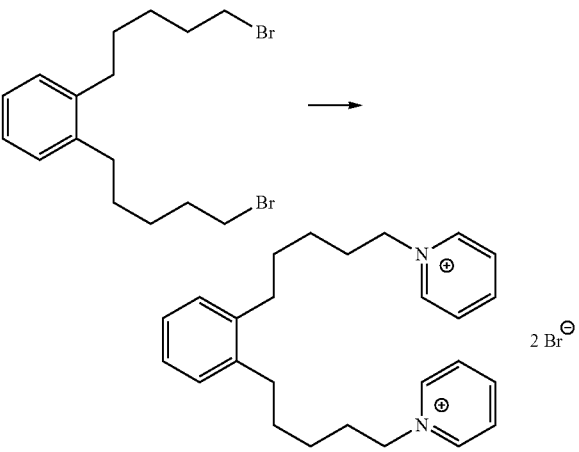

A mixture of 1,2-bis-(5-bromo-pentyl)-benzene (244 mg, 0.65 mmol) and pyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 317 mg of the title compound. Yield: 92%. $^1$H NMR (300 MHz, CD$_3$OD) δ 1.48 (m, 4H), 1.65 (m, 4H), 2.10 (m, 4H), 2.63 (t, J-7.5 Hz, 4H), 4.74 (t, J=7.5 Hz, 4H), 7.02-7.20 (m, 4H), 8.16 (t, J=6.9 Hz, 4H), 8.64 (t, J=7.8 Hz, 2H), 9.13 (d, J=5.4 Hz, 4H) ppm; $^{13}$C NMR (75 MHz, CD$_3$OD) δ 27.1, 31.9, 32.5, 33.3, 62.9, 127.0, 129.4, 130.3, 140.9, 145.8, 146.7 ppm.

Example 46

Synthesis of Compound 5-[3-(5-hydroxy-pent-1-ynyl)-phenyl]-pent-4-yn-1-ol

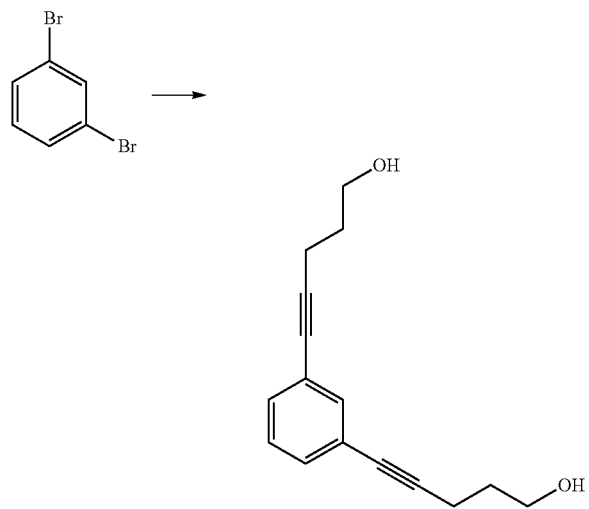

1,3-Dibromobenzene (7.48 g, 31.71 mmol), 4-pentyn-1-ol (6.40 g, 76.10 mmol), and &M(triphenylphosphine)palladium(II) dichloride (445 mg, 0.63 mmol) was stirred in triethylamine (150 mL) under nitrogen for 5 min. Copper(I) iodide (61 mg, 0.32 mmol) was added and the mixture was stirred for 18 hrs at 75° C. The mixture was cooled to room temperature and filtered through a celite pad, rinsed with ethylacetate. The combined filtrate was evaporated to dryness under reduced pressure. The resulting residue was purified by column chromatography (chloroform:methanol 20:1) to afford 7.24 g of the title compound. Yield: 94%. $^1$H NMR (300 MHz, CDCl$_3$) δ 1.85 (m, 4H), 2.53 (t, J=6.9 Hz, 4H), 3.81 (t, J=6.0 Hz, 4H), 7.16-7.31 (m, 3H), 7.42 (t, J=1.2 Hz, 1H) ppm; $^{13}$C NMR (75 MHz, CDCl$_3$) δ 16.2, 31.6, 61.9, 80.6, 90.0, 124.0, 128.3, 130.8, 134.7 ppm.

Example 47

Synthesis of Compound 1,3-bis-(5-bromo-pent-1-ynyl)-benzene

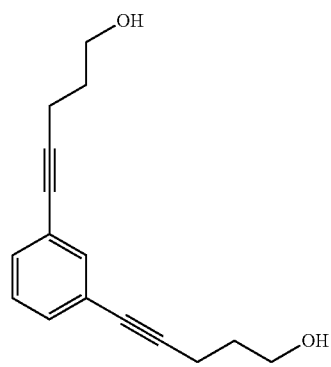

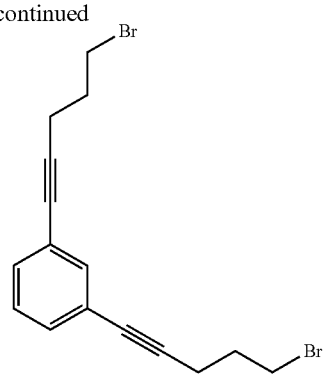

5-[3-(5-Hydroxy-pent-1-ynyl)-phenyl]-pent-4-yn-1-ol (2.86 g, 11.80 mmol) and carbon tetrabromide (9.78 g, 29.50 mmol) were dissolved in dry methylene chloride (30 mL) and cooled to 0° C. Triphenyl phosphine (8.13 g, 30.98 mmol) in methylene chloride (20 mL) was added dropwise and the mixture was stirred for 1 h at 0° C. The mixture was poured into hexanes (200 mL) and then filtered through a short silica gel column, washed with ethylacetate/hexanes (1/4). The combined organic solvents were evaporated to dryness under reduced pressure. The resulting residue was purified by column chromatography (hexanes:ethylacetate 30:1) to afford 3.64 g of the title compound. Yield: 84%. $^1$H NMR (300 MHz, CDCl$_3$) δ 2.13 (m, 4H), 2.60 (t, J=6.6 Hz, 4H), 3.58 (dt, J=6.6 Hz, 4H), 7.18-7.32 (m, 3H), 7.43 (t, J=1.5 Hz, 1H) ppm; $^{13}$C NMR (75 MHz, CDCl$_3$) δ 18.4, 31.7, 32.7, 81.1, 88.7, 123.8, 128.4, 131.0, 134.8 ppm.

Example 48

Synthesis of Compound 1,3-bis-[5-(2-methyl-pyridinium)-pent-1-ynyl]-benzene dibromide

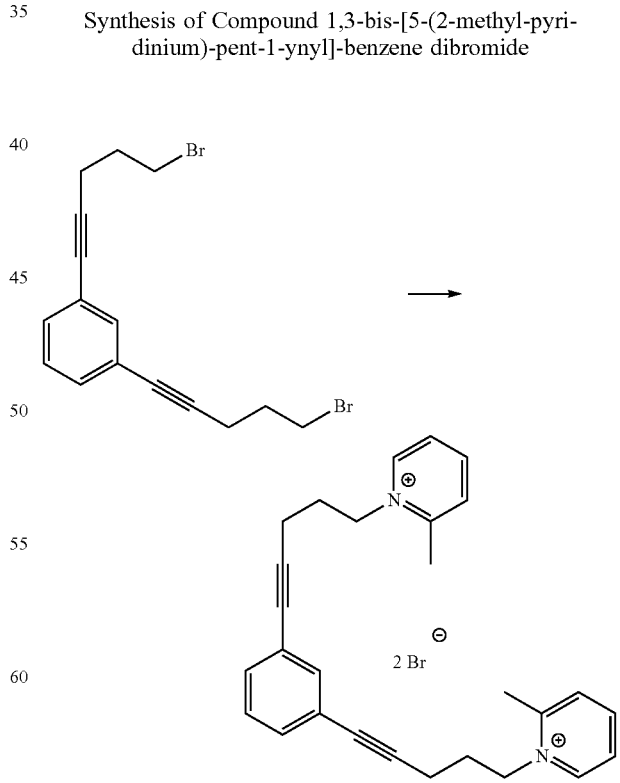

A mixture of 1,3-bis-(5-bromo-pent-1-ynyl)-benzene (368 mg, 1.00 mmol) and 2-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 472 mg of the title compound. Yield: 84%. $^1$H NMR (300 MHz, CD$_3$OD) δ 2.29 (m, 4H), 2.69 (t, J=6.6 Hz, 4H), 2.97 (s, 6H), 4.81 (t, J=7.5 Hz, 4H), 7.23-7.38 (m, 3H), 7.43 (d, J=1.5 Hz, 1H), 7.95 (t, J=6.9 Hz, 2H), 8.01 (d, J=7.8 Hz, 2H), 8.43 (dt, J=7.8, 1.5 Hz, 2H), 8.99 (dd, J=6.3, 1.5 Hz, 2H) ppm; $^{13}$C NMR (75 MHz, CD$_3$OD) δ 17.4, 20.9, 29.9, 58.3, 82.1, 89.6, 124.7, 127.0, 129.8, 131.5, 132.2, 135.2, 146.5, 146.6, 156.8 ppm.

Example 49

Synthesis of Compound 1,3-bis-[5-(3-methyl-pyridinium)-pent-1-ynyl]-benzene dibromide

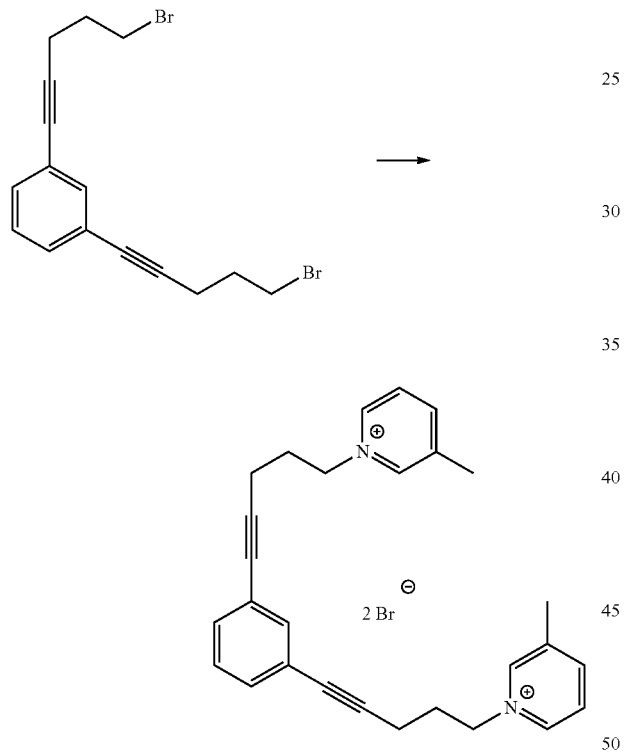

A mixture of 1,3-bis-(5-bromo-pent-1-ynyl)-benzene (348 mg, 0.94 mmol) and 3-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 469 mg of the title compound. Yield: 90%. $^1$H NMR (300 MHz, CD$_3$OD) δ 2.35 (m, 4H), 2.56 (s, 6H) 2.63 (t, J=6.6 Hz, 4H), 4.80 (t, J=7.2 Hz, 4H), 7.22-7.33 (m, 3H), 7.37 (s, 1H), 8.00 (dd, J=8.1, 6.3 Hz, 2H), 8.39 (d, J=7.8 Hz, 2H), 8.91 (d, J=6.3 Hz, 2H), 9.00 (s, 2H) ppm; $^{13}$C NMR (75 MHz, CD$_3$OD) δ 17.3, 18.8, 31.0, 62.1, 82.1, 89.4, 124.7, 128.7, 129.7, 132.1, 135.4, 141.1, 143.3, 145.7, 147.4 ppm.

Example 50

Synthesis of Compound 1,3-bis-[5-(4-methyl-pyridinium)-pent-1-ynyl]-benzene dibromide

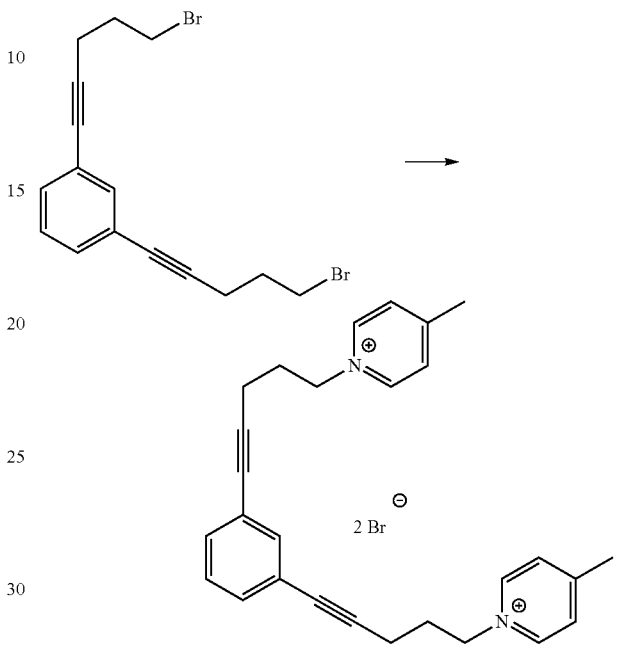

A mixture of 1,3-bis-(5-bromo-pent-1-ynyl)-benzene (350 mg, 0.94 mmol) and 4-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 478 mg of the title compound. Yield: 92%. $^1$H NMR (300 MHz, CD$_3$OD) δ 2.33 (m, 4H), 2.58 (s, 6H), 2.63 (t, J=6.6 Hz, 4H), 4.77 (t, J=6.9 Hz, 4H), 7.28 (s, 4H), 7.93 (d, J=6.3 Hz, 4H), 8.90 (d, J=6.6 Hz, 4H) ppm; $^{13}$C NMR (75 MHz, CD$_3$OD) δ 17.3, 22.3, 30.8, 61.4, 81.9, 89.5, 124.7, 129.9, 132.1, 135.2, 145.0, 161.2 ppm.

Example 51

Synthesis of Compound 1,3-bis-[5-(2,4-dimethyl-pyridinium)-pent-1-ynyl]-benzene dibromide

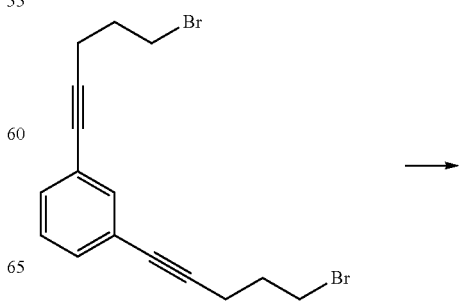

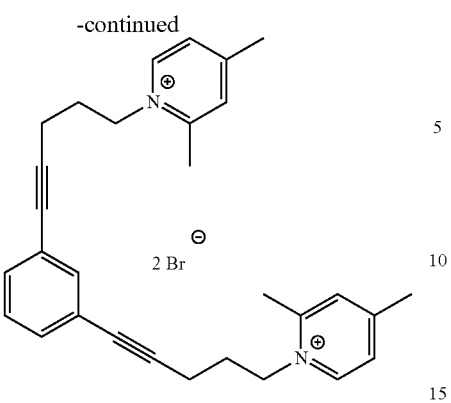

A mixture of 1,3-bis-(5-bromo-pent-1-ynyl)-benzene (249 mg, 0.68 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 357 mg of the title compound. Yield: 91%. $^1$H NMR (300 MHz, CD$_3$OD) δ 2.29 (m, 4H), 2.51 (s, 3H), 2.73 (t, J=6.6 Hz, 4H), 2.94 (s, 3H), 4.79 (t, J=7.5 Hz, 4H), 7.33 (d, J=0.9 Hz, 4H), 7.78 (dd, J=6.6, 2.1 Hz, 2H), 7.85 (s, 2H), 8.89 (d, J=6.6 Hz, 2H) ppm; $^{13}$C NMR (75 MHz, CD$_3$OD) δ 17.4, 20.6, 22.0, 29.9, 57.6, 82.0, 89.7, 124.8, 127.6, 129.9, 131.7, 132.1, 135.1, 145.6, 155.5, 160.5 ppm.

Example 52

Synthesis of Compound 1,3-bis-[5-(3,4-dimethyl-pyridiniiim)-pent-1-ynyl]-benzene dibromide [GZ 570 B]

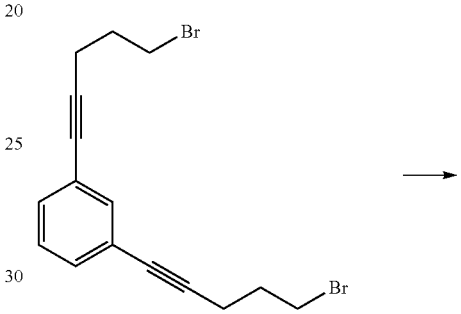

A mixture of 1,3-bis-(5-bromo-pent-1-ynyl)-benzene (253 mg, 0.69 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 261 mg of the title compound. Yield: 65%. $^1$H NMR (300 MHz, CD$_3$OD) δ 2.36 (s, 3H), 2.43 (s, 3H), 2.47 (m, 4H), 2.66 (t, J=6.6 Hz, 4H), 4.77 (t, J=6.9 Hz, 4H), 7.18-7.36 (m, 4H), 7.87 (d, J=6.3 Hz, 2H), 8.82 (d, J=6.3 Hz, 2H), 8.92 (s, 2H), ppm; $^{13}$C NMR (75 MHz, CD$_3$OD) δ 17.2, 17.4, 20.4, 30.8, 61.5, 81.9, 89.5, 124.9, 129.5, 129.8, 132.0, 135.3, 139.8, 142.9, 144.5, 160.0 ppm.

Example 53

Synthesis of Compound 1,3-bis-[5-(3,5-dimethyl-pyridinium)-pent-1-ynyl]-benzene dibromide

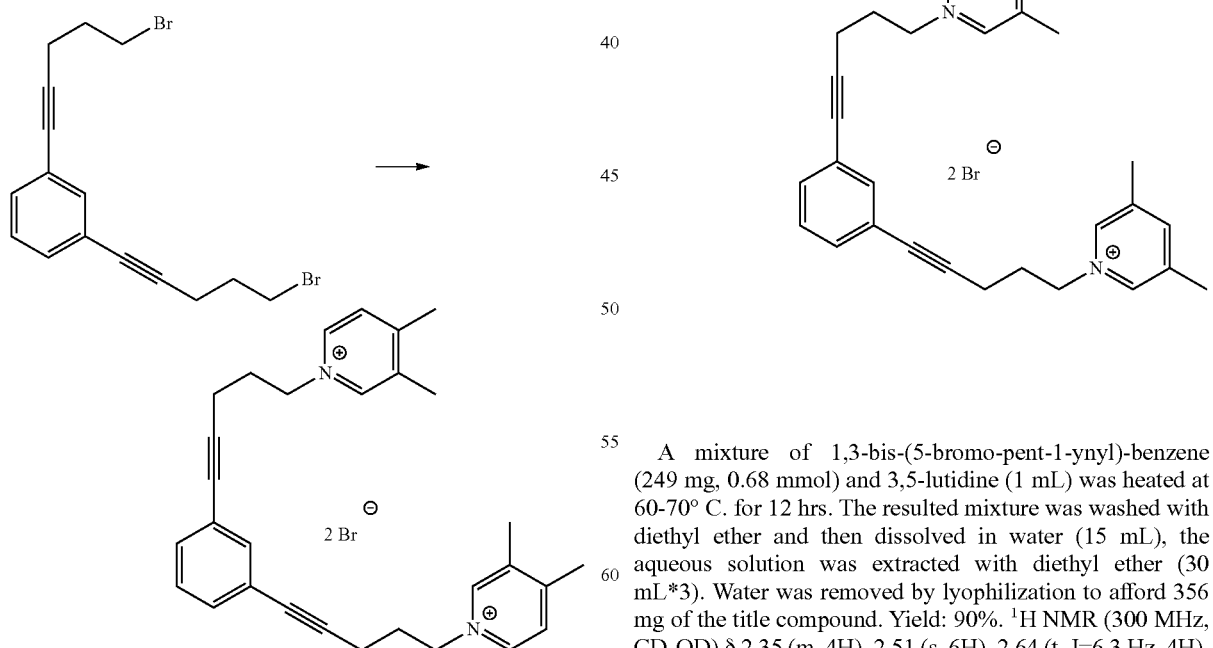

A mixture of 1,3-bis-(5-bromo-pent-1-ynyl)-benzene (249 mg, 0.68 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL*3). Water was removed by lyophilization to afford 356 mg of the title compound. Yield: 90%. $^1$H NMR (300 MHz, CD$_3$OD) δ 2.35 (m, 4H), 2.51 (s, 6H), 2.64 (t, J=6.3 Hz, 4H), 4.75 (t, J=7.2 Hz, 4H), 7.28 (d, J=1.2 Hz, 3H), 7.33 (s, 1H), 8.19 (s, 2H), 8.82 (s, 4H) ppm; $^{13}$C NMR (75 MHz, CD$_3$OD) δ 17.4, 18.7, 31.0, 61.8, 81.9, 89.7, 124.6, 129.7, 132.0, 135.2, 140.1, 142.8, 147.9 ppm.

Example 54

Synthesis of Compound 1,3-bis-(5-quinolinium-pent-1-ynyl)-benzene dibromide [GZ571A]

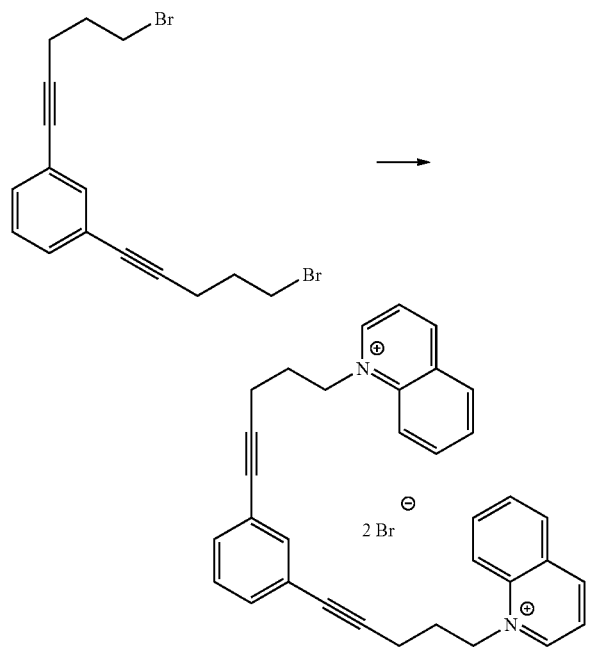

A mixture of 1,3-bis-(5-bromo-pent-1-ynyl)-benzene (253 mg, 0.69 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 271 mg of the title compound. Yield: 63%. $^1$H NMR (300 MHz, CD$_3$OD) δ 2.45 (m, 4H), 2.73 (t, J=6.6 Hz, 4H), 5.31 (t, J=7.5 Hz, 4H), 7.14 (d, J-1.2 Hz, 1H), 7.20-7.30 (m, 3H), 8.02-8.17 (m, 4H), 8.31 (dt, J=7.2, 1.2 Hz, 2H), 8.41 (dd, J=8.4, 1.5 Hz, 2H), 8.67 (d, J=9.0 Hz, 2H), 9.17 (d, J=8.7 Hz, 2H), 9.54 (dd, J=5.7, 1.5 Hz, 2H) ppm; $^{13}$C NMR (75 MHz, CD$_3$OD) δ 17.5, 29.6, 58.7, 81.8, 89.8, 119.7, 123.1, 124.4, 129.6, 131.2, 131.4, 131.9, 132.1, 135.0, 137.3, 139.1, 149.1, 150.6 ppm.

Example 55

Synthesis of Compound 1,3-bis-(5-isoquinolinium-pent-1-ynyl)-benzene dibromide

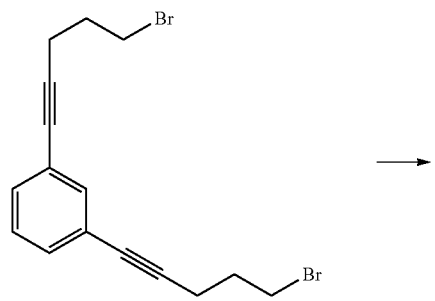

A mixture of 1,3-&£s-(5-bromo-pent-1-ynyl)-benzene (257 mg, 0.70 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 316 mg of the title compound. Yield: 72%. $^1$H NMR (300 MHz, CD$_3$OD) δ 2.47 (m, 4H), 2.74 (t, J=6.3 Hz, 4H), 5.01 (t, J=6.9 Hz, 4H), 6.54 (s, 1H), 6.85-7.03 (m, 3H), 8.01 (dt, J=6.0, 1.5 Hz, 2H), 8.11-8.22 (m, 4H), 8.40-8.57 (m, 4H), 8.79 (dd, J=6.9, 1.2 Hz, 2H), 10.15 (s, 2H) ppm; $^{13}$C NMR (75 MHz, CD$_3$OD) δ 17.6, 30.6, 62.6, 82.0, 89.2, 124.4, 127.5, 128.4, 129.2, 129.3, 131.5, 131.7, 132.5, 134.7, 136.0, 138.4, 139.1, 151.5 ppm.

Example 56

Synthesis of Compound 1,3-bis-[5-(2'-S-nicotinium-pent-1-ynyl)]benzene dibromide

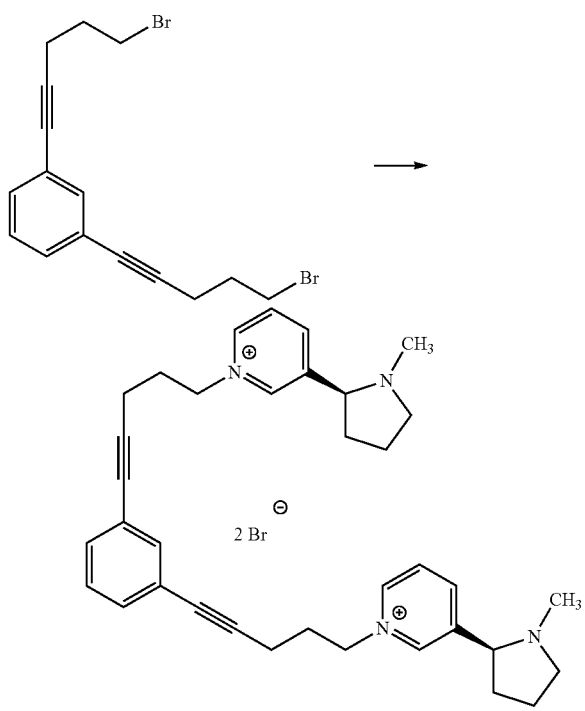

A mixture of 1,3-bis-(5-bromo-pent-1-ynyl)-benzene (244 mg, 0.66 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 388 mg of the title compound. Yield: 85%. $^1$H NMR (300 MHz, CD$_3$OD) δ 1.75-2.15 (m, 6H), 2.35 (s, 6H), 2.33-2.50 (m, 6H), 2.63 (t, J=6.6 Hz, 4H), 3.37 (m, 2H), 3.74 (m, 2H), 4.87 (t, J=6.9 Hz, 4H), 7.23-7.35 (m, 3H), 7.41 (s, 1H), 8.12 (dd, J-8.1, 6.0 Hz, 2H), 8.61 (dd, J=7.8, 0.9 Hz, 2H), 9.03 (dd, J=6.0, 0.9 Hz, 2H), 9.18 (s, 2H) ppm; $^{13}$C NMR (75 MHz, CD$_3$OD) δ 17.2, 23.9, 30.8, 35.5, 40.7, 57.8, 62.3, 68.5, 82.2, 89.3, 124.7, 129.4, 129.7, 132.2, 135.4, 144.9, 145.1, 145.4, 146.1 ppm.

Example 57

Synthesis of Compound 1,3-bis-[5-(3-n-butyl-pyridinium)-pent-1-ynyl]-benzene dibromide

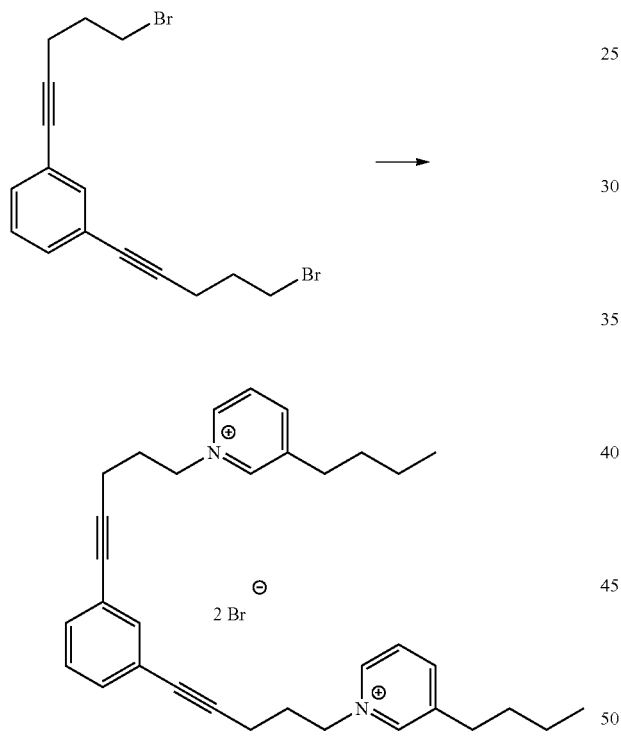

A mixture of 1,3-bis-(5-bromo-pent-1-ynyl)-benzene (242 mg, 0.66 mmol) and 4-n-butylpyridine (0.5 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 347 mg of the title compound. Yield: 83%. $^1$H NMR (300 MHz, CD$_3$OD) δ 0.98 (t, J=7.2 Hz, 6H), 0.95 (t, J=7.2 Hz, 6H), 1.40 (m, 4H), 1.67 (m, 4H), 2.39 (m, 4H), 2.67 (t, J=6.6 Hz, 4H), 2.88 (t, J=7.8 Hz, 4H), 4.90 (t, J=6.9 Hz, 4H), 7.29 (d, J=1.2 Hz, 3H), 7.33 (s, 1H), 8.07 (dd, J=7.8, 6.0 Hz, 2H), 8.45 (d, J=8.1 Hz, 2H), 9.04 (d, J-6.3 Hz, 2H), 9.14 (s, 2H) ppm; $^{13}$C NMR (75 MHz, CD$_3$OD) δ 14.4, 17.3, 23.3, 31.0, 33.3, 33.6, 62.1, 82.1, 89.4, 124.7, 129.0, 129.7, 132.2, 135.4, 143.5, 145.4, 145.5, 146.8 ppm.

Example 58

Synthesis of Compound 1,3-bis-[5-(3-phenyl-pyridinium)-pent-1-ynyl]-benzene dibromide

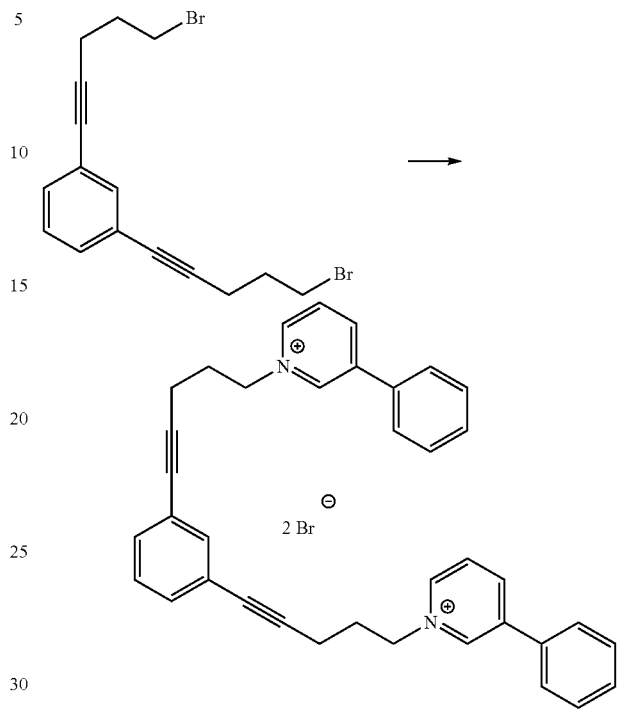

A mixture of 1,3-bis-(5-bromo-pent-1-ynyl)-benzene (243 mg, 0.66 mmol) and 3-bromopyridine (0.5 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 390 mg of the title compound. Yield: 87%. $^1$H NMR (300 MHz, CD$_3$OD) δ 2.41 (m, 4H), 2.70 (t, J=6.6 Hz, 4H), 5.00 (t, J=6.9 Hz, 4H), 7.15 (d, "J=1.2 Hz, 1H), 7.18 (m, 3H), 7.45-7.58 (m, 6H), 7.77-7.87 (m, 4H), 8.14 (dd, J-8.1, 6.0 Hz, 2H), 8.74 (ddd, J=8.1, 1.5, 1.2 Hz, 2H), 9.13 (d, J=6.0 Hz, 2H), 9.56 (s, 2H) ppm; $^{13}$C NMR (75 MHz, CD$_3$OD) δ 17.4, 30.9, 62.4, 82.0, 89.5, 124.5, 128.6, 129.5, 129.6, 130.6, 131.4, 132.0, 134.1, 135.3, 142.1, 143.9, 144.0, 144.2 ppm.

Example 59

Synthesis of Compound 1,3-bis-(5-pyridinium-pent-1-ynyl)-benzene dibromide

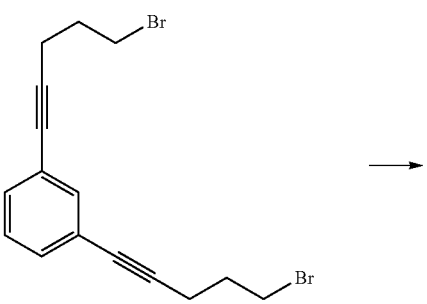

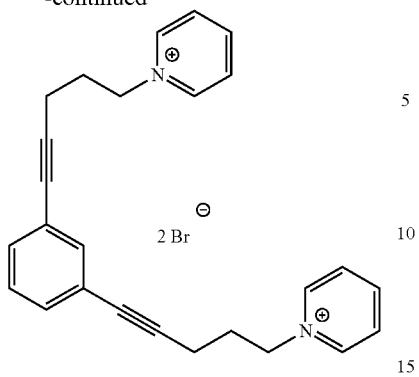

A mixture of 1,3-bis-(5-bromo-pent-1-ynyl)-benzene (240 mg, 0.65 mmol) and pyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 322 mg of the title compound. Yield: 94%. $^1$H NMR (300 MHz, CD$_3$OD) δ 2.40 (m, 4H), 2.68 (t, J=6.9 Hz, 4H), 4.94 (t, J=7.5 Hz, 4H), 7.32 (m, 3H), 7.39 (d, J=1.2 Hz, 1H), 8.19 (dd, J=7.8, 6.9 Hz, 4H), 8.63 (m, 2H), 9.23 (dd, J=7.2, 1.2 Hz, 4H) ppm; $^{13}$C NMR (75 MHz, CD$_3$OD) δ 17.2, 31.0, 62.1, 82.1, 89.4, 124.6, 129.4, 129.7, 132.2, 135.3, 146.0, 146.9 ppm.

Example 60

Synthesis of Compound
5-[3-(5-hydroxy-pentyl)-phenyl]-pentan-1-ol

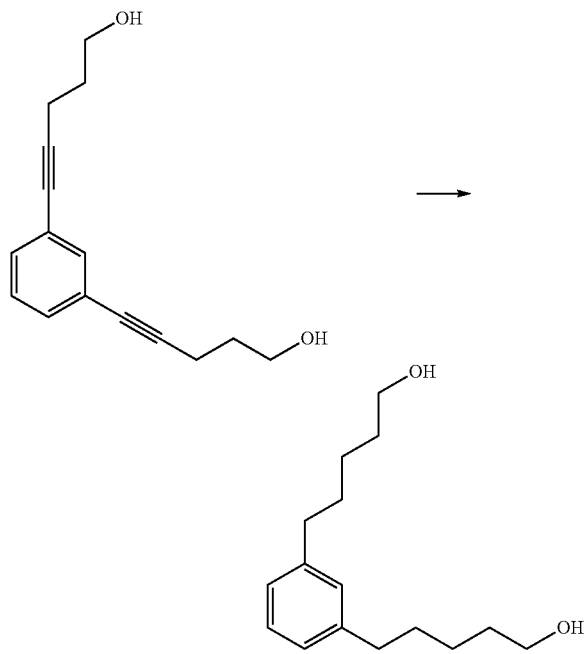

5-[3-(5-Hydroxy-pent-1-ynyl)-phenyl]-pent-4-yn-1-ol (3.40 g, 14.03 mmol) was dissolved in methanol (60 mL) and 10% Pd/C (2.5% w/w) was added. The resulting mixture was hydrogenated on a Parr hydrogenation apparatus (45 psi) for 12 hrs. The catalyst was removed by filtration through a Celite pad. The filter cake was rinsed with methanol, and the combined organic liquors were concentrated under reduced pressure. The crude product was purified by column chromatography (chloroform:methanol 20:1) to afford 3.12 g of the title compound. Yield: 89%. $^1$H NMR (300 MHz, CDCl$_3$) δ 1.30-1.45 (m, 4H), 1.50-1.72 (m, 8H), 2.59 (t, J=7.8 Hz, 4H), 3.62 (t, J=6.6 Hz, 4H), 6.99 (m, 3H), 7.18 (m, 1H) ppm; $^{13}$C NMR (75 MHz, CDCl$_3$) δ 25.7, 31.5, 32.8, 36.1, 63.0, 125.8, 128.3, 128.7, 142.5 ppm.

Example 61

Synthesis of Compound
1,3-bis-(5-bromo-pentyl)-benzene

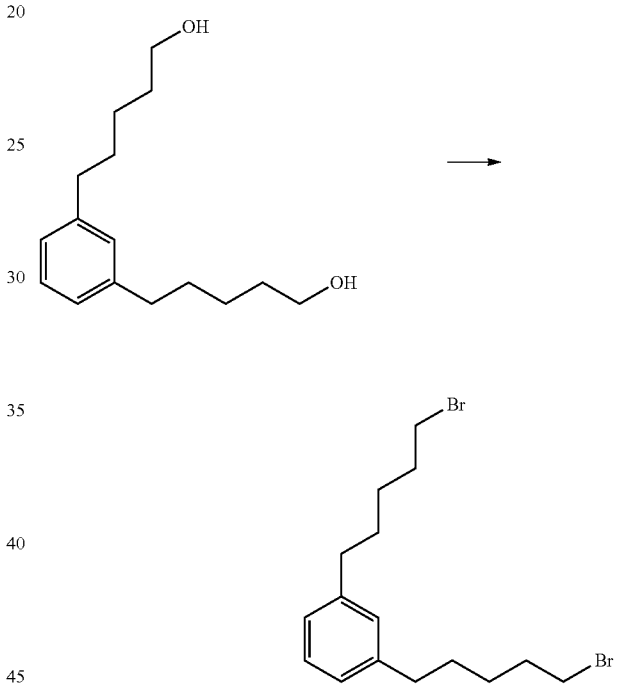

5-[3-(5-Hydroxy-pentyl)-phenyl]-pentan-1-ol (2.26 g, 9.03 mmol) and carbon tetrabromide (7.49 g, 22.58 mmol) were dissolved in dry methylene chloride (20 mL) and cooled to 0° C. Triphenyl phosphine (6.22 g, 23.70 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (1/4). The combined organic solvents were evaporated to dryness under reduced pressure. The resulting residue was purified by column chromatography (hexanes:ethylacetate 30:1) to afford 2.80 g of the title compound. Yield: 82%. $^1$H NMR (300 MHz, CDCl$_3$) δ 1.46 (m, 4H), 1.61 (m, 4H), 1.88 (m, 4H), 2.59 (t, J=7.8 Hz, 4H), 3.40 (t, J=6.9 Hz, 4H), 7.00 (m, 3H), 7.19 (m, 1H) ppm; $^{13}$C NMR (75 MHz, CDCl$_3$) δ 28.1, 30.9, 32.9, 34.1, 36.0, 125.9, 128.3, 128.6, 142.4 ppm.

Example 62

Synthesis of Compound
1,3-bis-[5-(2-methyl-pyridinium)-pentyl]-benzene dibromide

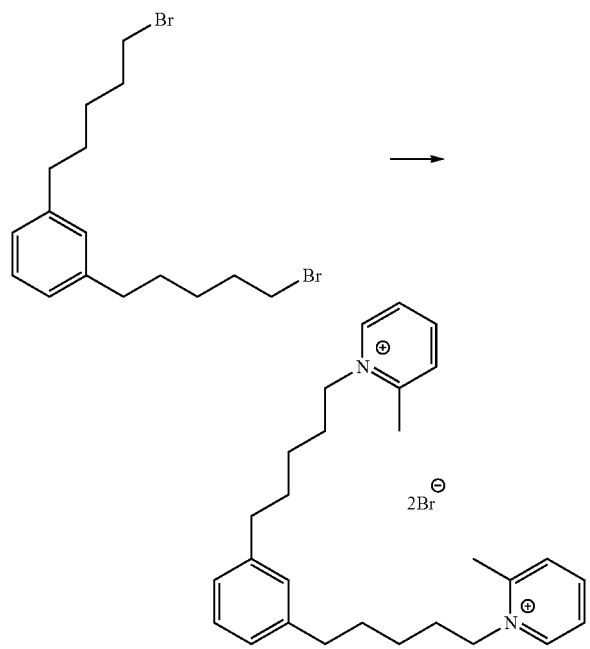

A mixture of 1,3-bis-(5-bromo-pentyl)-benzene (240 mg, 0.64 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 328 mg of the title compound. Yield: 91%. $^1$H NMR (300 MHz, CD$_3$OD) δ 1.54 (m, 4H), 1.73 (m, 4H), 2.02 (m, 4H), 2.63 (t, J=7.5 Hz, 4H), 2.95 (s, 6H), 4.67 (t, J=7.5 Hz, 4H), 6.98-7.22 (m, 4H), 7.97 (t, J=6.9 Hz, 2H), 8.07 (d, J=8.1 Hz, 2H), 8.49 (t, J=7.8 Hz, 2H), 9.05 (d, J=6.3 Hz, 2H) ppm; $^{13}$C NMR (75 MHz, CD$_3$OD) δ 20.9, 26.9, 31:0, 32.0, 36.5, 59.2, 126.85, 126.88, 129.3, 129.6, 131.4, 143.3, 146.2, 146.3, 156.4 ppm.

Example 63

Synthesis of Compound
1,3-bis-[5-(3-methyl-pyridinium)-pentyl]-benzene dibromide

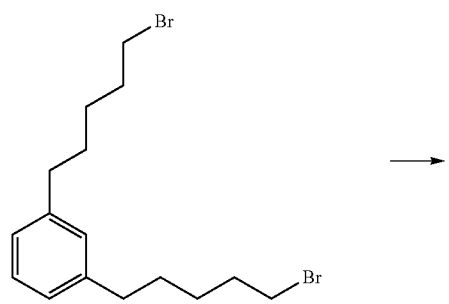

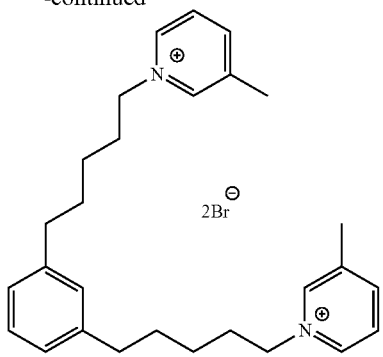

A mixture of 1,3-bis-(5-bromo-pentyl)-benzene (265 mg, 0.70 mmol) and 3-picoline (1 ml) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 362 mg of the title compound. Yield: 91%. $^1$H NMR (300 MHz, CD$_3$OD) δ 1.44 (m, 4H), 1.69 (m, 4H), 2.10 (m, 4H), 2.59 (t, J=7.8 Hz, 4H), 2.62 (s, 6H), 4.70 (t, J=7.5 Hz, 4H), 6.94-7.09 (m, 3H), 7.16 (t, J=1.5 Hz, 1H), 8.03 (dd, J=8.1, 6.0 Hz, 2H), 8.48 (d, J=8.1 Hz, 2H), 8.96 (d, J=6.0 Hz, 2H), 9.08 (s, 2H) ppm; $^{13}$C NMR (75 MHz, CD$_3$OD) δ 18.9, 26.6, 31.9, 32.3, 36.5, 62.6, 126.9, 128.6, 129.3, 129.6, 140.9, 142.9, 143.3, 145.3, 147.1 ppm.

Example 64

Synthesis of Compound
1,3-bis-[5-(4-methyl-pyridinium)-pentyl]-benzene dibromide

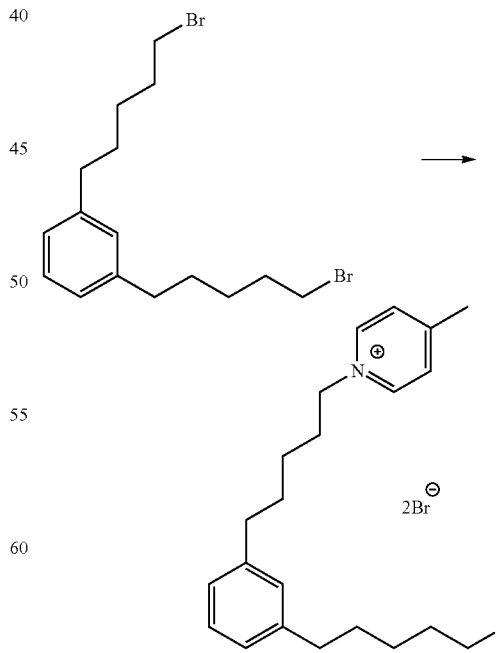

A mixture of 1,3-bis-(5-bromo-pentyl)-benzene (240 mg, 0.64 mmol) and 4-picoline (1 mL) was heated at 60-70° C.

for 12 hrs. The resulted mixture was washed with diethyl ether and then dissolved in water (15 mL), the aqueous solution was extracted with diethyl ether (30 mL×3). Water was removed by lyophilization to afford 332 mg of the title compound. Yield: 92%. $^1$H NMR (300 MHz, CD$_3$OD) δ 1.42 (m, 4H), 1.67 (m, 4H), 2.06 (m, 4H), 2.59 (t, J=7.5 Hz, 4H), 2.69 (s, 6H), 4.66 (t, J=7.5 Hz, 4H), 6.95-7.08 (m, 3H), 7.16 (t, J=7.5 Hz, 1H), 7.97 (d, J=6.3 Hz, 4H), 8.94 {d, J=6.3 Hz, 4H) ppm; $^{13}$C NMR (75 MHz, CD$_3$OD) δ 22.4, 26.6, 31.9, 32.2, 36.5, 61.9, 126.9, 129.3, 129.6, 129.8, 143.3, 144.7, 160.7 ppm.

Example 65

Synthesis of Compound 1,3-bis-[5-(2,4-dimethyl-pyridinium)-pentyl]-benzene dibromide

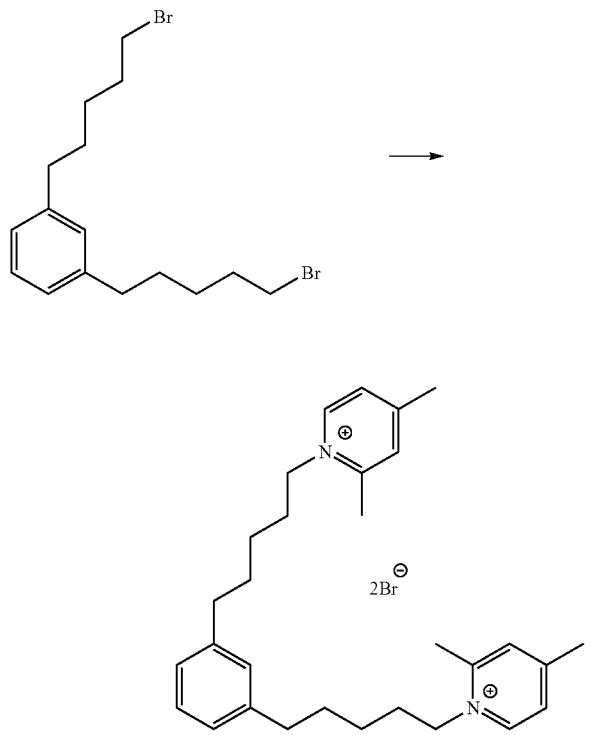 [SMILES: BrCCCCCc1cccc(CCCCCBr)c1 ; Cc1cc[n+](CCCCCc2cccc(CCCCC[n+]3ccc(C)cc3C)c2)c(C)c1]

A mixture of 1,3-bis-(5-bromo-pentyl)-benzene (237 mg, 0.63 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 323 mg of the title compound. Yield: 87%. $^1$H NMR (300 MHz, CD$_3$OD) δ 1.51 (m, 4H), 1.71 (m, 4H), 1.99 (m, 4H), 2.62 (t, J=7.5 Hz, 4H), 2.64 (s, 6H), 2.87 (s, 6H), 4.58 (t, J=7.5 Hz, 4H), 6.96-7.12 (m, 3H), 7.17 (t, J=7.5 Hz, 1H), 7.78 (dd, J=6.6, 1.5 Hz, 2H), 7.89 (d, J=1.5 Hz, 2H), 8.82 (d, J=6.6 Hz, 2H) ppm; $^{13}$C NMR (75 MHz, CD$_3$OD) δ 20.5, 22.1, 26.9, 31.1, 32.1, 36.6, 58.4, 126.9, 127.5, 129.3, 129.6, 131.6, 143.3, 145.3, 155.1, 160.1 ppm.

Example 66

Synthesis of Compound 1,3-bis-[5-(3,4-dimethyl-pyridinium)-pentyl]-benzene dibromide [GZ 578 B]

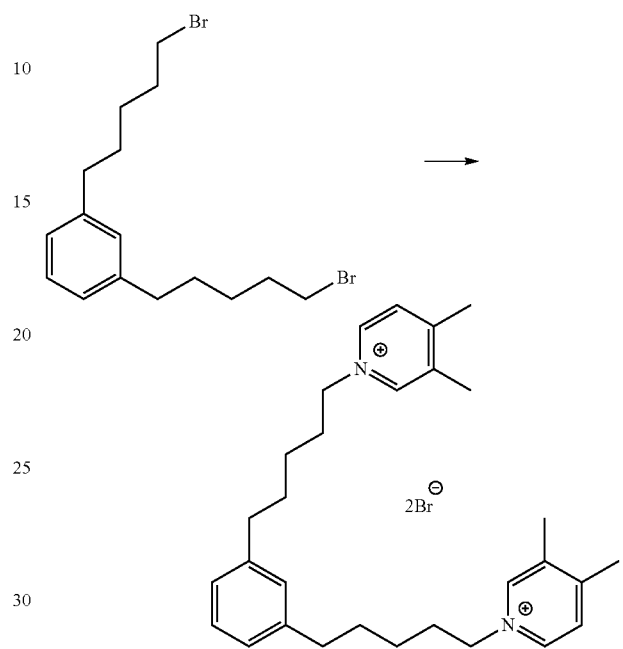

A mixture of 1,3-bis-(5-bromo-pentyl)-benzene (235 mg, 0.62 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 350 mg of the title compound. Yield: 97%. $^1$H NMR (300 MHz, CD$_3$OD) δ 1.44 (m, 4H), 1.68 (m, 4H), 2.09 (m, 4H), 2.51 (s, 6H), 2.59 (t, J=7.8 Hz, 4H), 2.60 (s, 6H), 4.65 (t, J=7.5 Hz, 4H), 6.96-7.20 (m, 4H), 7.92 (d, J=6.3 Hz, 2H), 8.82 (d, J=6.3 Hz, 2H), 8.96 (s, 2H) ppm; $^{13}$C NMR (75 MHz, CD$_3$OD) δ 17.3, 20.7, 26.6, 31.9, 32.2, 36.5, 61.7, 126.8, 129.2, 129.3, 129.5, 139.6, 142.3, 143.2, 143.9, 159.4 ppm.

Example 67

Synthesis of Compound 1,3-bis-[5-(3,5-dimethyl-pyridinium)-pentyl]-benzene dibromide

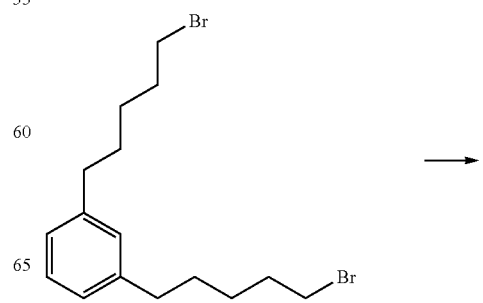

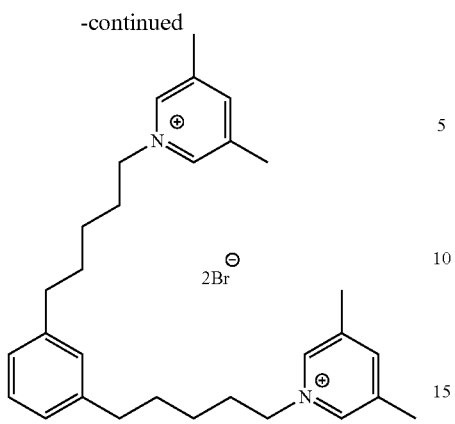

A mixture of 1,3-bis-(5-bromo-pentyl)-benzene (246 mg, 0.65 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 371 mg of the title compound. Yield: 96%. $^1$H NMR (300 MHz, CD$_3$OD) δ 1.46 (m, 4H), 1.68 (m, 4H), 2.11 (m, 4H), 2.58 (s, 12H), 2.63 (t, J=6.6 Hz, 4H), 4.66 (t, J=7.5 Hz, 4H), 6.95-7.20 (m, 4H), 8.34 (s, 2H), 8.92 (s, 4H) ppm; $^{13}$C NMR (75 MHz, CD$_3$OD) δ 18.7, 26.7, 32.0, 32.4, 36.5, 62.3, 126.8, 129.2, 129.5, 140.0, 142.6, 143.3, 147.6 ppm.

Example 68

Synthesis of Compound
1,3-bis-(5-quinolinium-pentyl)-benzene dibromide

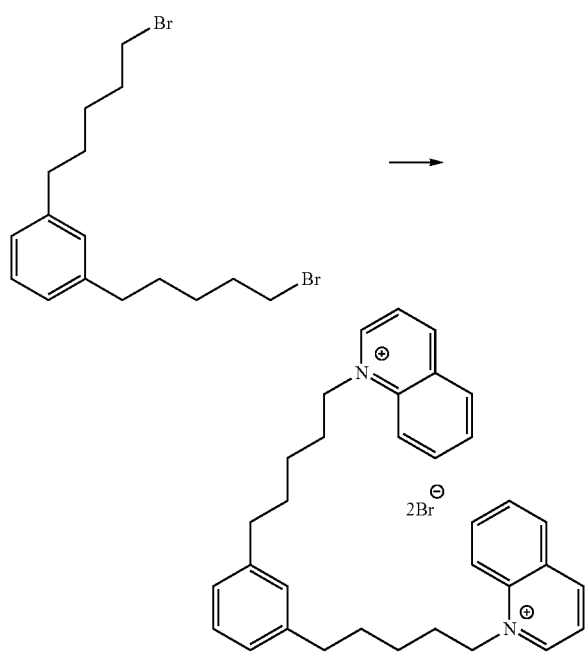

A mixture of 1,3-bis-(5-bromo-pentyl)-benzene (253 mg, 0.67 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 383 mg of the title compound. Yield: 90%. $^1$H NMR (300 MHz, CD$_3$OD) δ 1.52 (m, 4H), 1.64 (m, 4H), 2.13 (m, 4H), 2.51 (t, J=7.5 Hz, 4H), 5.17 (t, J=7.5 Hz, 4H), 6.81-7.06 (m, 4H), 8.03 (t, J=7.8 Hz, 2H), 8.12 (dd, J=8.4, 6.0 Hz, 2H), 8.31 (dt, J=6.0, 1.5 Hz, 2H), 8.45 (dd, J=8.4, 0.9 Hz, 2H), 8.61 (d, J=9.0 Hz, 2H), 9.27 (d, J=8.4 Hz, 2H), 9.59 (d, J=5.7 Hz, 2H) ppm; $^{13}$C NMR (75 MHz, CD$_3$OD) δ 27.0, 30.9, 31.9, 36.4, 59.3, 119.8, 123.0, 126.8, 129.1, 129.4, 131.2, 131.3, 132.0, 137.2, 138.9, 143.1, 148.7, 150.2 ppm.

Example 69

Synthesis of Compound
1,3-bis-(5-isoquinolinium-pentyl)-benzene
dibromide [GZ 579 B]

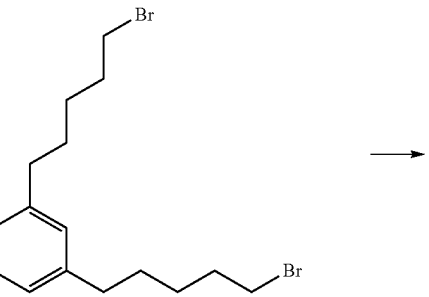

A mixture of 1,3-bis-(5-bromo-pentyl)-benzene (278 mg, 0.74 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 391 mg of the title compound. Yield: 83%. $^1$H NMR (300 MHz, CD$_3$OD) δ 1.43 (m, 4H), 1.64 (m, 4H), 2.17 (m, 4H), 2.49 (t, J=7.5 Hz, 4H), 4.88 (t, J=7.5 Hz, 4H), 6.81-7.06 (m, 4H), 8.01 (t, J=7.8 Hz, 2H), 8.19 (t, J=7.5 Hz, 2H), 8.28 (d, J=8.4 Hz, 2H), 8.53 (t, J=6.9 Hz, 4H), 8.79 (dd, J=6.9, 0.9 Hz, 2H), 10.16 (s, 2H) ppm; $^{13}$C NMR (75 MHz, CD$_3$OD) δ 26.6, 31.8, 32.2, 36.3, 62.6, 126.7, 127.4, 128.3, 128.7, 129.1, 129.4, 131.4, 132.3, 135.7, 138.1, 138.5, 143.1, 150.4 ppm.

Example 70

Synthesis of compound N,N'-[(1,1'-biphenyl)-4,4'-di-(3-propanyl)]-bis-[3-(2'-S-1-methyl-pyrrolidin-2-yl)-pyridinium] dibromide

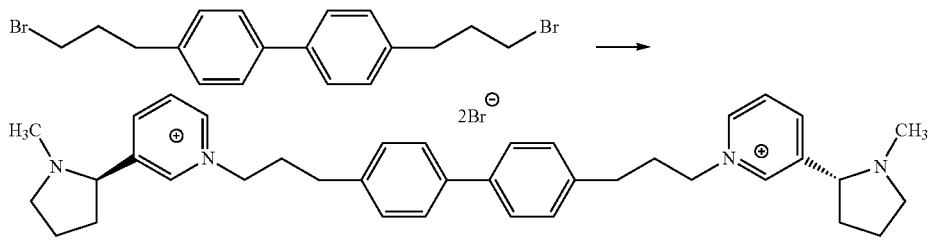

4,4'-Bis-(3-bromo-propyl)-biphenyl was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$H NMR (300 MHz, D$_2$O, ppm), 9.10 (s, 2H), 9.01 (d, J=6.0, 2H), 8.52 (d, J=7.8, 2H), 8.05 (dd, 2H), 7.49 (d, J=8.1, 4H), 7.33 (d, J=8.1, 4H), 4.79 (t, J=7.5, 4H), 3.53 (t, J=8.1, 2H), 3.23 (m, 2H), 2.83 (t, J=7.5, 4H), 2.30-2.45 (m, 6H), 2.20 (s, 6H), 1.85-1.97 (in, 4H). CNMR, 145.85, 144.42, 143.74, 143.54, 139.48, 138.65, 129.07, 128.23, 126.81, 67.32, 61.64, 56.83, 39.90, 35.21, 32.87, 31.99, 23.09.

Example 71

Synthesis of Compound N,N'-[(1,1'-biphenyl)-4,4'-di-(3-propanyl)]-bis-(3,5-dimethylpyridinium) dibromide [ZZ 1 55 D]

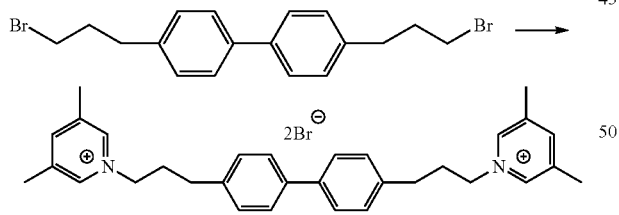

4,4'-Bis-(3-bromo-propyl)-biphenyl was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$H NMR (300 MHZ, D$_2$O, ppm), 8.79 (s, 4H), 8.15 (s, 2H), 7.46 (d, J=8.1, 4H), 7.31 (d, J=8.1, 4H), 4.66 (t, J=7.5, 4H), 2.81 (t, J=7.5, 2.46 (s, 12H), 2.34-2.39 (m, 4H). CNMR, 146.52, 141.58, 139.58, 139.00, 138.36, 129.05, 126.55, 61.28, 32.58, 32.05, 17.58.

Example 72

Synthesis of Compound N,N'-[(1,1'-biphenyl)-4,4'-di-(3-propanyl)]-bis-(3,4-dimethylpyridinium) dibromide [ZZ 55 C]

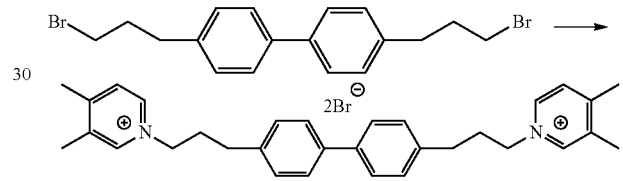

4,4'-Bis-(3-bromo-propyl)-biphenyl was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$H NMR (300 MHz, D$_2$O, ppm), 8.82 (s, 2H), 8.73 (d, J=6.3, 2H), 7.78 (d, 3=63, 2H), 7.47 (d, J=8.4, 4H), 7.29 (d, J=8.4, 4H), 4.64 (t, J=7.2, 4H), 2.79 (t, J=7.2, 4H), 2.470 (s, 6H), 2.32-2.42 (m, 10H). CNMR, 158.42, 143.02, 141.37, 139.56, 138.50, 138.32, 129.04, 128.32, 126.56, 60.61, 32.56, 31.97, 19.44, 16.12.

Example 73

Synthesis of Compound N,N'-[(1,1'-biphenyl)-4,4'-di-(3-propanyl)]-bis-(2,4-dimethylpyridinium) dibromide

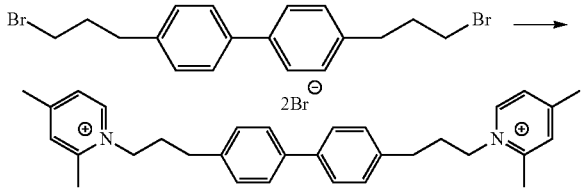

4,4'-Bis-(3-bromo-propyl)-biphenyl was added to a solution of 2,4-lutidine (3 mmol) in acetonitrile and the solution refluxed for 24 hours. The acetonitrile was removed in vacuum and the resulting residue was partitioned between ether and water. The aqueous layer was washed extensively with ether until no 2,4-lutidine left in the aqueous layer. The resulting aqueous solution of the product was lyophilized to yield the pure product. (75%). ¹H NMR (300 MHZ, D₂O, ppm), 8.83 (d, J=6.3, 2H), 7.79 (d, J=1.5, 2H), 7.68 (dd, J=7.8, J=1.5, 2H), 7.52 (d, J=8.4, 4H), 7.37 (d, J=8.4, 4H), 4.58 (t, J=7.5, 4H), 3.60 (t, J=7.2, 4H), 2.85 (t, J=7.2, 4H), 2.75 (s, 6H), 2.54 (s, 6H), 2.22-2.27 (m, 4H). CNMR, 159.10, 154.11, 144.30, 139.67, 138.39, 130.59, 129.22, 126.70, 126.55, 56.89, 31.94, 31.73, 31.02, 19.51.

Example 74

Synthesis of Compound N,N'-[(1,1'-biphenyl)-4,4'-di-(3-propanyl)]-bis-[3-(3-hydroxy-propyl)-pyridinium]dibromide [ZZ 55 G]

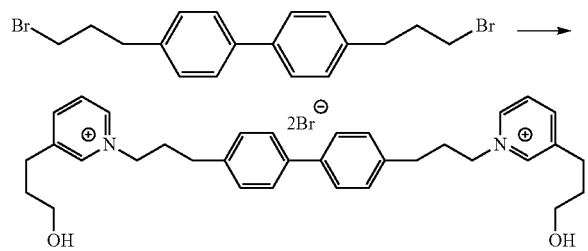

4,4'-Bis-(3-bromo-propyl)-biphenyl was added to a solution of 3-(3-hydroxypropyl)-pyridine (3 mmol) in acetonitrile and the solution refluxed for 24 hours. The acetonitrile was removed in vacuum and the resulting residue was partitioned between ether and water. The aqueous layer was washed extensively with ether until no 3-(3-Hydroxypropyl)-pyridine left in the aqueous layer. The resulting aqueous solution of the product was lyophilized to yield the pure product. (75%). ¹H NMR (300 MHz, D₂O, ppm), 8.96 (s, 2H), 8.87 (d, J=6.0, 2H), 8.42 (d, J=7.8, 2H), 7.96 (dd, J=6.0, J=7.8, 2H), 7.48 (d, J=8.1, 4H) 5 7.29 (d, J=8.1, 4H), 4.70 (t, J=7.5, 4H), 3.60 (t, J=6.3, 4H), 2.92 (t, J=6.3, 4H), 2.81 (t, J=7.5, 4H), 2.41 (p, 3=72, 4H), 1.87-1.95 (m, 4H). CNMR, 145.47, 144.22, 143.95, 142.22, 139.27, 138.77, 128.87, 127.75, 126.76, 61.55, 60.46, 32.94, 32.56, 31.96, 29.09.

Example 75

Synthesis of Compound N,N'-[(1,1'-biphenyl)-4,4'-di-(3-propanyl)]-bis-[5,6,7,8-tetrahydroquinolinium] dibromide

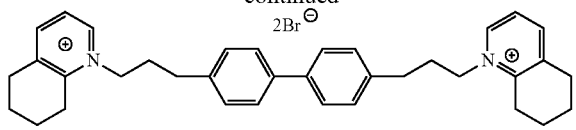

4,4'-Bis-(3-bromo-propyl)-biphenyl was added to a solution of 5,6,7,8-tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no 5,6,7,8-tetrahydroquinoline left in the aqueous layer. The resulting aqueous solution of the product was lyophilized to yield the pure product. (75%). ¹H NMR (300 MHz, D₂O, ppm), 8.79 (d, J-6.3, 2H), 8.19 (d, J=7.2, 2H), 7.77 (dd, J=6.3, J=7.8, 2H), 7.54 (d, J=7.8, 4H), 7.36 (d, J=7.8, 4H), 4.59 (t, J=7.8, 4H), 3.07 (t, J=6.3, 4H), 2.97 (t, J=6.0, 4H), 2.87 (t, J=7.5, 4H), 2.30 (p, J=7.5, 4H), 1.93-1.99 (m, 4H), 1.81-1.87 (m, 4H). CNMR, 154.12, 145.55, 143.40, 139.94, 139.38, 138.83, 128.99, 126.66, 124.51, 56.85, 31.93, 31.52, 28.77, 26.88, 21.54, 20.63.

Example 76

Synthesis of Compound N,N'-[(1,1'-biphenyl)-4,4'-di-(3-propanyl)]-bis-[5,6,7,8-tetrahydroisoquinolinium] dibromide

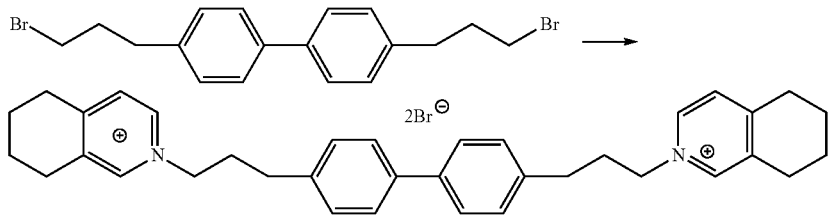

4,4'-Bis-(3-bromo-propyl)-biphenyl was added to a solution of 5,6,7,8-tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no 5,6,7,8-tetrahydroisoquinoline left in the aqueous layer. The resulting aqueous solution of the product was lyophilized to yield the pure product. (75%). ¹H NMR (300 MHz, D₂O, ppm), 8.67 (s, 2H), 8.60 (d, J=6.3, 2H), 7.68 (d, J=6.3, 2H), 7.48 (d, J=8.4, 4H), 7.29 (d, J=8.4, 4H), 4.59 (t, J=7.2, 4H), 2.94 (br, 4H), 2.86 (br, 4H), 2.81 (t, J=7.2, 4H), 2.39 (p, J-7.5, 4H), 1.74-1.85 (m, 10H), CNMR, 158.38, 143.86, 140.21, 139.39, 138.64, 138.48, 128.86, 127.91, 126.56, 60.78, 21.12, 32.00, 29.31, 26.22, 21.11.

Example 77

Synthesis of Compound N,N'-[(1,1'-biphenyl)-4,4'-di-(3-propanyl)]-bis-(4-methylpyridinium) dibromide

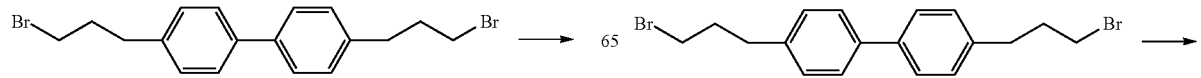

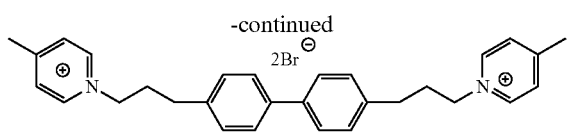

4,4'-Bis-(3-bromo-propyl)-biphenyl was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$H NMR (300 MHz, D$_2$O, ppm), 8.90 (d, J=6.6, 4H), 7.85 (d, J=6.3, 4H), 7.48 (d, J=8.4, 4H), 7.32 (d, J=8.4, 4H), 4.68 (t, J=7.5, 4H), 2.78 (t, J=7.8, 4H), 2.58 (s, 6H), 2.34 (m, 4H). CNMR, 159.77, 143.71, 139.52, 138.51, 129.08, 128.73, 126.76, 60.72, 32.76, 31.91, 21.27.

Example 78

Synthesis of Compound N,N'-[(1,1'-biphenyl)-4,4'-di-(3-propanyl)]-bis-(3-methylpyridinium) dibromide

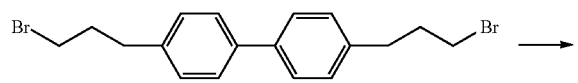

4,4'-Bis-(3-bromo-propyl)-biphenyl was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$H NMR (300 MHz, D$_2$O, ppm), 9.00 (s, 2H), 8.92 (d, J=6.3, 2H), 8.35 (d, J=7.8, 2H), 7.93 (dd, J=6.0, J=8.1, 2H), 7.46 (d, J=8.4, 4H), 7.32 (d, J=8.4, 4H), 4.72 (t, J=7.5, 4H), 2.80 (t, J=7.5, 4H), 2.50 (s, 6H), 2.35-2.44 (m, 4H). CNMR, 146.06, 144.41, 141.92, 139.82, 139.55, 138.42, 129.11, 127.61, 126.70, 61.45, 32.76, 31.99, 17.80.

Example 79

Synthesis of Compound N,N'-[(1,1'-biphenyl)-4,4'-di-(3-propanyl)]-bis-(2-methylpyridinium) dibromide

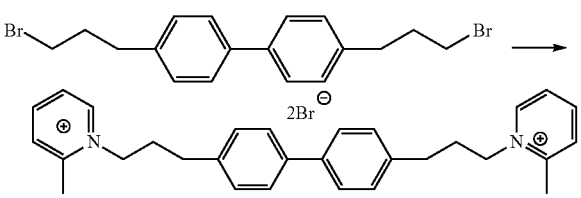

4,4'-Bis-(3-bromo-propyl)-biphenyl was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$H NMR (300 MHz, D$_2$O, ppm), 9.02 (d, 3=6.3, 2H), 8.40 (dt, J=1.5, J=7.8, 2H), 7.97 (d, J=7.8, 2H), 7.90 (t, J=6.3, 2H), 7.53 (d, J-8.1, 4H), 7.38 (d, J=8.1, 4H), 4.65 (t, J=7.8, 4H), 2.86 (t, J=7.8, 4H), 2.82 (s, 6H), 2.24-2.32 (m, 4H) CNMR, 155.49, 145.33, 145.23, 139.56, 138.54, 130.41, 129.21, 126.78, 125.89, 57.71, 31.93, 31.71, 19.75.

Example 80

Synthesis of Compound N,N'-{2,2'-[oxybis-(2,1-ethandiyloxy)]bis-ethyl}-bis-[3-(2'-S-1-methyl-pyrrolidin-2-yl)-pyridinium]dichloride

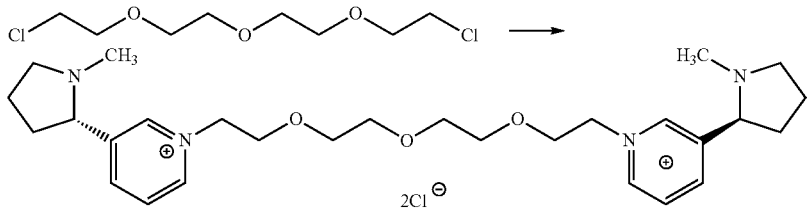

1-Chloro-2-{2-[2-(2-chloro-ethoxy)-ethoxy]-ethoxy}-ethane was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$H NMR (300 MHZ, D$_2$O, ppm), 8.63-6.64 (m, 4H), 8.38 (d, J=8.1, 2H), 7.90 (dd, J=7.8, d=6.6, 2H), 2.61-2.63 (m, 4H), 3.85 (t, J=4.8, 4H), 3.36-3.47 (m, 10H), 3.04-3.04 (m, 2H), 2.20-2.38 (m, 4H), 2.04 (s, 6H), 1.60-1.84 6H).

Example 81

Synthesis of Compound N,N'-{2,2'-[oxybis-(2,1-ethandiyloxy)]bis-ethyl}-bis(2-methylpyridinium) dichloride

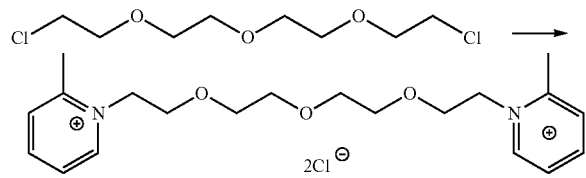

1-Chloro-2-{2-[2-(2-chloro-ethoxy)-ethoxy]-ethoxy}-ethane was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$H NMR (300 MHz, D$_2$O, ppm), 8.55 (dd, J=6.3, J=1.2, 2H), 8.23 (dt, J=7.8, J-1.5, 2H), 7.75 (d, J=7.8, 2H), 7.68 (dt, J=7.8, J=1.5, 2H), 4.62 (t, 4H), 3.82 (t, 4H), 3.40-3.44 (m, 4H), 3.35-3.39 (m, 4H), 2.36 (s, 6H).

Example 82

Synthesis of Compound N,N'-{2,2'-[oxybis-(2,1-ethandiyloxy)]bis-ethyl}-bis(3-methylpyridinium) dichloride

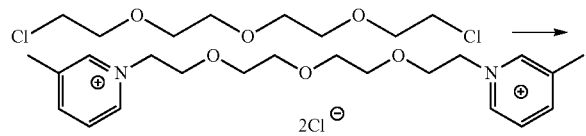

1-Chloro-2-{2-[2-(2-chloro-ethoxy)-ethoxy]-ethoxy}-ethane was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$H NMR (300 MHZ, D$_2$O, ppm), 8.54 (s, 2H), 8.49 (d, J=6.0, 8.22 (d, J=8.1, 2H), 8.76 (dd, J=8.1, J=6.0, 2H), 4.57 (t, J=4.8, 4H), 3.84 (t, J=5.1, 4H), 3.43-3.48 (m, 4H), 3.35-3.39 (m, 4H), 2.69 (s, 6H). CNMR, 146.48, 144.22, 141.89, 139.81, 127.33, 69.93, 69.60, 68.95, 60.97, 17.89.

Example 83

Synthesis of Compound N,N'-{2,2'-[oxybis-(2,1-ethandiyloxy)]bis-ethyl}-bis(4-methylpyridinium) dichloride

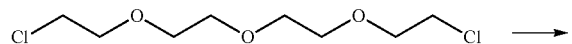

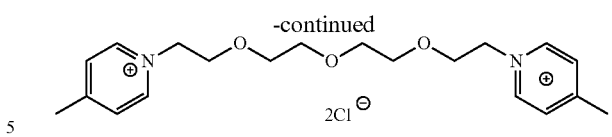

1-Chloro-2-{2-[2-(2-chloro-ethoxy)-ethoxy]-ethoxy}-ethane was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$H NMR (300 MHz, D$_2$O, ppm), 8.47 (d, J=6.9, 4H), 7.70 (d, J=6.3, 4H), 4.54 (t, J=4.8, 4H), 3.83 (t, J=4.8, 4H), 3.43-3.47 (m, 4H), 3.35-3.38 (m, 4H), 2.47 (s, 6H). CNMR, 160.56, 143.63, 128.52, 69.92, 69.57, 68.95, 60.27, 21.58.

Example 84

Synthesis of Compound N,N'-{2,2'-[oxybis-(2,1-ethandiyloxy)]bis-ethyl}-bis(5,6,7,8-tetrahydroquinolinium) dichloride

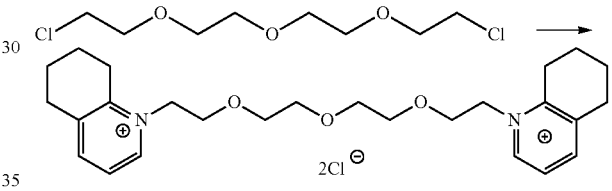

1-Chloro-2-{2-[2-(2-chloro-ethoxy)-ethoxy]-ethoxy}-ethane was added to a solution of tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroquinoline left in the aqueous layer. The resulting aqueous solution of the product was lyophilized to yield the pure product. (75%). $^1$H NMR (300 MHZ, D$_2$O, ppm), 8.39 (d, J=6.3, 2H), 8.04 (d, J=8.1, 2H), 7.55 (dd, J=8.1, J=6.3, 2H), 4.57 (t, J=4.5, 4H), 3.83 (t, J=4.5, 4H), 4.43-3.49 (m, 4H), 3.36-3.38 (m 4H), 2.98 (t, 6.3, 4H), 2.82 (t, J=6.3, 4H), 1.79-1.83 (m, 4H), 1.63-1.69 (m, 4H). CNMR, 154.58, 145.92, 143.59, 139.99, 123.92, 70.19, 69.74, 68.40, 56.28, 49.10, 28.72, 27.26, 21.40, 20.45.

Example 85

Synthesis of Compound N,N'-{2,2'-[oxybis-(2,1-ethandiyloxy)]bis-ethyl}-bis(5,6,7,8-tetrahydroisoquinolinium) dichloride

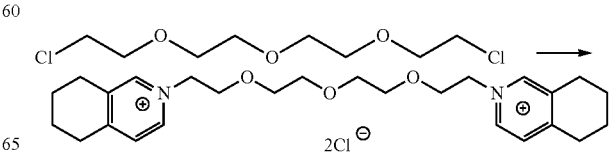

1-Chloro-2-{2-[2-(2-chloro-ethoxy)-ethoxy]-ethoxy}-ethane was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). $^1$H NMR (300 MHz, D$_2$O, ppm), 8.33 (s, 2H), 8.24 (d, J=6.3, 2H), 7.52 (d, J=6.3, 2H), 4.47 (t, J=4.8, 4H), 3.81 (t, J=4.8, 4H), 3.42-3.45 (m, 4H), 3.33-3.37 (m, 4H), 2.81-2.84 (br, 4H), 2.70-2.74 (br, 4H), 1.63-1.70 (m, 8H). CNMR, 159.33, 143.61, 140.12, 138.77, 127.74, 69.96, 69.60, 69.02, 60.12, 29.40, 26.18, 20.98, 20.95.

Example 86

Synthesis of Compound N,N'-{2,2'-[oxybis-(2,1-ethandiyloxy)]bis-ethyl}-bis-[3-(3-hydroxypropyl)-pyridinium]dichloride

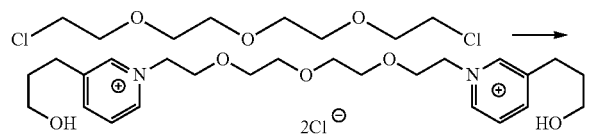

1-Chloro-2-{2-[2-(2-chloro-ethoxy)-ethoxy]-ethoxy}-ethane was added to a solution of 3-(3-hydroxypropyl)-pyridine (3 mmol) in acetonitrile and the solution refluxed for 24 hours. The acetonitrile was removed in vacuum and the resulting residue was partitioned between ether and water. The aqueous layer was washed extensively with ether until no 3-(3-hydroxypropyl)-pyridine left in the aqueous layer. The resulting aqueous solution of the product was lyophilized to yield the pure product. (75%). $^1$H NMR (300 MHz, D$_2$O, ppm), 8.59 (s, 2H), 8.53 (d, J=6.0, 8.29 (d, J=8.4, 2H), 7.81 (dd, J=8.4, J=6.0, 2H), 4.60 (t, J-4.8, 4H), 3.85 (t, J=4.5, 4H), 3.44-3.49 (m, 8H), 3.36-3.39 (m, 4H), 2.76 (t, J=7.8, 4H), 1.74-1.80 (m, 4H). CNMR. 145.99, 144.09, 143.35, 142.35, 127.64, 69.96, 69.64, 68.96, 61.06, 60.60, 31.21, 28.81.

Example 87

Synthesis of Compound N,N'-{2,2'-[oxybis-(2,1-ethandiyloxy)]bis-ethyl}-bis-(3-hydroxymethylpyridinium) dichloride

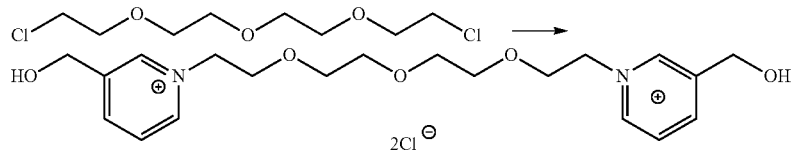

1-Chloro-2-{2-[2-(2-chloro-ethoxy)-ethoxy]-ethoxy}-ethane was added to a solution of 3-hydroxymethylpyridine (3 mmol) in acetonitrile and the solution refluxed for 24 hours. The acetonitrile was removed in vacuum and the resulting residue was partitioned between ether and water. The aqueous layer was washed extensively with ether until no 3-hydroxymethylpyridine left in the aqueous layer. The resulting aqueous solution of the product was lyophilized to yield the pure product. (75%). $^1$H NMR (300 MHZ, D$_2$O, ppm), 8.72 (s, 2H), 8.65 (d, J=6.0, 8.39 (d, J=7.8, 2H), 7.91 (t, J=6.9, 2H), 4.69 (t, J=4.8, 4H), 4.64 (s, 4H), 3.89 (t, J=4.2, 4H), 3.41-3.49 (m, 8H).

Example 88

Synthesis of Compound N,N'-{2,2'-[oxybis-(2,1-ethandiyloxy)]bis-ethyl}-bis-(2,4-dimethylpyridinium) dichloride

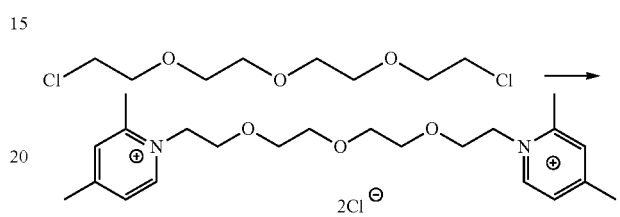

1-Chloro-2-{2-[2-(2-chloro-ethoxy)-ethoxy]-ethoxy}-ethane was added to a solution of 2,4dimethylpyridine (3 mmol) in acetonitrile and the solution refluxed for 24 hours. The acetonitrile was removed in vacuum and the resulting residue was partitioned between ether and water. The aqueous layer was washed extensively with ether until no 2,4dimethylpyridine left in the aqueous layer. The resulting aqueous solution of the product was lyophilized to yield the pure product. (75%). $^1$H NMR (300 MHZ, D$_2$O, ppm), 3.35 (d, J=6.6, 2H), 7.58 (s, 2H), 7.50 (d, J-6.6, 2H), 4.54 (t, J-4.8, 4H), 3.82 (t, J=4.8, 4H), 3.41-3.45 (m, 4H), 3.34-3.36 (m, 4H), 2.62 (s, 6H). 2.40 (s, 6H). CNMR, 159.76, 154.44, 144.47, 130.31, 126.00, 70.16, 69.66, 68.42, 56.36, 49.10, 21.27, 19.90.

Example 89

Synthesis of Compound N,N'-{2,2'-[oxybis-(2,1-ethandiyloxy)]bis-ethyl}-bis-(3,4-dimethylpyridinium) dichloride

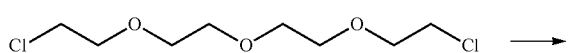

-continued

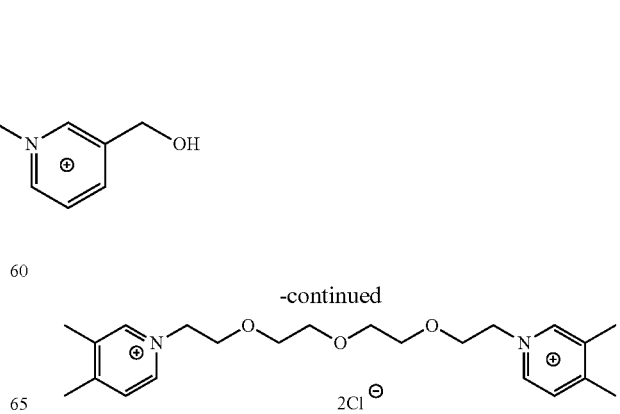

1-Chloro-2-{2-[2-(2-chloro-ethoxy)-ethoxy]-ethoxy}-ethane was added to a solution of 3,4-dimethylpyridine (3 mmol) in acetonitrile and the solution refluxed for 24 hours. The acetonitrile was removed in vacuum and the resulting residue was partitioned between ether and water. The aqueous layer was washed extensively with ether until no 3,4-dimethylpyridine left in the aqueous layer. The resulting aqueous solution of the product was lyophilized to yield the pure product. (75%). $^1$H NMR (300 MHZ, D$_2$O, ppm), 8.36 (s, 2H), 8.30 (d, J=6.3, 2H), 7.61 (d, J=6.3, 2H), 4.49 (t, J=4.8, 4H), 3.81 (t, J=4.8, 4H), 3.42-3.45 (m, 4H), 3.34-3.37 (m, 4H), 2.37 (s, 6H). 2.25 (s, 6H). CNMR, 159.23, 142.79, 141.27, 138.49, 128.06, 69.92, 69.58, 69.01, 60.08, 49.07, 19.75, 16.32.

Example 90

Synthesis of Compound N,N'-{2,2'-[oxybis-(2,1-ethandiyloxy)]bis-ethyl}-bis-(3,5-dimethylpyridinium) dichloride

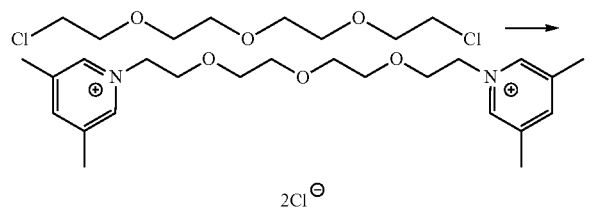

1-Chloro-2-{2-[2-(2-chloro-ethoxy)-ethoxy]-ethoxy}-ethane was added to a solution of 3,5-dimethylpyridine (3 mmol) in acetonitrile and the solution refluxed for 24 hours. The acetonitrile was removed in vacuum and the resulting residue was partitioned between ether and water. The aqueous layer was washed extensively with ether until no 3,5-dimethylpyridine left in the aqueous layer. The resulting aqueous solution of the product was lyophilized to yield the pure product. (75%). $^1$H NMR (300 MHz, D$_2$O, ppm). 8.34 (s, 4H), 8.06 (s, 2H), 4.52 (t, J=4.8, 4H), 3.83 (t, J=4.8, 4H), 3.42-3.46 (m, 4H), 3.35-3.38 (m, 4H), 2.31 (s, 12H). CNMR, 146.98, 141.42, 138.93, 69.95, 69.61, 69.01, 60.75, 49.08, 17.68.

Example 91

Synthesis of Compound N,N'-(5,7-dodecadiyn-1,12-diyl)-bis-(2-methylpyridinium) dichloride

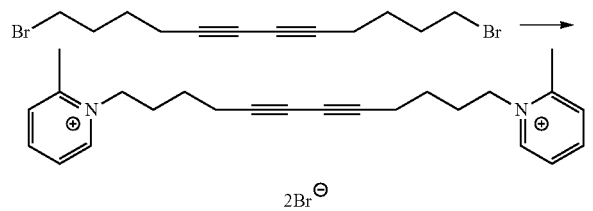

1,12-Dibromo-dodeca-5,7-diyne was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$H NMR (300 MHz, D$_2$O, ppm), 8.58 (d, 2H), 8.18-8.24 (m, 2H), 7.65-7.74 (m 4H), 4.40 (t, 4H), 2.68 (s, 6H), 2.21 (t, 4H), 1.84-1.94 (m, 4H), 1.46-1.54 (m, 4H). CNMR, 155.29, 145.16, 144.78, 130.32, 125.75, 77.89, 65.52, 57.61, 28.78, 24.44, 18.19.

Example 92

Synthesis of Compound N,N'-(5,7-dodecadiyn-1,12-diyl)-bis-(3-methylpyridinium) dichloride

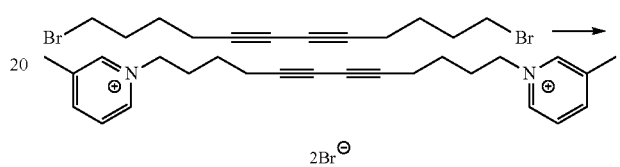

1,12-Dibromo-dodeca-5,7-diyne was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$H NMR (300 MHz, D$_2$O, ppm), 8.72 (s, 2H), 8.66 (d, 2H), 8.38 (d, 2H), 7.94 (dd, 2H). 4.59 (t, 4H), 2.58 (s, 6H), 2.32 (t, 4H), 2.28 (p, 4H), 1.59 (p, 4H). CNMR, 146.17, 143.83, 141.40, 140.11, 127.60, 77.95, 65.54, 61.35, 30.00, 24.36, 18.22, 18.00.

Example 93

Synthesis of Compound N,N'-(5,7-dodecadiyn-1,12-diyl)-bis-(4-methylpyridinium) dichloride

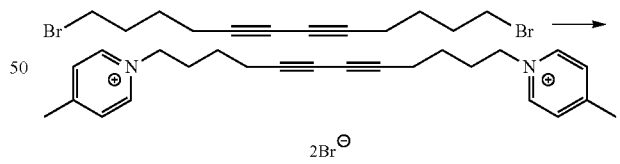

1,12-Dibromo-dodeca-5,7-diyne was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$H NMR (300 MHz, D$_2$O, ppm), 8.48 (d, 4H), 7.68 (d, 4H), 4.38 (t, 4H), 2.46 (s, 6H), 2.18 (t, 4H), 1.86-1.98 (m, 4H), 1.34-1.44 (m, 4H). CNMR, 160.12, 143.13, 128.77, 77.87, 65.47, 60.61, 29.86, 24.30, 21.56, 18.17.

Example 94

Synthesis of Compound N,N'-(5,7-dodecadiyn-1,12-diyl)-bis-(3,4-dimethylpyridinium) dichloride

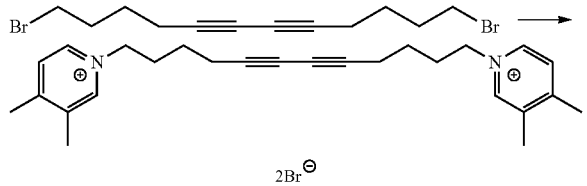

1,12-Dibromo-dodeca-5,7-diyne was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$H NMR (300 MHz, D$_2$O, ppm), 8.35 (s, 2H), 8.29 (d, 2H), 7.60 (d, 2H), 4.32 (t, 4H), 2.38 (s, 6H), 2.24 (s, 6H), 2.16 (t, 4H), 1.86-1.94 (m, 4H), 1.30-1.42 (m 4H).

Example 95

Synthesis of Compound N,N'-(5,7-dodecadiyn-1,12-diyl)-bis-(3,5-dimethylpyridinium) dichloride

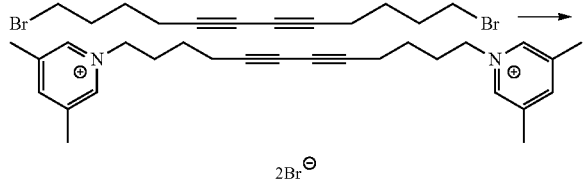

1,12-Dibromo-dodeca-5,7-diyne was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$H NMR (300 MHz, D$_2$O, ppm), 8.32 (s, 4H), 8.00 (s, 2H), 4.36 (t, 4H), 2.34 (s, 12H), 2.18 (t, 4H), 1.86-1.94 (m, 4H), 1.34-1.44 (m, 4H). CNMR, 146.62, 140.97, 139.15, 77.88, 65.41, 61.05, 29.88, 24.28, 18.14, 17.70.

Example 96

Synthesis of Compound N,N'-(5,7-dodecadiyn-1,12-diyl)-bis-(5,6,7,8-tetrahydroisoquinolinium) dichloride

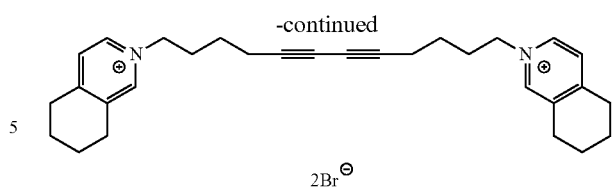

1,12-Dibromo-dodeca-5,7-diyne was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). $^1$H NMR (300 MHZ, D$_2$O, ppm), 8.34 (s, 2H), 8.22 {d, J=6.3, 2H), 7.54 (d, J-6.3, 2H), 4.31 (t, J=7.2, 4H), 2.82-2.84 (br, 4H), 2.71-2.73 (br, 4H), 2.12 (t, J=6.6, 4H), 1.81-1.91 (m, 4H), 1.64-1.69 (m, 8H), 1.29-1.38 (m, 4H). CNMR, 158.94, 143.15, 139.67, 139.05, 128.01, 77.81, 65.50, 60.46, 29.92, 29.41, 26.26, 24.38, 21.02, 21.05, 18.20.

Example 97

Synthesis of Compound N,N'-[(1,4-phenylene)-bis-(4-butynyl)]-bis-(3-methyl-pyridinium) dibromide

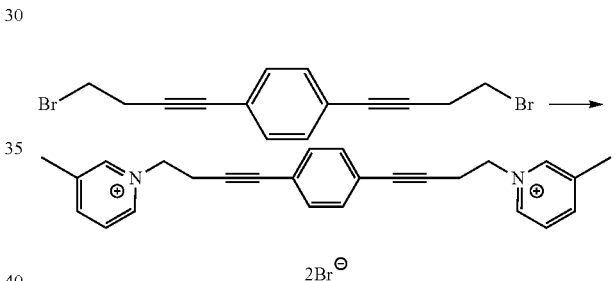

1,4-Bis-(4-bromo-but-1-ynyl)-benzene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$H NMR (300 MHz, D$_2$O, ppm), 8.67 (s, 2H), 8.60 (d, J=6.0 Hz, 2H), 8.25 (d, J=8.0 Hz, 2H), 7.80 (dd, J=6.0 Hz, J=8.0 Hz, 2H), 7.14 (s, 4H), 4.63 (m, 4H), 3.02 (t, J=6.3 Hz, 4H), 2.36 (s, 6H). CNMR, 146.68, 144.11, 141.66, 139.87, 131.59, 127.39, 122.22, 86.10, 84.40, 59.68, 21.95, 17.90.

Example 98

Synthesis of Compound N,N'-[(1,4-phenylene)-bis-(4-butynyl)]-bis-(4-methyl-pyridinium) dibromide

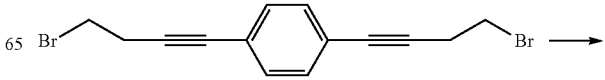

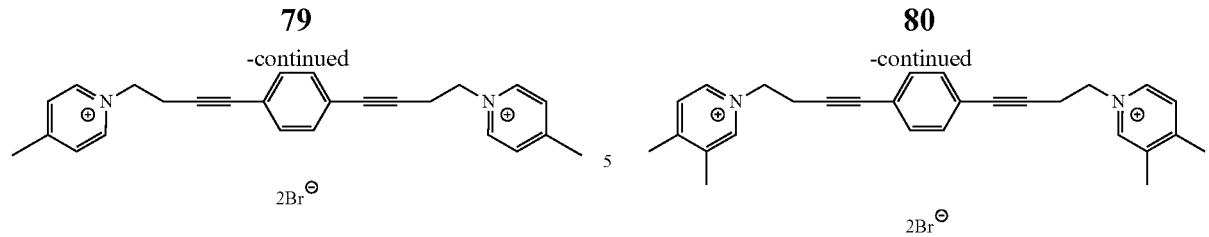

1,4-Bis-(4-bromo-but-1-ynyl)-benzene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$H NMR (300 MHz, D$_2$O, ppm), 8.60 (d, J=6.6 Hz, 4H), 7.73 (d, J=6.6 Hz, 4H), 7.15 (s, 4H), 4.60 (t, J=6 Hz, 4H), 3.01 (t, J=6.0 Hz, 2.49 (s, 6H). CNMR, 160.87, 143.41, 131.58, 128.57, 122.26, 86.16, 84.25, 59.03, 21.87, 21.68.

1,4-Bis-(4-bromo-but-1-ynyl)-benzene was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$H NMR (300 MHZ, D$_2$O, ppm), 8.50 (s, 2H), 8.44 (d, J-6.3 Hz, 2H), 7.65 (d, J=6.3 Hz, 2H), 7.13 (s, 4H), 4.57 (t, J=6.3 Hz, 4H), 2.99 (t, J=6.3 Hz, 4H), 2.38 (s, 6H), 2.24 (s, 6H).

Example 99

Synthesis of Compound N,N'-[(1,4-phenylene)-bis-(4-butynyl)]-bis-(5,6,7,8-tetrahydroisoquiolinium) dibromide Example 101

Synthesis of Compound N,N'-[(1,4-phenylene)-bis-(4-butynyl)]-bis-(3,5-dimethyl-pyridinium) dibromide [ZZ 1 111]

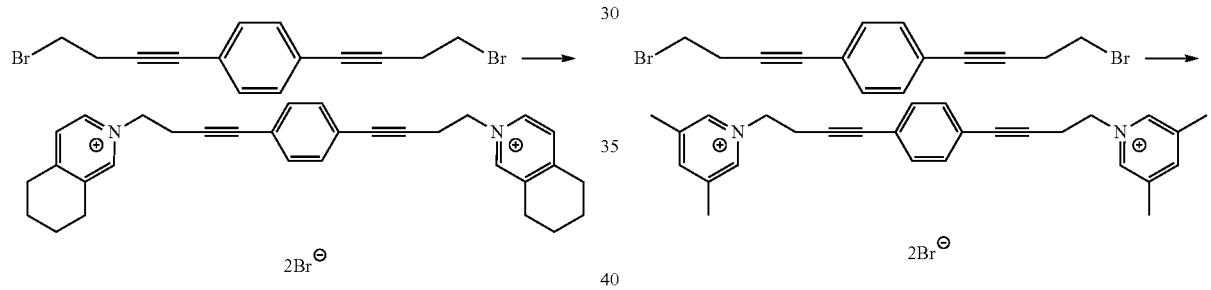

1,4-Bis-(4-bromo-but-1-ynyl)-benzene was added to a solution of terahydroisoquinoline (3 mmol) in acetonitrile and the solution refluxed for 24 hours. The acetonitrile was removed in vacuum and the resulting residue was partitioned between ether and water. The aqueous layer was washed extensively with ether until no terahydroisoquinoline left in the aqueous layer. The resulting aqueous solution of the product was lyophilized to yield the pure product. (75%). $^1$H NMR (300 MHz, D$_2$O, ppm), 8.46 (s, 2H), 8.35 (d, J=6.6 Hz, 2H), 7.56 (d, J=6.6 Hz, 2H), 7.09 (s, 4H), 4.54 (t, J=6.3 Hz, 4H), 2.98 (t, J-6.3 Hz, 4H), 2.83 (t, J=6.0 Hz, 4H), 2.66 (t, J=5.4 Hz, 4H), 1.64-1.68 (m, 8H).

1,4-Bis-(4-bromo-but-1-ynyl)-benzene was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$H NMR (300 MHZ, D$_2$O, ppm), 8.46 (s, 4H), 8.04 (s, 2H), 7.11 (s, 4H), 4.59 (t, J=6.3 Hz, 4H), 2.99 (t, J=6.3 Hz, 4H), 2.29 (s, 12H). CNMR, 147.17, 141.31, 138.96, 131.59, 122.24, 86.31, 84.46, 59.45, 21.99, 17.73.

Example 100

Synthesis of Compound N,N'-[(1,4-phenylene)-bis-(4-butynyl)]-bis-(3,4-dimethyl-pyridinium) dibromide [ZZ-1-110]

Example 102

Synthesis of Compound N,N'-[(1,1'-biphenyl)-4,4'-di-(1-propyn-3-yl)]-bis-(3-methylpyridinium) dibromide

-continued

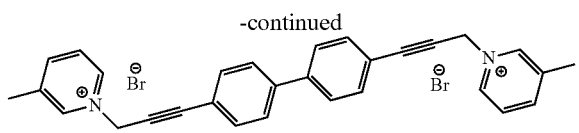

4,4'-Bis-(3-bromo-prop-1-ynyl)-biphenyl (1 mmol) was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$H NMR (300 MHz, $d_6$-DMSO, ppm), 9.16 (s, 2H), 9.12 (s, 2H), 8.54 (d, 2H), 8.22 (dd, 2H), 7.8 (d, 4H), 7.62 (d, 4H), 5.8 (s, 4H), 2.4 (s, 6H). CNMR, 147.52, 144.53, 142.46, 140.44, 139.73, 133.14, 128.36, 127.69, 120.85, 89.16, 82.81, 51.19, 18.79.

Example 103

Synthesis of Compound N,N'-[(1,1'-biphenyl)-4,4'-di-(1-propyn-3-yl)]-bis-(4-methylpyridinium) dibromide

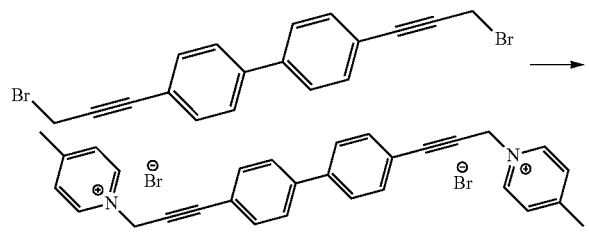

4,4'-Bis-(3-bromo-prop-1-ynyl)-biphenyl (1 mmol) was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$H NMR (300 MHZ, $d_6$-DMSO, ppm), 9.05 (d, 4H), 8.06 (d, 4H), 7.78 (d, 4H), 7.62 (d, 4H), 5.8 (s, 4H), 2.62 (s, 6H). CNMR, 160.67, 144.10, 140.41, 133.11, 129.27, 127.69, 120.85, 89.06, 82.97, 50.56, 22.39.

Example 104

Synthesis of Compound N,N'-[(1,1'-biphenyl)-4,4'-di-(1-propyn-3-yl)]-bis-(3,4-dimethylpyridinium) dibromide [ZZ-1-61 C]

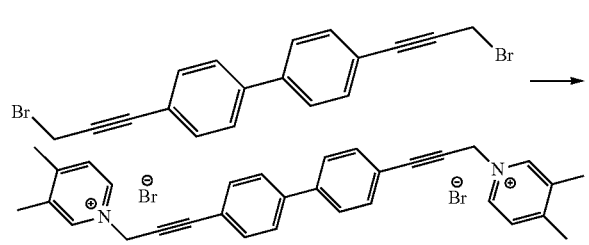

4,4'-Bis-(3-bromo-prop-1-ynyl)-biphenyl (1 mmol) was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$H NMR (300 MHz, $d_6$-DMSO, ppm), 9.02 (s, 2H), 8.88 (d, 2H), 8.0 (d, 2H), 7.8 (d, 4H), 7.6 (d, 4H), 5.9 (s, 4H), 2.46 (s, 6H), 2.40 (s, 6H). CNMR, 159.64, 143.10, 141.96, 140.39, 138.65, 133.12, 128.88, 127.68, 120.88, 88.83, 83.08, 50.41, 20.66, 17.19.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

Example 105

Persistent Inflammatory Pain Model

Figure 2:
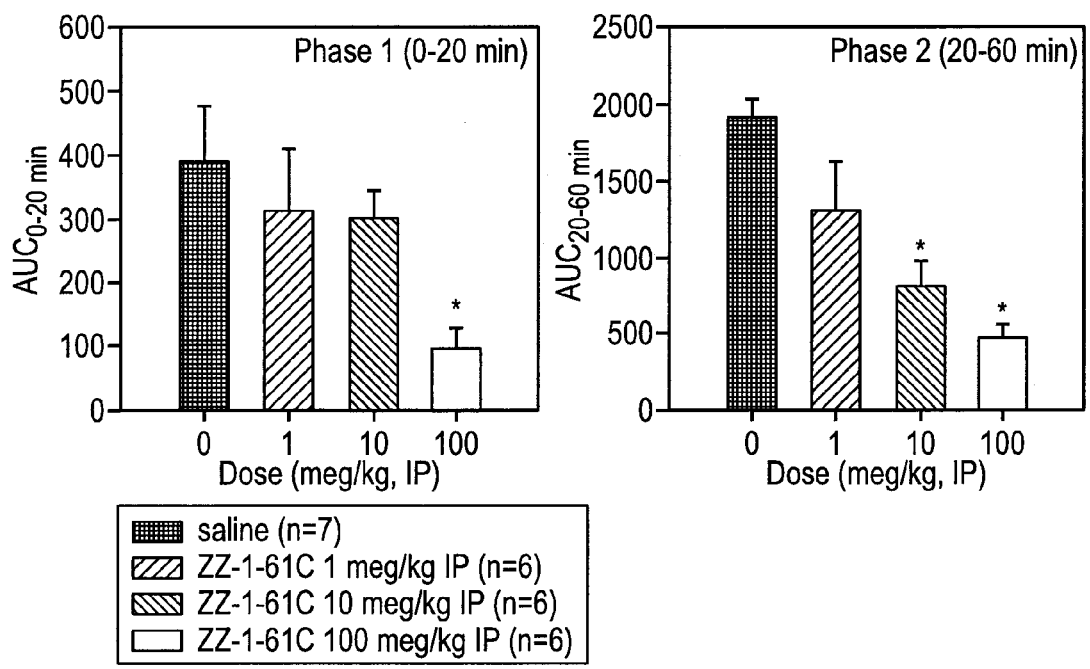
FIG. 2 shows the dose response of the analgesic effects of ZZ-1-61C in the rodent persistent inflammatory pain model following intraperitoneal administration. Data are mean S.E.M. (n=6 rats/dose).

A rat model of tonic inflammatory pain (the formalin test) was used in this study (Wheeler-Aceto and Cowan, 1991). Fifty ul of formalin (5%) was injected subcutaneously (SC) into the dorsal surface of the left hind paw. This procedure typically produces a biphasic behavioral response consisting of flinching, lifting and licking. The first phase (0-10 min) is thought to result from direct stimulation of nociceptors (nociceptive pain) whereas the second phase (20-60 min) is thought to involve central sensitization resulting from continued activation of receptors (TRPA1) with an important role in inflammatory pain. Rats were pretreated 15 min prior to formalin (SC) injection with ZZ-16-1C as synthesized in Example 104 and administered by the I.P. route. Saline served as control. Incidences of formalin-induced flinching were counted continuously in 5 min intervals for 60 min. Each rat received only one treatment. The results are presented in FIGS. 1 and 2. FIG. 1 shows the time course of the effect of intraperitoneal administration of varying doses of ZZ-16-1C in the rodent model of tonic inflammatory pain. The drug produced a decrease in the number of twitches in both phases of the formalin test indicating it's a analgesic effect in this. The effect of the drug remained significant even at 60 min. FIG. 2 shows the dose response effect of ZZ-16-1C following intraperitoneal administration in the rodent model of tonic inflammatory pain. The effect of the drug was dose-related. Both phases of the formalin test were affected, however, ZZ-6-1C was more effective in phase 2 than phase 1.

Example 106

Figure 3:
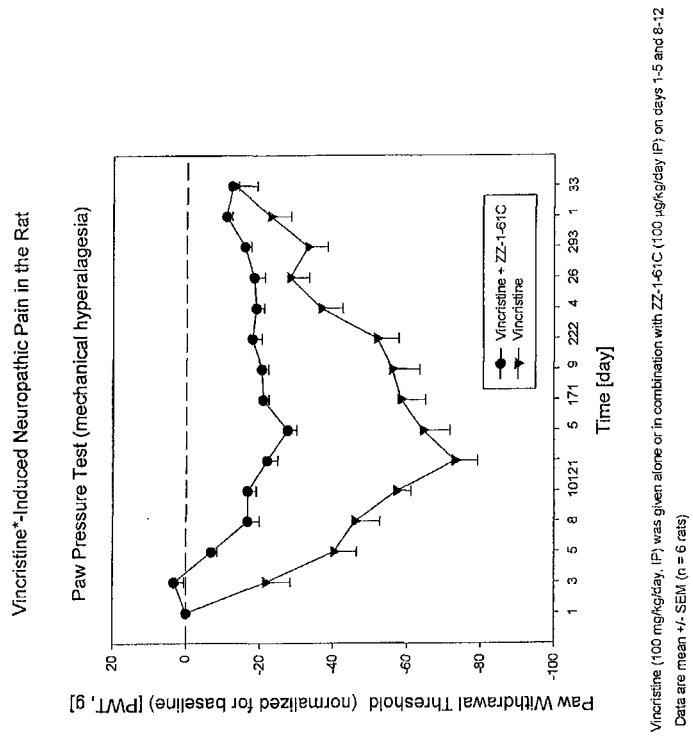
FIG. 3 provides a graph showing the anti-hyperalgesic effects of ZZ-1-61C in the paw pressure test.

Study of the Anti-Hyperalgesic Effects of ZZ-1-61C Following Intraperitoneal Administration in a Rodent Model of Chemotherapy-Induced Pain A study was performed to screen the analgesic activity of ZZ-1-61C following administration by the intraperitoneal (IP) route in the rodent model of chemotherapy-induced pain. A well accepted preclinical model of neuropathic pain that produced enhanced pain sensitivity similar to that observed as a result of chemotherapy administration in humans was employed (Polomano and Bennett, 2001). Rats were injected (IP) with vincristine, a vinca alkaloid antitumor agent, using two 5-day cycles (100 ug/kg/day). Rats typically develop a neuropathic pain state with hypersensitivity to pain as a result of nerve damage induced by the vincristine. The ability of ZZ-1-61C to prevent chemotherapy-induced neuropathic pain was determined as follows. Male rats (N=6) were given 100 ug/kg of ZZ-1-61C in combination with vincristine. The control group (N=6) was given vincristine alone. Mechanical hyperalgesia was assessed employing the paw pressure test (32 g/sec, 300 g cut-off) as described by Randal and Selitto (1957) using a Basile Analgesimeter (UGO Basile, Italy) with vocalization as an end-point. The results are presented in FIG. 3. The ZZ-1-61C was effective in blocking the development of chemotherapy-induced neuropathic pain (anti-hyperalgesic effect) by the vincristine.

Example 107

Figure 4:
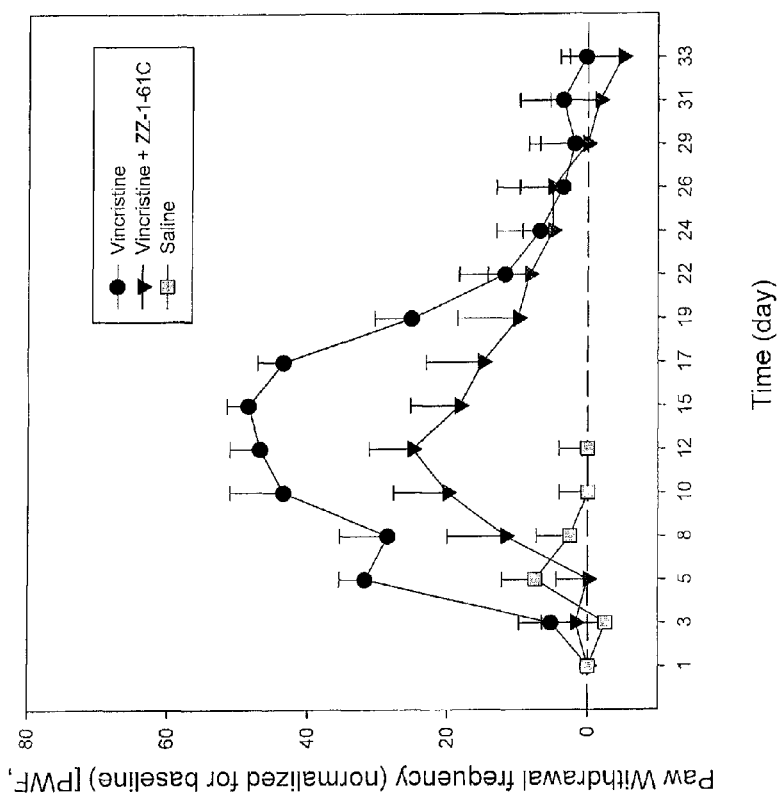
FIG. 4 provides a graph showing the anti-allodynic effect of ZZ-1-61C in a rodent model of chemotherapy-induced pain by determining paw withdrawal frequency.

Study of the Anti-Allodynic Effect of ZZ-1-61 C Following Intraperitoneal Administration in a Rodent Model of Chemotherapy-Induced Pain A study was performed to screen the analgesic activity of ZZ-1-61C following administration by the intraperitoneal (IP) route in the rodent model of chemotherapy-induced pain. A well accepted preclinical model of neuropathic pain that produced enhanced pain sensitivity similar to that observed as a result of chemotherapy administration in humans was employed (Polomano and Bennett, 2001). Rats were injected (IP) with vincristine, a vinca alkaloid antitumor agent, using two 5-day cycles (100 ug/kg/day). Rats typically develop a neuropathic pain state with hypersensitivity to pain as a result of nerve damage induced by the vincristine. The ability of ZZ-1-61C to prevent chemotherapy-induced neuropathic pain was determined as follows. Male rats (N=6) were injected with vincristine as describe above. The rats were then given ZZ-1-61C at a dose of 100 ug/kg following completion of the chemotherapy regimen. A second group of rats (N=6) was given vincristine alone. The control group received saline. Rats were placed on an elevated mesh floor and von Frey Filaments (Stoelting, Wood Dale, Ill.) with bending forces of 4 g and 15 gm were applied to the plantar surfaces of both hind paws. A positive response was regarded as a sharp withdrawl of the paw. The results are presented in FIG. 4. The ZZ-1-61C was effective in reducing the allodynia (anti-allodynic effect) produced by vincristine.

Example 108

Figure 5:
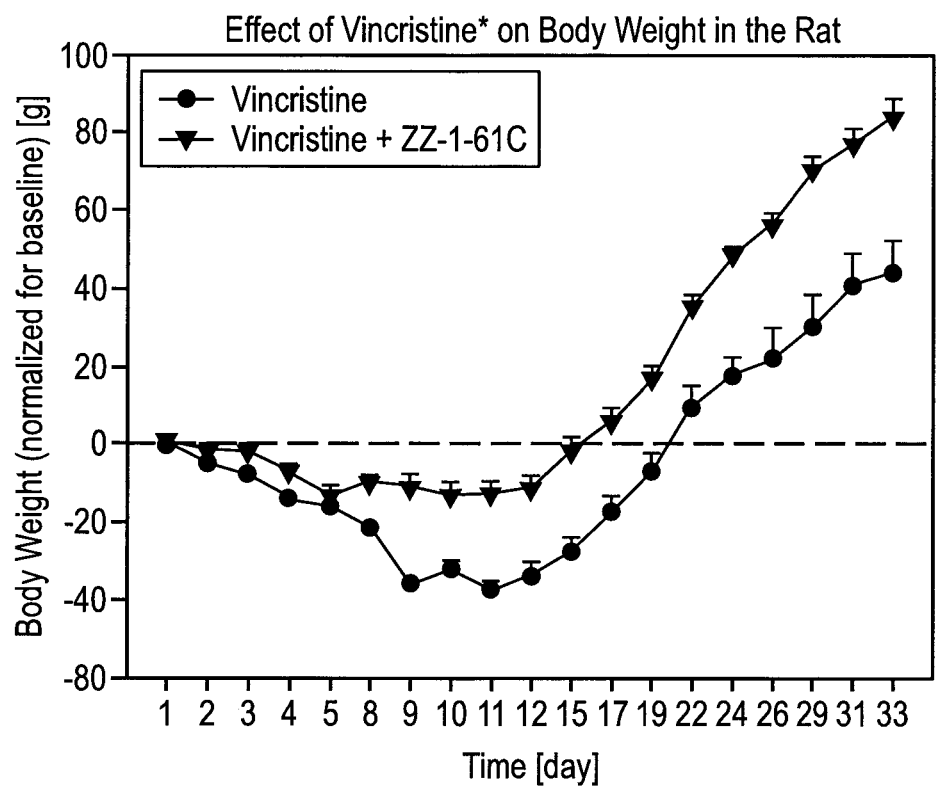
FIG. 5 provides a graph showing the effect of ZZ-1-61C on the toxicity (body weight loss) of vineristine in a rodent model of chemotheraopy-induced pain.

Study of the Effect of ZZ-1-61C on the Toxicity (Body Weight Loss) of Vincristine in a Rodent Model of Chemotherapy-Induced Pain A study was performed to assess the ability of ZZ-1-61C to prevent loss of body weight typically induced by vincristine follow administration in a rodent model of chemotherapy-induced pain. A well accepted preclinical model of neuropathic pain that produced enhanced pain sensitivity similar to that observed as a result of chemotherapy administration in humans was employed (Polomano and Bennett, 2001). Rats were injected (IP) with vincristine, a vinca alkaloid anti-tumor agent, using two 5-day cycles (100 ug/kg/day). Rats typically develop a neuropathic pain state with hypersensitivity to pain as a result of nerve damage induced by the vincristine accompanied by weight loss. The ability of ZZ-1-61C to prevent chemotherapy-induced toxicity manifested as weight loss was determined as follows. Male rats (N=6) were given 100 ug/kg of ZZ-1-61C in combination with vincristine. The control group (N=6) was given vincristine alone. Body weight was assessed on a daily basis. The results are presented in FIG. 5. The ZZ-1-61C was able to obtund the weight loss in the rats normally seen as a result of vincristine administration in the chemotherapy-induced pain model.

Example 109

Bis Analogs Ability to Block α9α 10 nAChR

Bis analogs were tested for their ability to block α9α 10 nAChRs. Cloned nAChR subunits were heterologously expressed in *Xenopus* oocytes, voltage-clamped and exposed to ACh and compounds as previously described in Vincler, M. et al., Molecular mechanism for analgesia involving specific antagonism of alpha9alpha10 nicotinic acetylcholine receptors, Proc Natl Acad Sci USA 2006, 103: 17880-17884 and Cartier G E et al., A new alpha-Conotoxin which targets alpha3best2Nicotinic Acetylcholine Receptors, J. Biol. Chem. 1996, 271:7522-7528. Briefly, the oocyte chamber consisting of a cylindrical well (~30 μl in volume) was gravity perfused at a rate of ~2 ml/min with ND96 containing 0.01% (wt/vol) BSA. Oocytes were exposed once a minute to 1 sec pulses of ACh. The ACh concentration was 10 μM. Compounds were applied at the beginning of a 5 min static bath incubation. The % block was calculated as a % of ND96 control (no compound) response.

Results are shown in Table I. SEM represents the standard error of the mean. The results indicate that bis compounds consisting of a variety of different structures are activity at blocking α9α 10 nAChRs, the therapeutic target.

TABLE I

| Compound | % Block at 100 nM | SEM |
| --- | --- | --- |
| GZ 585 B | 68.9 | 8.6 |
| GZ 582 B | 72.0 | 3.9 |
| GZ 581 B | 68.7 | 5.8 |
| GZ 584 B | 28.0 | 6.9 |
| GZ 581 A | 32.4 | 16.9 |
| GZ 584 A | −24.4 | 10.2 |
| GZ 578 B | 37.3 | 7.7 |
| GZ 570 B | 23.1 | 11.9 |
| GZ 571 A | 58.4 | 6.7 |
| GZ 579 B | 62.5 | 6.6 |
| ZZ 1 81 | 63.3 | 11.3 |
| ZZ 1 82 | 2.9 | 9.9 |
| ZZ 1 110 | 89.4 | 4.6 |
| ZZ 1 111 | 23.8 | 8.3 |
| ZZ 55 G | 65.4 | 9.8 |
| ZZ 55 C | 10.7 | 10.8 |
| ZZ 1 55 D | −13.8 | 4.6 |
| ZZ 161 C | 91.9 | 6.1 |

Structures of GZ-Compounds
GZ-585 B
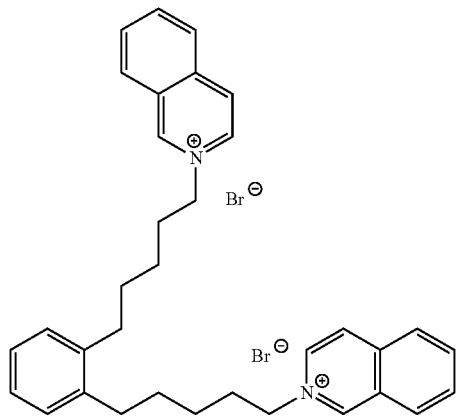
GZ 582 B
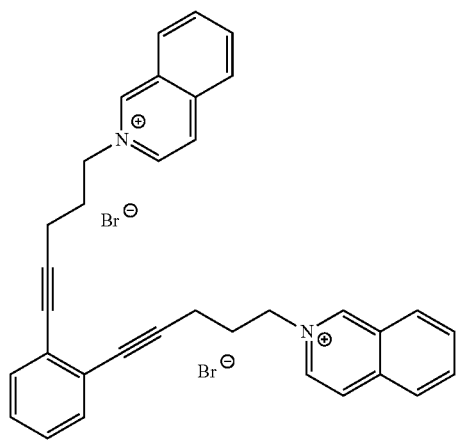
GZ 581 B
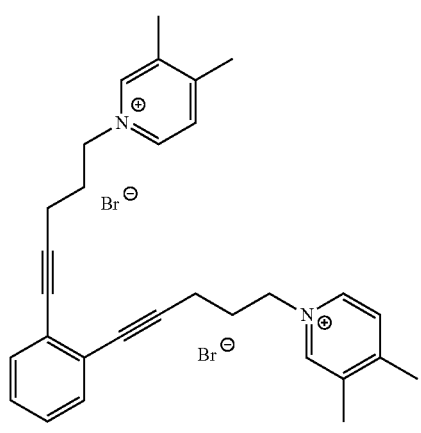
GZ 584 B
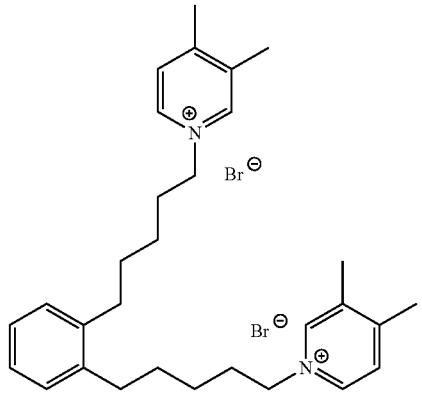
GZ 581 A
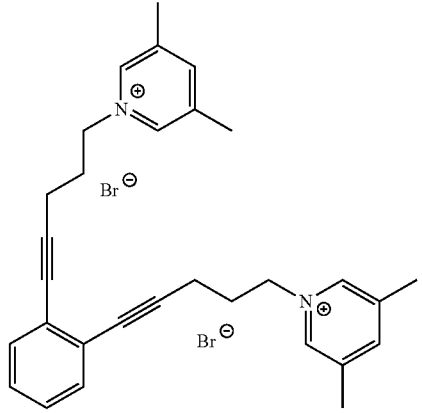
GZ 584 A
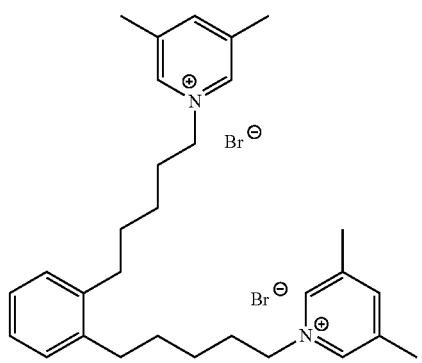
GZ 578 B
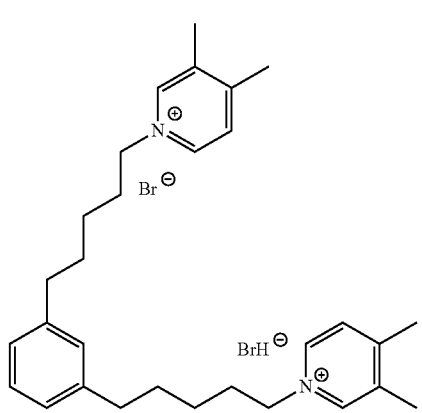

GZ 570 B
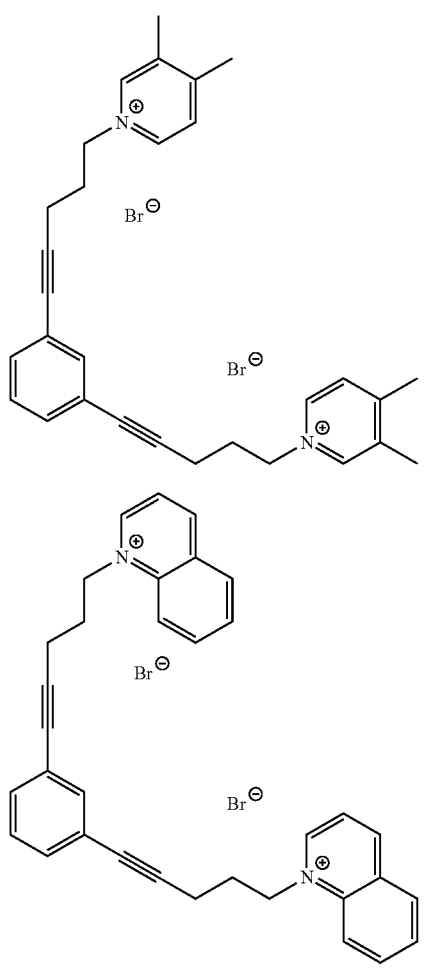
GZ 571 A
GZ 579 B
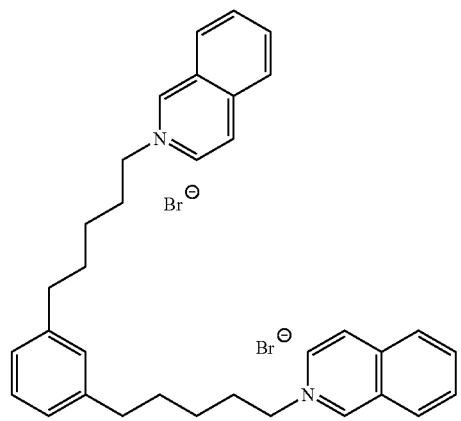
Structures of ZZ-Compounds
ZZ-1 81
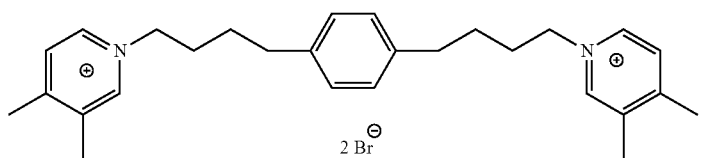
ZZ 1 82
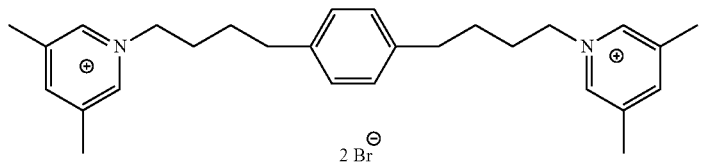
ZZ-1-110
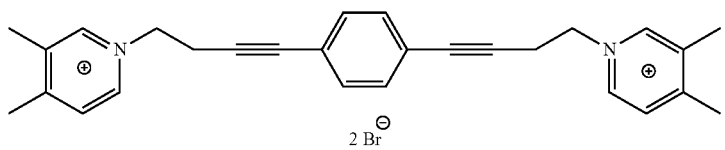

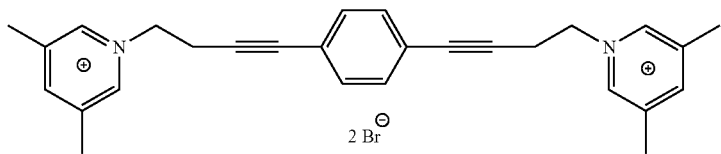
ZZ 1 111

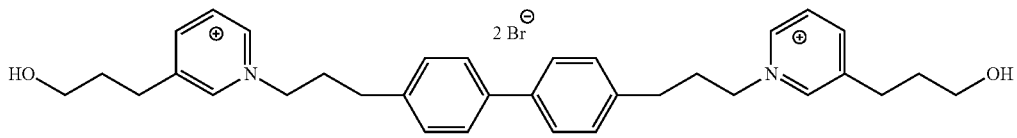
ZZ 55 G

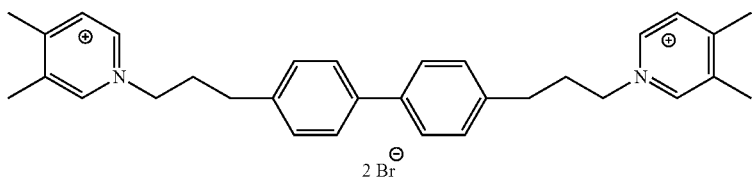
ZZ 55 C

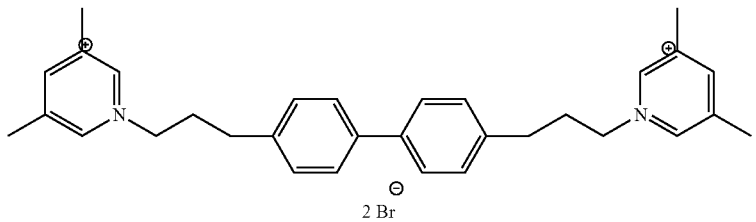
ZZ 1 55 D

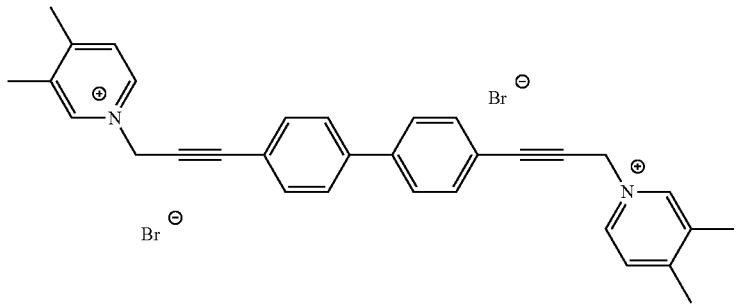
ZZ 161 C

We claim the following:

1. A method of blocking the nicotinic acetylcholine receptor α9α10nAChR, comprising administering to a mammalian subject in need thereof a pharmaceutically acceptable amount of a compound-of Formula (I)

$$X^{2\ominus\prime}R^{1}\text{—}H_2C\text{-}L^1\text{-}Q\text{-}L^2\text{-}CH_2\text{—}R^{2\oplus}X^{1\ominus\prime} \quad (I)$$

wherein $X^{1\ominus\prime}$ and $X^{2\ominus\prime}$ are each independently an organic or inorganic anion; and wherein $-L_1\text{-}Q\text{-}L_2-$ is $-(CH_2)_4\text{-}1,2\text{-phenyl-}(CH_2)_4-$; $R^{1\oplus}$ and $R^{2\oplus}$ are rings represented by the formula

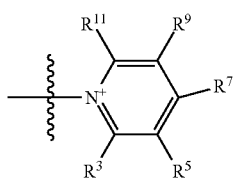

wherein $R^3$ is hydrogen or methyl; $R^5$ is hydrogen, methyl, ethyl, butyl, phenyl, 1-methyl-2-pyrrolidinyl, bromo, hydroxymethyl or hydroxypropyl; $R^7$ is hydrogen or methyl; $R^9$ is hydrogen; and $R^{11}$ is hydrogen; or $R^{1\oplus}$ and $R^{2\oplus}$ are

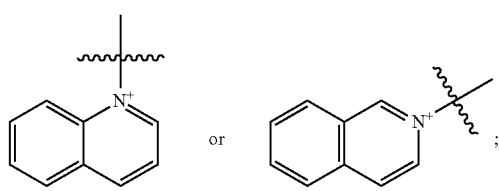 [SMILES: *[n+]1cccc2ccccc21 ; *[n+]1ccc2ccccc2c1]

or wherein $-L_1\text{-}Q\text{-}L_2-$ is $-(CH_2)_4\text{-}1,3\text{-phenyl-}(CH_2)_4-$; $R^{1\oplus}$ and $R^{2\oplus}$ are rings represented by the formula

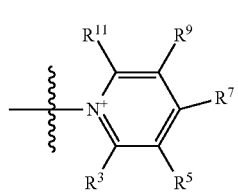

wherein R³ is hydrogen or methyl; R⁵ is hydrogen, methyl, ethyl, butyl, phenyl, 1-methyl-2-pyrrolidinyl, bromo, hydroxymethyl or hydroxypropyl; R⁷ is hydrogen or methyl; R⁹ is hydrogen or methyl; and R¹¹ is hydrogen; or $R^{1\oplus}$ and $R^{2\oplus}$ are

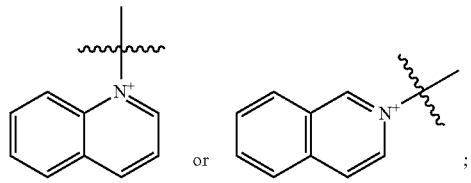 [SMILES: *[n+]1cccc2ccccc21 ; *[n+]1ccc2ccccc2c1]

or or wherein -L₁-Q-L₂- is —(CH₂)₃-1,4-phenyl-(CH₂)₃—; $R^{1\oplus}$ and $R^{2\oplus}$ are rings represented by the formula

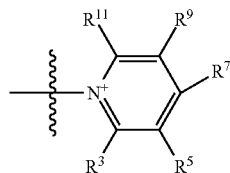

wherein R³ is hydrogen or methyl; R⁵ is hydrogen, methyl, ethyl, butyl, phenyl, 1-methyl-2-pyrrolidinyl, bromo, hydroxymethyl or hydroxypropyl; R⁷ is hydrogen or methyl; R⁹ is hydrogen; and R¹¹ is hydrogen; or $R^{1\oplus}$ and $R^{2\oplus}$ are

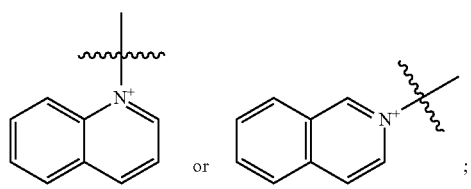 [SMILES: *[n+]1cccc2ccccc21 ; *[n+]1ccc2ccccc2c1]

or wherein -L₁-Q-L₂- is —(CH₂)₂-4,4'-biphenyl-(CH₂)₂—; $R^{1\oplus}$ and $R^{2\oplus}$ are rings represented by the formula

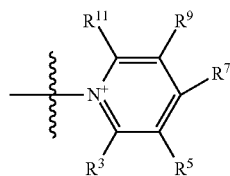

wherein R³ is hydrogen or methyl; R⁵ is hydrogen, ethyl, butyl, phenyl, 1-methyl-2-pyrrolidinyl, bromo, hydroxymethyl or hydroxypropyl; R⁷ is hydrogen or methyl; R⁹ is hydrogen or methyl; and R¹¹ is hydrogen; or $R^{1\oplus}$ and $R^{2\oplus}$ are

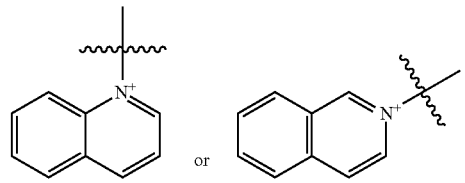

or wherein -L₁-Q-L₂- is —(CH₂)₂—C≡C-1,2-phenyl-C≡C—(CH₂)₂—; $R^{1\oplus}$ and $R^{2\oplus}$ are rings represented by the formula

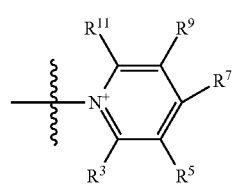

wherein R³ is hydrogen or methyl; R⁵ is hydrogen, methyl, ethyl, butyl, phenyl, 1-methyl-2-pyrrolidinyl, bromo, hydroxymethyl or hydroxypropyl; R⁷ is hydrogen or methyl; R⁹ is hydrogen or methyl; and R¹¹ is hydrogen; or $R^{1\oplus}$ and $R^{2\oplus}$ are

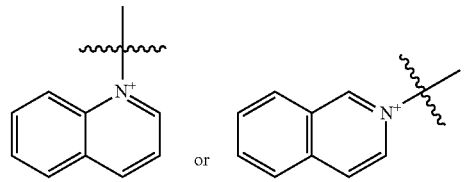

or wherein -L₁-Q-L₂- is —(CH₂)₂—C≡C-1,3-phenyl-C≡C—(CH₂)₂—; $R^{1\oplus}$ and $R^{2\oplus}$ are rings represented by the formula

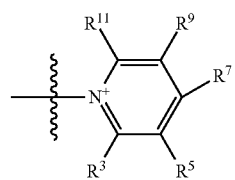

wherein R³ is hydrogen or methyl; R⁵ is hydrogen, methyl, ethyl, butyl, phenyl, 1-methyl-2-pyrrolidinyl, bromo, hydroxymethyl or hydroxypropyl; R⁷ is hydrogen or methyl; R⁹ is hydrogen or methyl; and R¹¹ is hydrogen; or $R^{1\oplus}$ and $R^{2\oplus}$ are

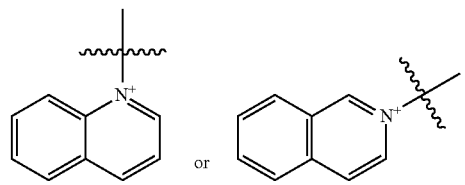

or or
 wherein -L$_1$-Q-L$_2$- is —CH$_2$—C≡C-1,4-phenyl-C≡C—CH$_2$—; R$^{1\oplus}$ and R$^{2\oplus}$ are rings represented by the formula

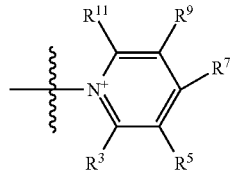

wherein R$^3$ is hydrogen or methyl; R$^5$ is hydrogen, methyl, ethyl, butyl, phenyl, 1-methyl-2-pyrrolidinyl, bromo, hydroxymethyl or hydroxypropyl; R$^7$ is hydrogen or methyl; R$^9$ is hydrogen or methyl; and R$^{11}$ is hydrogen; or R$^{1\oplus}$ and R$^{2\oplus}$ are

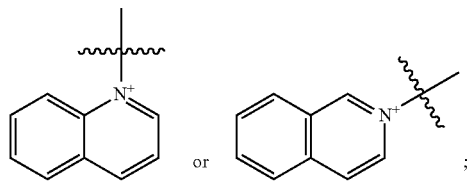 [SMILES: *[n+]1cccc2ccccc21 ; *[n+]1ccc2ccccc2c1]

or
 wherein -L$_1$-Q-L$_2$- is —C≡C-4,4'-biphenyl-C≡C—; R$^{1\oplus}$ and R$^{2\oplus}$ are rings represented by the formula

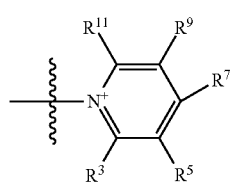

wherein R$^3$ is hydrogen or methyl; R$^5$ is hydrogen, methyl, ethyl, butyl, phenyl, 1-methyl-2-pyrrolidinyl, bromo, hydroxymethyl or hydroxypropyl; R$^7$ is hydrogen or methyl; R$^9$ is hydrogen or methyl; and R$^{11}$ is hydrogen; or R$^{1\oplus}$ and R$^{2\oplus}$ are

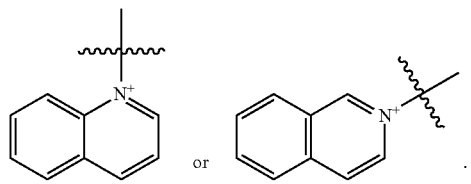 [SMILES: *[n+]1cccc2ccccc21 ; *[n+]1ccc2ccccc2c1]

2. A method of blocking the nicotinic acetylcholine receptor α9α10nAChR, comprising administering to a mammalian subject in need thereof a pharmaceutically acceptable amount of a compound selected from the group consisting of:

N,N'[1,4-phenylenedi-(4-butanyl)]-bis-(3,4-dimethyl-pyridinium) dibromide;
1,2-bis-[5-(3,4-dimethyl-pyridinium)-pent-1-ynyl]-benzene dibromide;
1,2-bis-[5-(3,5-dimethyl-pyridinium)-pent-1-ynyl]-benzene dibromide;
1,2-bis-[5-isoquinolinium-pent-1-ynyl)-benzene dibromide;
1,2-bis-[5-(3,4-dimethyl-pyridinium)-pentyl]-benzene dibromide;
1,2-bis-[5-isoquinolinium-pentyl)-benzene dibromide;
1,3-bis-[5-(3,4-dimethyl-pyridiniiim)-pent-1-ynyl]-benzene dibromide;
1,3-bis-(5-quinolinium-pent-1-ynyl)-benzene dibromide;
1,3-bis-[5-(3,4-dimethyl-pyridinium)-pentyl]-benzene dibromide;
1,3-bis-(5-isoquinolinium-pentyl)-benzene dibromide;
N,N'-[(1,1'-biphenyl)-4,4'-di-(3-propanyl)]-bis-[3-(3-hydroxy-propyl)-pyridinium] dibromide;
N,N'-[(1,4-phenylene)-bis-(4-butynyl)]-bis-(3,4-dimethyl-pyridinium) dibromide;
N,N'-[(1,4-phenylene)-bis-(4-butynyl)]-bis-(3,5-dimethyl-pyridinium) dibromide; and
N,N'-[(1,1'-biphenyl)-4,4'-di-(1-propyn-3-yl)]-bis-(3,4-dimethylpyridinium) dibromide.

3. The method of claim 2, wherein the compound is N,N'-[(1,1'-biphenyl)-4,4'-di-(1-propyn-3-yl)]-bis-(3,4-dimethylpyridinium) dibromide.

4. The method of claim 2, wherein the compound is N,N'-[(1,4-phenylene)-bis-(4-butynyl)]-bis-(3,4-dimethyl-pyridinium) dibromide.

5. The method of claim 1, wherein -L$_1$-Q-L$_2$- is —(CH$_2$)$_4$-1,2-phenyl-(CH$_2$)$_4$— and R$^{1\oplus}$ and R$^{2\oplus}$ are each

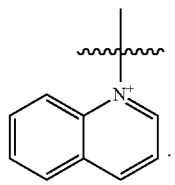 [SMILES: *[n+]1cccc2ccccc21]

6. The method of claim 1, wherein X$^{1\ominus i}$ and X$^{2\ominus i}$ are each bromide, -L$_1$-Q-L$_2$- is —(CH$_2$)$_4$-1,2-phenyl-(CH$_2$)$_4$—, and R$^{1\oplus}$ and R$^{2\oplus}$ are each

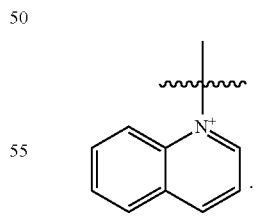

* * * * *